US012221465B2

(12) United States Patent
Joglekar et al.

(10) Patent No.: US 12,221,465 B2
(45) Date of Patent: Feb. 11, 2025

(54) SIGNALING AND ANTIGEN-PRESENTING BIFUNCTIONAL RECEPTORS (SABR)

(71) Applicant: California Institute of Technology, Pasadena, CA (US)

(72) Inventors: Alok V Joglekar, Pasadena, CA (US); Michael T Leonard, Pasadena, CA (US); Michael T Bethune, Pasadena, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 461 days.

(21) Appl. No.: 16/122,562

(22) Filed: Sep. 5, 2018

(65) Prior Publication Data
US 2019/0201443 A1    Jul. 4, 2019

Related U.S. Application Data

(60) Provisional application No. 62/554,652, filed on Sep. 6, 2017.

(51) Int. Cl.
*C07K 14/705*    (2006.01)
*A61K 39/00*    (2006.01)
(Continued)

(52) U.S. Cl.
CPC ...... *C07K 14/7051* (2013.01); *A61K 39/4611* (2023.05); *A61K 39/4615* (2023.05); *A61K 39/4621* (2023.05); *A61K 39/4622* (2023.05); *A61K 39/4632* (2023.05); *A61K 39/46433* (2023.05); *A61K 39/464401* (2023.05); *A61K 39/464488* (2023.05);
(Continued)

(58) Field of Classification Search
None
See application file for complete search history.

(56) References Cited

U.S. PATENT DOCUMENTS 6,491,908 B1    12/2002    Rosenberg
7,319,143 B2 †    1/2008    Gross
(Continued)

FOREIGN PATENT DOCUMENTS

WO    WO 01/91698 A2    12/2001
WO    WO 01/91698 A3    12/2001
(Continued)

OTHER PUBLICATIONS

HLA Nomenclature (2015) (Year: 2015).*
(Continued)

*Primary Examiner* — Michael Szperka
*Assistant Examiner* — Marianne Dibrino
(74) *Attorney, Agent, or Firm* — KNOBBE, MARTENS, OLSON & BEAR, LLP

(57) ABSTRACT

Described herein are compositions and methods for signaling and antigen-presenting bifunctional receptors (SABRs) comprising one or more antigen presenting domains; and one or more signal transduction domains, wherein the one or more antigen presenting domains comprise a binding fragment of a major histocompatibility complex (MHC) molecule. Various immunological functions of the SABRs are also described.

10 Claims, 55 Drawing Sheets

Specification includes a Sequence Listing.

(51) Int. Cl.
   *A61P 37/00* (2006.01)
   *C07K 14/725* (2006.01)
   *C07K 14/74* (2006.01)
   *C12N 5/0783* (2010.01)
   *C40B 40/02* (2006.01)
   *G01N 33/566* (2006.01)
   *G01N 33/68* (2006.01)
   *A61K 38/00* (2006.01)

(52) U.S. Cl.
   CPC .......... *A61K 39/464491* (2023.05); *A61K 39/464838* (2023.05); *A61P 37/00* (2018.01); *C07K 14/705* (2013.01); *C07K 14/70539* (2013.01); *C12N 5/0636* (2013.01); *C40B 40/02* (2013.01); *G01N 33/566* (2013.01); *G01N 33/68* (2013.01); *A61K 38/00* (2013.01); *C07K 2319/03* (2013.01); *C07K 2319/70* (2013.01); *G01N 2333/7051* (2013.01)

(56) References Cited

U.S. PATENT DOCUMENTS

| | | |
|---|---|---|
| 2004/0137562 A1 | 7/2004 | Gross et al. |
| 2007/0066802 A1 † | 3/2007 | Geiger |
| 2015/0139943 A1 * | 5/2015 | Campana .......... C07K 14/70535 424/85.2 |

FOREIGN PATENT DOCUMENTS

| | | |
|---|---|---|
| WO | WO 2014/127261 | 8/2014 |
| WO | WO 2016/097334 A1 | 6/2016 |
| WO | WO 2016/168773 | 10/2016 |
| WO | WO 2017/070608 | 4/2017 |
| WO | WO 201717332 | * 10/2017 |

OTHER PUBLICATIONS

Liu et al.(MHC Complex: Interaction with Peptides. In: eLS. John Wiley & Sons, Ltd: Chichester, DOI: 10.1002/9780470015902. a0000922.pub2, 2011, pp. 1-12) (Year: 2011).*
Wieczorek et al (Front. Immunol. 2017, vol. 8, article 292: 1-16) (Year: 2017).*
Ali-Khan et al.(Current Protocols in Protein Science, 2002: 22.1.-22.1.19) (Year: 2002).*
Schumacher and Schrieber (Science, 2015, 384 (6230): 69-74) (Year: 2015).*
Celis et al.(PNAS USA, 1994, 91: 2105-2109) (Year: 1994).*
Ochoa-Garay et al.(Mol. Immunol. 1997, 34(3): 273-281) (Year: 1997).*
Shen et al (J. Immunol. 2008, 180: 3601-3611). (Year: 2008).*
Novellino et al (Cancer Immunol. Immunother. 2005, 54: 187-207) (Year: 2005).*
Jackaman et al (Cancer Immunol. Immunother., 2012, 61: 2343-2356) (Year: 2012).*
Ennis et al (Virology, 1999, 259: 256-261) (Year: 1999).*
Aarnoudse et al (Int. J. Cancer, 2002, 99: 7-13) (Year: 2002).*
Hutloff et al (Nature, 1999, 397: 263-266) (Year: 1999).*
Rudolf et al (Clin. Cancer Res., Mar. 2001; 7(3 Suppl): 788s-795s, abstract) (Year: 2001).*
Extended European Search Report and Written Opinion in corresponding European Patent Application No. 18854825.9, dated Mar. 31, 2021 in 9 pages.

Moisini et al., "Redirecting Therapeutic T Cells against Myelin-Specific T Lymphocytes Using a Humanized Myelin Basic Protein-HLA-DR2-3 Chimeric Receptor", The Journal of Immunology, Feb. 21, 2008, vol. 180, No. 5, pp. 3601-3611.
Jyothi et al., "Targeting autoantigen-specific T cells and suppression of autoimmuneencephalomyelitis with receptor-modified T lymphocytes", Nature Biotechnology, Nov. 11, 2002, vol. 20, No. 12, pp. 1215-1220.
Joglekar et al., "T cell antigen discovery via signaling and antigen-presenting bifunctional receptors", Nature Methods, Jan. 28, 2019, vol. 16, No. 2, pp. 191-198.
Nguyen et al., "Identification of a murine CD28 dileucine motif that suppresses single-chain chimeric T-cell receptor expression and function", Blood, Dec. 15, 2003, vol. 102, No. 13, pp. 4320-4325.
Geiger et al., "The TCR ζ-Chain Immunoreceptor Tyrosine-Based Activation Motifs AreSufficient for the Activation and Differentiation of Primary T Lymphocytes", The Journal Of Immunology, Jan. 1, 1999, vol. 162, pp. 5931-5939.
Nguyen et al., "Antigen specific targeting of CD8+ T cells with receptor-modified T lymphocytes", Gene Therapy, Apr. 1, 2003, vol. 10, No. 7, pp. 594-604.
Geiger et al., "Integrated src kinase and costimulatory activity enhances signal transduction through single-chain chimeric receptors in T lymphocytes", Blood, Jan. 15, 2001, vol. 98, No. 8, pp. 2364-2371.
Cole, D. K. et al., "T-cell receptor (TCR)-peptide specificity overridesaffinity-enhancing TCR-major histocompatibility complex interactions", The Journal of Biological Chemistry, Jan. 10, 2014, vol. 289, No. 2, pp. 628-638.
Reiser, J.-B. et al., "Analysis of relationships between peptide/MHCstructural features and naive T cell frequency in humans", The Journal of Immunology, 2014, vol. 193, pp. 5816-5826.
International Search Report of PCT/US2018/049622 dated Dec. 28, 2018 in 5 pages.
Written Opinion of PCT/US2018/049622 dated Dec. 28, 2018 in 7 pages.
Office Action for CN 201880071856.4, issued Nov. 2, 2022, 15 pages.
Office Action for JP 2020-513554, issued Nov. 22, 2022, 14 pages.
Office Action issued in JP 2020-513554 issued Apr. 25, 2023, 10 pages.
Office Action issued in CN 201880071856.4 issued Sep. 16, 2023, 14 pages.
Office Action issued in CN 201880071856.4 issued Dec. 21, 2023, 14 pages.
Zhang, Tong et al., "SING: a novel strategy for identifying tumor-specific, CTL-recognized tumor antigens" The FASEB Journal, Mar. 2004, pp. 600-602, vol. 18, Issue 3.
Office Action for JP 2020-513554 issued May 17, 2022, 13 pages.
Geiger et al., Integrated src kinase and costimulatory activity enhances signal transduction through single-chain chimeric receptors in T lymphocytes, Blood, 2001, 98:2364-2371.†
Jyothi et al., Targeting autoantigen-specific T cells and suppression of autoimmune 2 encephalomyelitis with receptor-modified T lymphocytes, Nat. Biotechnol., 2002, 20:1215-1220.†
Nguyen P. and Geiger T.L., Antigen-specific targeting of CD8+ T cells with receptor-modified T lymphocytes, Gene Therapy, 2003, 10:594-604.†
Margalit et al., Chimeric β2 microglobulin/CD3ζ polypeptides expressed in T cells convert MHC class I peptide ligands into T cell activation receptors: a potential tool for specific targeting of pathogenic CD8+ T cells, International Immunology, 2003, 15(11):1379-1387.†

* cited by examiner
† cited by third party

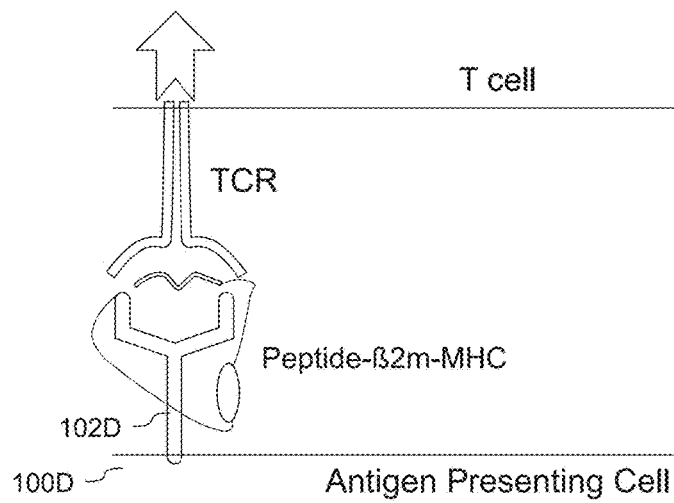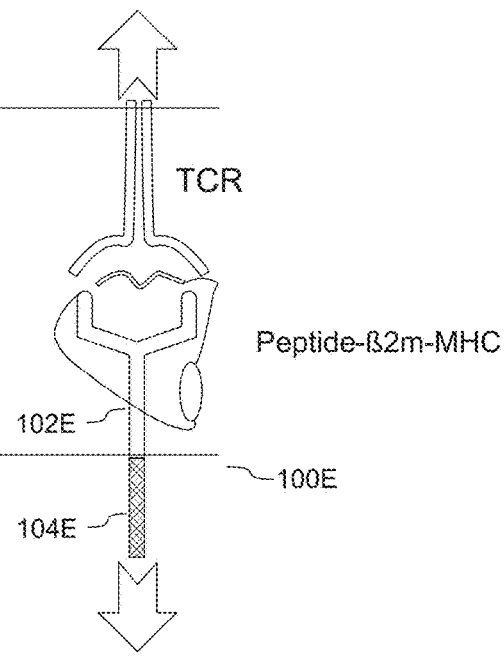

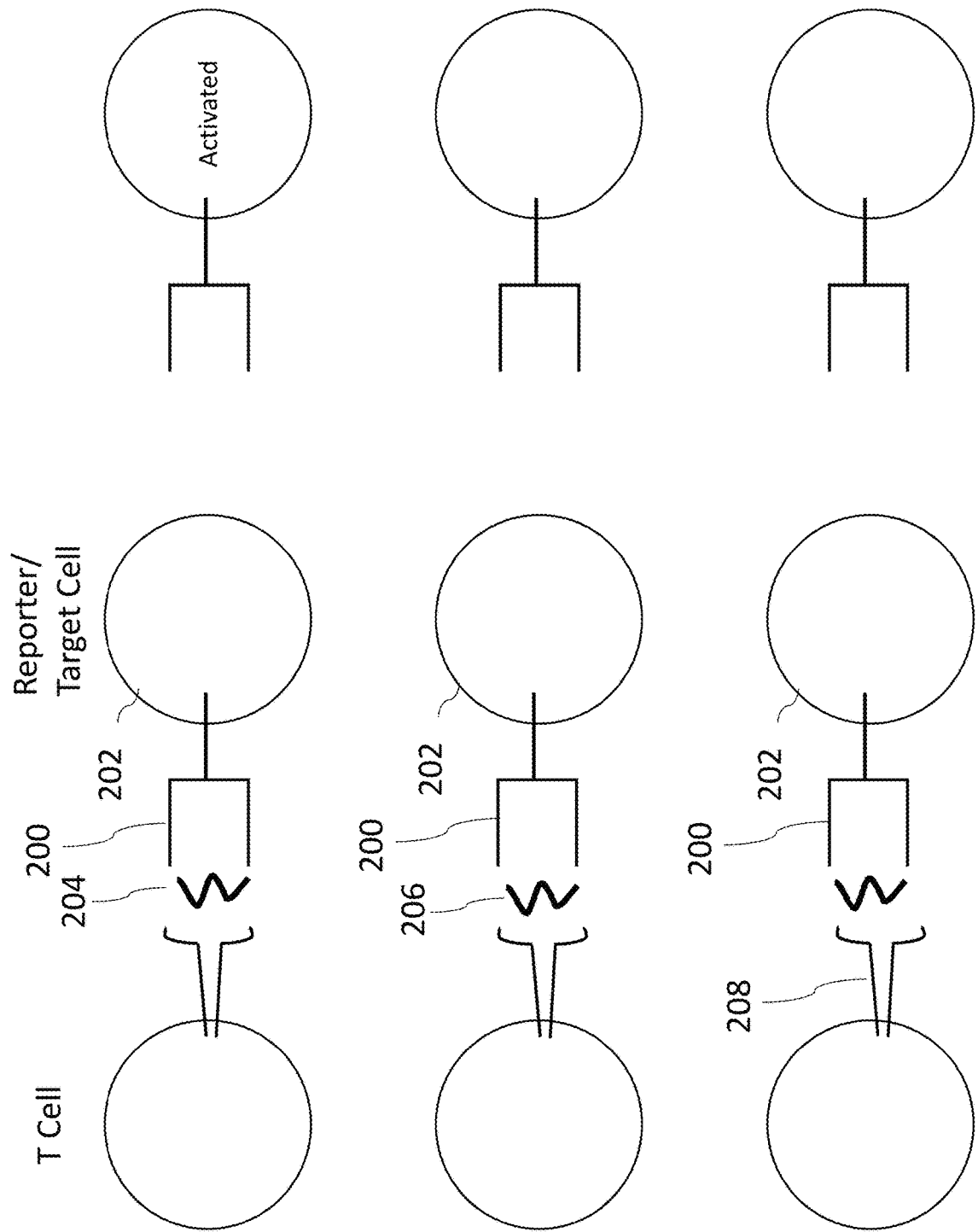

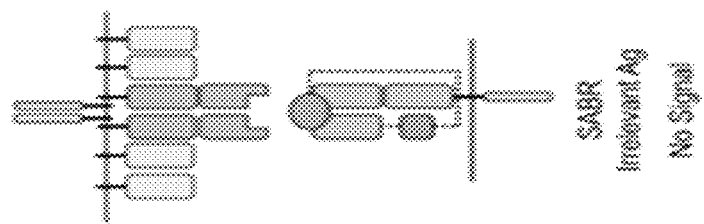
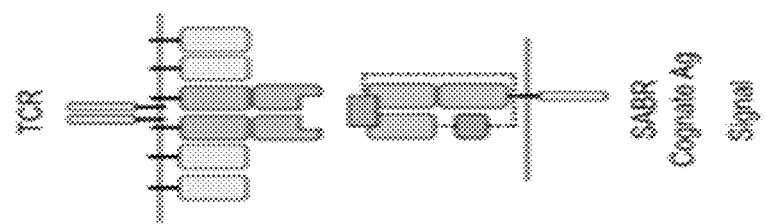
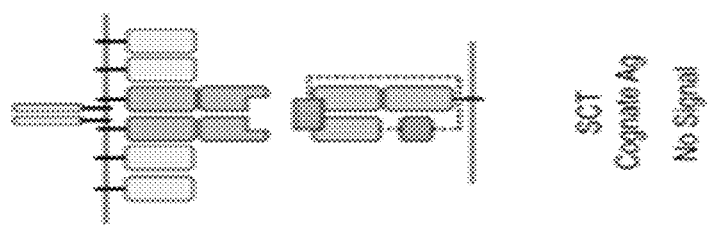
FIG. 7A

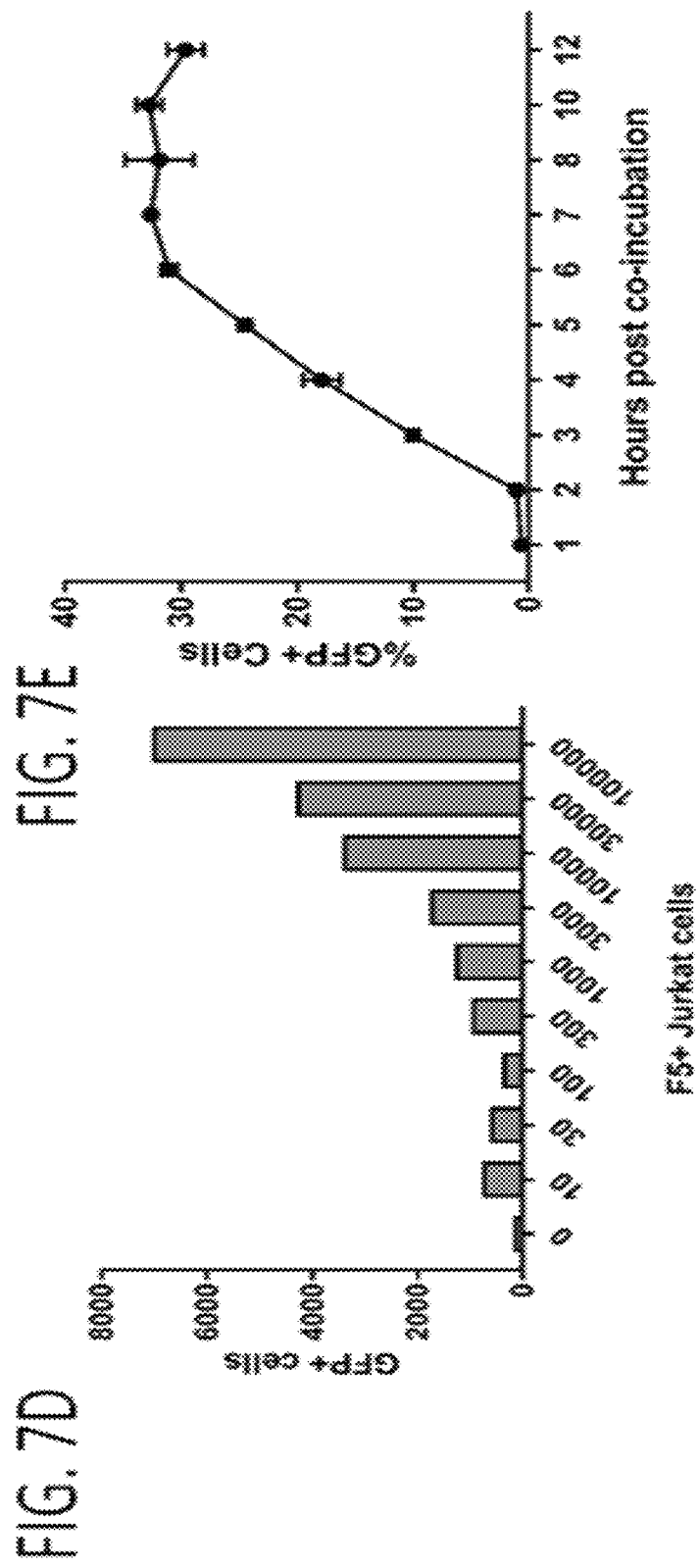

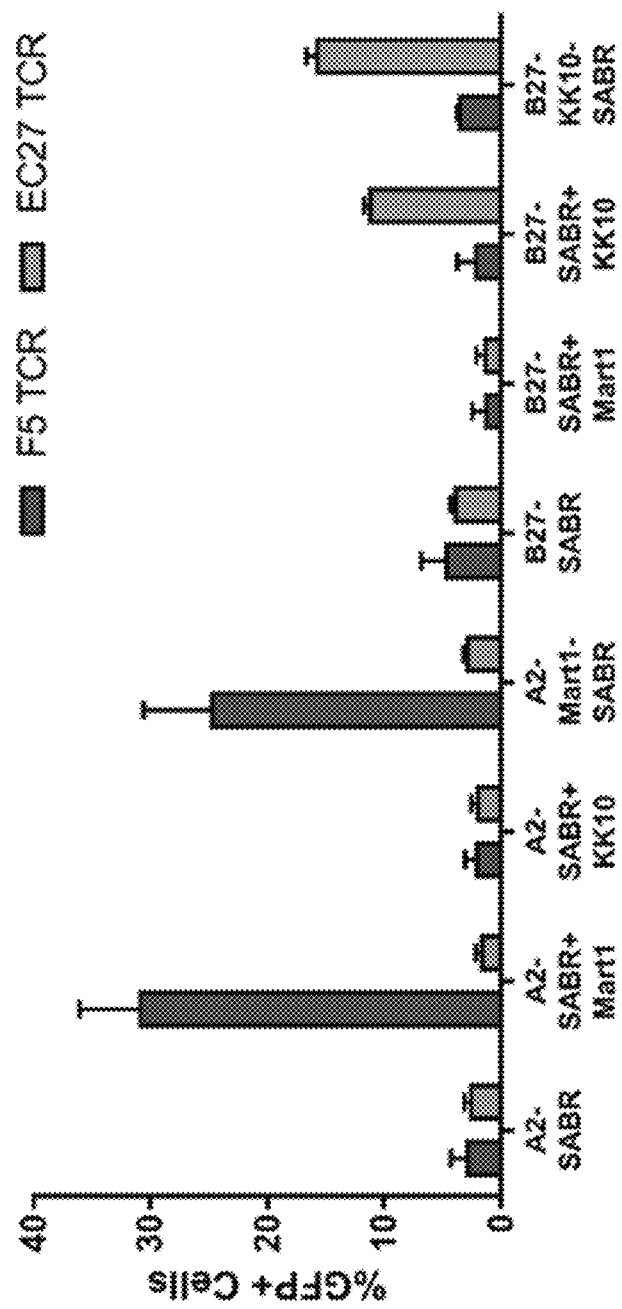
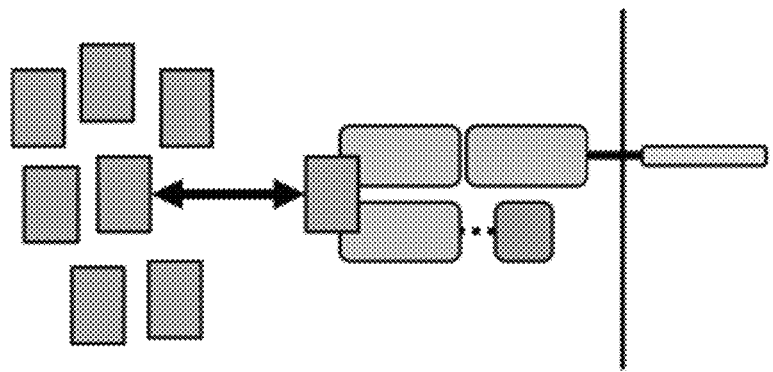
FIG. 8F
FIG. 8E

Cytoplasmic domains from DQA1*03:01 or DQB1*03:02

SABRs Induce Signal Transduction by 4 Hours

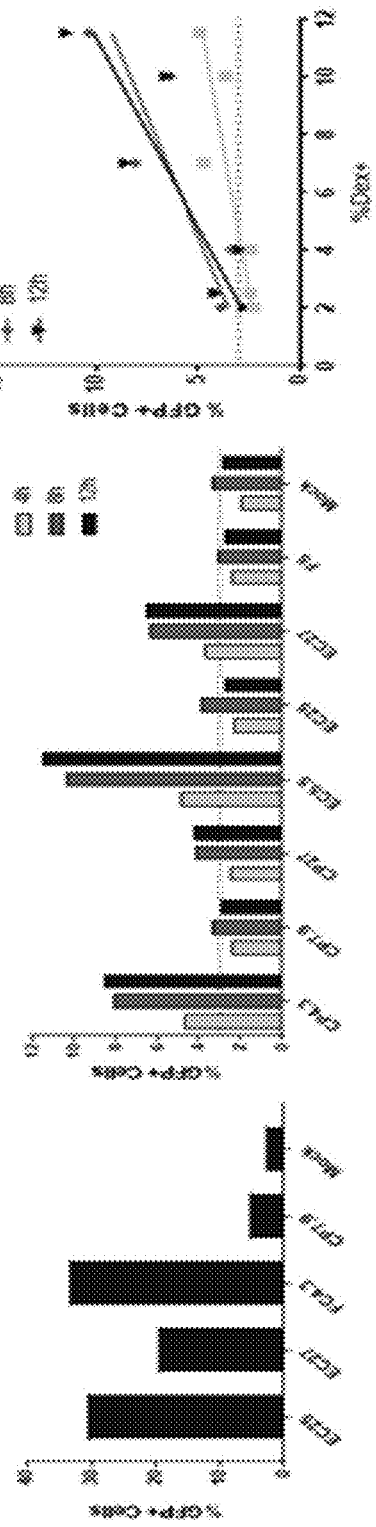
FIG. 18A
FIG. 18B
FIG. 18C

FIG. 19

HLA-A*0201-restricted CD8 T cell epitopes

| Antigen | Epitope | Sequence | Subjects* | |
|---|---|---|---|---|
| Preproinsulin | PPI$_{15-24}$ | ALWGPDPAAA | 14/14 | (SEQ ID NO. 806) |
| Insulin B chain | InsB$_{10-18}$ | HLVEALYLV | 10/13 | (SEQ ID NO. 787) |
| Islet-specific glucose-6-phosphatase catalytic subunit-related protein | IGRP$_{265-273}$ | VLFGLGFAI | 13/12 | (SEQ ID NO. 809) |
| Islet tyrosine phosphatase | IA-2$_{797-805}$ | MVWESGCTV | 11/13 | (SEQ ID NO. 1073) |
| Glutamic acid decarboxylase 65 | GAD65$_{114-123}$ | VMNILLQYVV | 11/10 | (SEQ ID NO. 805) |
| Cytomegalovirus pp65 | CMV pp65$_{495-503}$ | NLVPMVATV | 14/13 | (SEQ ID NO. 464) |
| Epstein-Barr virus BMLF1 | EBV BMLF1$_{280-288}$ | GLCTLVAML | 13/12 | (SEQ ID NO. 192) |

*Numbers of healthy controls/type 1 diabetes patients studied for each epitope specificity.

SIGNALING AND ANTIGEN-PRESENTING BIFUNCTIONAL RECEPTORS (SABR)

CROSS-REFERENCE TO RELATED APPLICATIONS

Any and all applications for which a foreign or domestic priority claim is identified in the Application Data Sheet as filed with the present application are hereby incorporated by reference under 37 CFR 1.57. This application claims the benefit of U.S. Provisional Application 62/554,652 filed on Sep. 6, 2017, which is hereby incorporated by reference in its entirety.

SEQUENCE LISTING STATEMENT

The present application is being filed along with a Sequence Listing in electronic format. The Sequence Listing is provided as a file entitled CALTE132ASEQUENCELIST Jan. 9, 2019, which is 1,950,041 bytes in size, updated by a file entitled CALTE132AREPLACEMENTSEQUENCE-LIST.txt, created on Mar. 18, 2019, which is 1,950,053 bytes in size; further updated by a file entitled CALTE132AREPLACEMENTSEQUENCELIST2.txt, created on Jun. 2, 2020, which is 1,950,207 bytes in size; and further updated by a file entitled CALTE132AREPLACEMENTSEQUENCE3.txt, created on Oct. 18, 2021, which is 1,950,172 bytes in size. The information in the electronic format of the Sequence Listing is incorporated herein by reference in its entirety.

BACKGROUND

Field

Embodiments described herein relate generally to molecules for immunological use and treatment.

Description

T cells are an integral part of the immune response to pathogens and cancers. T cells respond to specific antigenic epitopes presented on major histocompatibility complex (MHC) molecules on their target cells. Antigen recognition by T cells is mediated by their T cell receptor (TCR), which triggers an intracellular signal leading to T cell activation followed by a functional response. However, MHC molecules that present antigens lack signaling domains, and hence cannot induce a response in the target cells. Therefore, the TCR-Antigen-MHC interaction results in a unidirectional signal towards the T cell. Lack of signaling towards the target cells is a major limitation in the potential use of TCR-Antigen-MHC interactions for various functions. Thus, new, scalable techniques and molecules that expand the utilization of TCR-Antigen-MHC interactions are needed.

SUMMARY

Some embodiments herein relate to a signaling and antigen-presenting bifunctional receptor (SABR) comprising: an antigen presenting domain, and a signal transduction domain, wherein the antigen presenting domain comprises a binding fragment of a MHC molecule.

Some embodiments herein relate to a SABR, wherein the antigen presenting domain comprises a MHC.

Some embodiments herein relate to a nucleic acid encoding for a SABR.

Some embodiments herein relate to a cell comprising the nucleic acid encoding for a SABR.

Some embodiments herein relate to a SABR, wherein the MHC comprises a Class I MHC.

Some embodiments herein relate to a SABR, wherein the MHC comprises a Class II MHC.

Some embodiments herein relate to a SABR, further comprising a peptide, wherein the peptide comprises an epitope, wherein the peptide epitope is covalently linked to the SABR, and wherein the antigen presenting domain binds to the peptide.

Some embodiments herein relate to a SABR, wherein the signal transduction domain comprises a T cell signaling domain.

Some embodiments herein relate to a SABR, wherein the signal transduction domain is derived from a cytokine receptor, wherein the cytokine receptor comprises IL2, IL4, EPO, GM-CSF, JAK-STAT, CCL10, a G protein coupled receptor, or a receptor of the TNF Receptor superfamily.

Some embodiments herein relate to a SABR, wherein the signal transduction domain comprises 4-1BB (CD137), CD28, CD27, DAP10, ICOS, OX40, PD1, CTLA4, TIM3, CD3zeta, Notch, synNotch, chemical-induced dimerization, CD79A, CD79B, CD72, CD22, CD5, CD19, CD45, IL2, IL4, EPO, GM-CSF, JAK-STAT, CCL10, a G protein coupled receptor, a receptor of the TNF receptor superfamily, a NK cell receptor, a Fc receptor, a toll-like receptor, a RIG-I-like receptor, or a NOD-like receptors.

Some embodiments herein relate to a SABR, further comprising a transmembrane domain.

Some embodiments herein relate to a SABR, wherein the transmembrane domain comprises a transmembrane domain from one or more of 4-1BB (CD137), CD28, CD27, DAP10, ICOS, OX40, PD1, CTLA4, TIM3, CD3zeta, Notch, synNotch, chemical-induced dimerization, CD79A, CD79B, CD72, CD22, CD5, CD19, CD45, IL2, IL4, EPO, GM-CSF, JAK-STAT, CCL10, a G protein coupled receptor, a receptor of the TNF Receptor superfamily, a NK cell receptor, a Fc receptor, a toll-like receptor, a RIG-I-like receptor, a NOD-like receptor, or an MHC molecule.

Some embodiments herein relate to a SABR, wherein the transmembrane domain comprises any one or more of the transmembrane domains of Tables 0.1, 0.2, or 0.3 (as appropriate).

Some embodiments herein relate to a SABR, wherein the antigen presenting domain comprises any one or more of the antigen presenting domains of Tables 0.1, 0.2, or 0.3 (as appropriate).

Some embodiments herein relate to a SABR, wherein the signal transduction domain comprises any one or more of the signal transduction domains of Tables 0.1, 0.2, or 0.3 (as appropriate).

Some embodiments herein relate to a SABR, wherein the antigen presenting domain is fused to the signal transduction domain.

Some embodiments herein relate to a SABR, further comprising one or more linkers.

Some embodiments herein relate to a cell comprising: an extracellular peptide-MHC complex comprising: an antigen presenting domain linked to a signal transduction domain, wherein the antigen presenting domain comprises an MHC molecule.

Some embodiments herein relate to a cell, wherein the cell comprises any one or more of the SABRs described herein.

Some embodiments herein relate to an isolated nucleic acid molecule comprising a nucleotide sequence encoding any one of the SABRs described herein.

Some embodiments herein relate to a method for preparing a signaling cell, the method comprising: providing a target cell, and introducing into the target cell a nucleic acid molecule comprising a nucleotide sequence coding for a SABR directed against at least one TCR expressed at the surface of a T cell, wherein the SABR comprises a MHC linked to a signal transduction domain.

Some embodiments herein relate to a method for antigen discovery, the method comprising: expressing any of the SABRs described herein in at least one reporter cell, wherein the at least one reporter cell produces a measurable signal upon a signal transduction event that occurs upon binding of an antigen receptor to the antigen presenting domain, incubating the at least one reporter cell with the antigen receptor to be tested for binding to the SABR, detecting a presence of the measurable signal in the at least one reporter cell when the antigen receptor binds, and identifying the at least one reporter cell producing the measurable signal, thereby identifying an antigen by associating the SABR in the cell with the reporter, with the antigen receptor.

Some embodiments herein relate to a method for antigen discovery, wherein the antigen receptor comprises a soluble molecule.

Some embodiments herein relate to a method for antigen discovery, wherein the soluble molecule comprises an antibody.

Some embodiments herein relate to a method for antigen discovery, wherein the antigen receptor is expressed on a cell.

Some embodiments herein relate to a method for antigen discovery, wherein the antigen receptor comprises a TCR expressed on a T cell.

Some embodiments herein relate to a method for antigen discovery, wherein the at least one reporter cell comprises a library of cells, wherein the library of cells have numerous different SABRs, and wherein the numerous different SABRs can bind to different antigen receptors.

Some embodiments herein relate to a method for antigen discovery, wherein the antigen receptor comprises numerous antigen receptors.

Some embodiments herein relate to a method for antigen discovery, wherein numerous different SABRs are expressed and one determines which SABR a particular antigen receptor binds to by monitoring the measurable signal and identifying which SABR is in the cell that exhibited the measurable signal.

Some embodiments herein relate to a method for antigen discovery, wherein more than one antigen receptor is present and one determines which antigen receptor binds to a particular SABR.

Some embodiments herein relate to a method for antigen discovery, wherein more than one antigen receptor and more than one SABR are present.

Some embodiments herein relate to a method for antigen discovery, wherein the at least one reporter cell comprises NFAT-GFP-Jurkat cells.

Some embodiments herein relate to a method for antigen discovery, wherein the measurable signal comes from expression of a detectable marker.

Some embodiments herein relate to a method for antigen discovery, wherein the reporter cells expressing the measurable signal are identified using flow cytometry.

Some embodiments herein relate to a method for antigen discovery, wherein the antigen receptor comprises an expressed orphan TCR.

Some embodiments herein relate to a method for antigen discovery, wherein the one or more reporter cells expresses a genetically encoded antigen or antigenic epitope.

Some embodiments herein relate to a method for antigen discovery, further comprising identifying the genetically encoded antigen or antigenic epitope by DNA sequencing.

Some embodiments herein relate to a library comprising: any of the SABRs described herein, and at least one candidate antigen receptor.

Some embodiments herein relate to a library, wherein the at least one antigen receptor is expressed on a cell, wherein the cell is an antigen receptor cell.

Some embodiments herein relate to a library, wherein the SABR is expressed on a reporter cell, such that the cell provides a detectable marker upon binding of the SABR to the antigen receptor.

Some embodiments herein relate to a library, wherein the reporter cell comprises NFAT-GFP-Jurkat cells.

Some embodiments herein relate to a library, wherein the antigen receptor cell comprises T cells comprising TCR.

Some embodiments herein relate to a library, wherein the antigen receptor cell comprises a cell expressing orphan TCR.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject.

Some embodiments herein relate to a method for initiating a therapeutic response, wherein the cellular response results in one or more of: cell mediated cytotoxicity, release of inflammatory cytokines, release of suppressive cytokines, direct suppression of target cells, release of anti-inflammatory cytokines, induction of pro-proliferative signals, induction of anti-proliferative signals, induction of apoptosis, induction of cell exhaustion markers, and direct target cell activation.

Some embodiments herein relate to a method for initiating a therapeutic response, wherein the therapeutic cell destroys a pathogenic T cell.

Some embodiments herein relate to a method for initiating a therapeutic response wherein the therapeutic cell activates a target T cell.

Some embodiments herein relate to a method for initiating a therapeutic response, wherein the therapeutic cell suppresses a pathogenic T cell.

Some embodiments herein relate to a composition comprising: a therapeutic T-cell comprising any of the SABRs described herein.

Some embodiments herein relate to a method for treating a patient comprising introducing into the patient a therapeutic T cell comprising an extracellular peptide-MHC complex, the peptide-MHC complex comprising an antigen presenting domain linked to a signal transduction domain, wherein the antigen presenting domain comprises an MHC.

Some embodiments herein relate to a SABR comprising: an extracellular binding domain comprising an MHC and a peptide epitope, a transmembrane domain, and a cytoplasmic signaling domain.

BRIEF DESCRIPTION OF THE DRAWINGS

FIG. 1D illustrates a typical antigen presenting cell with an antigen presenting domain but no transduction signaling domain.

FIG. 1E illustrates an antigen presenting cell with a SABR comprising both an antigen presenting domain and a transduction signaling domain capable of signal induction within an antigen presenting cell.

FIG. 2A illustrates a schematic describing a use of SABRs in a reporter cell line that expresses a signal upon TCR binding or recognition according to various embodiments herein.

FIG. 7A illustrates schematics demonstrating SABRs and TCR-pMHC specific signaling.

FIG. 7D illustrates a graph of detection of low cell numbers by SABRs.

FIG. 7E illustrates a timecourse of GFP expression by A2-MART1-SABR transduced NFAT-GFP-Jurkat cells co-cultured with F5-transduced Jurkat cells.

FIG. 8E illustrates a schematic of empty SABRs pulsed with exogenous peptide.

FIG. 8F illustrates a graph showing GFP expression by NFAT-GFP-Jurkats transduced with empty SABRs pulsed with soluble MART1 or KK10 peptides and co-cultured with Jurkat cells transduced with F5 or EC27 TCRs.

FIG. 18A illustrates a bar graph depicting the frequency of % GFP+ for TCR-transduced Jurkat cells incubated with SCTR-transduced NFAT-GFP-Jurkat cells.

FIG. 18B illustrates a bar graph depicting the frequency of % GFP+ for TCR-transduced PBMCs incubated with SCTR-transduced NFAT-GFP-Jurkat cells.

FIG. 18C illustrates a line graph depicting the frequency over time of % GFP+ for TCR-transduced PBMCs incubated with SCTR-transduced NFAT-GFP-Jurkat cells.

FIG. 19 illustrates examples of antigenic epitopes according to various embodiments herein (e.g., for the treatment of diabetes).

DETAILED DESCRIPTION

Figure 1A:
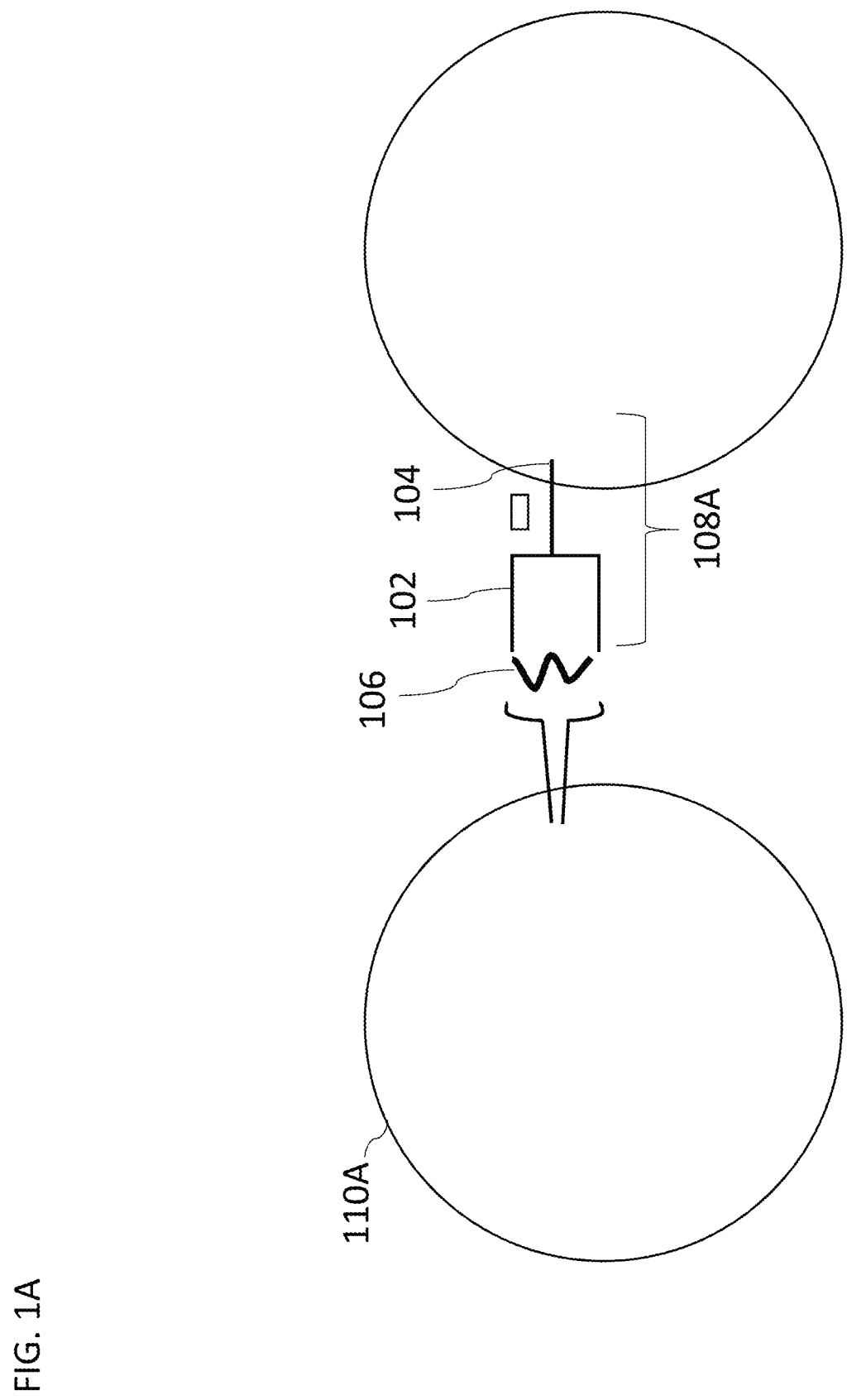
FIG. 1A illustrates an example SABR construct with CD8+ T cells according to various embodiments herein.

MHC molecules that present antigens lack signaling domains, and hence cannot induce a response in the target cells. Therefore, a TCR-Antigen-MHC interaction results in a unidirectional signal towards the T cell. Lack of signaling towards the target cells is a major limitation in the potential use of TCR-Antigen-MHC interactions for various functions. Thus, new, scalable techniques and molecules that expand the utilization of TCR-Antigen-MHC interactions are needed and are provided herein (in some embodiments).

Described herein are compositions and methods for signaling and antigen-presenting bifunctional receptors (SA-BRs) comprising: one or more antigen presenting domains, and one or more signal transduction domains, wherein the one or more antigen presenting domains comprise a binding fragment of a major histocompatibility complex (MHC) molecule. Various immunological functions of the SABRs are also described. Various uses and functions of the SABRs are provided herein. For example, in some embodiments, the SABRs described herein may be used for antigen discovery, for suppressing and/or destroying pathogenic T cells, for initiating therapeutic responses, in methods of treatment, for construction of SABR libraries, for neoantigen discovery, as well as other uses.

Definitions and Various Embodiments

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2$^{nd}$ ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below. It is to be understood that both the foregoing general description and the following detailed description. are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, an "antigen presenting domain" refers to an extracellular domain that functions to present antigen peptide fragments to T cells responsible for cell-mediated immune responses.

As used herein, a "signal transduction domain" refers to any domain that can transmit an extracellular signal intracellularly.

As used herein, a "major histocompatibility molecule" (MHC) refers to a set of cell surface proteins essential for the acquired immune system to recognize foreign molecules. Unless otherwise noted, MHC refers to both Class I MHC and Class II MHC.

As used herein, "peptide" refers to a chain of amino acids linked to each other by peptide bonds.

As used herein, "epitope" refers to a part of an antigen that is recognized by the immune system. This can be by, for example, antibodies, B cells, or T cells.

As used herein, "T cell signaling domain" refers to a cytoplasmic T cell domain that functions to transmit an intracellular signal.

As used herein, "cytokine receptor" refers to any receptor that bind cytokines.

As used herein, "transmembrane domain" refers to an amino acid sequence that traverses and is present in the cell membrane.

As used herein, a "linker" refers to a peptide sequence occurring between protein domains.

As used herein, a "signaling cell" refers to any cell any cell that is capable for transmitting an extracellular signal intracellularly through a signaling domain.

As used herein, a "target cell" refers to a cell that bears receptors recognized by a signaling molecule.

As used herein, a "reporter cell" refers to a cell expressing reporter genes, which, when exposed to a stimulus, induces a measurable signal activity that can be readily assessed qualitatively and quantitatively.

As used herein, a "measurable signal" refers to any reporter activity that can be assessed qualitatively or quantitatively.

As used herein, "antigen discovery" refers to the process of discovering the antigens targeted by T cell responses.

As used herein, a "soluble molecule" refers to a compound soluble in a liquid.

As used herein, a "library" refers to a collection of cells having one or more signaling molecules.

As used herein, a "detectable marker" refers to any discernable characteristic in response to signal transduction.

As used herein, "flow cytometry" refers to a laser- or impedance-based, biophysical technology employed in cell counting, cell sorting, biomarker detection and protein engineering, by suspending cells in a stream of fluid and passing them through an electronic detection apparatus.

As used herein, a "therapeutic cell" refers to a cell transduced with a SABR, wherein the SABR directs a cellular response in a subject upon binding to an antigen receptor in the subject.

As used herein, a "cellular response" refers to any biochemical reaction within a cell in response to a received signal.

As used herein, a "pathogenic T cell" refers to any T cell that causes or contributes to a disease, for example, in an autoimmune disease.

As used herein, a "cytoplasmic domain" refers to amino acid sequences within the cytoplasm of a cell.

As used herein, a "vector," interchangeably referred to as a transgenic construct, a targeting construct, or simply a construct, is a nucleic acid. As used herein, "nucleic acid" refers to deoxyribonucleic acid (DNA). In some embodiments, nucleic acid may refer to ribonucleic acid (RNA). In some embodiments, the construct as provided herein comprise one or more regulatory elements. Exemplary regulatory elements in prokaryotes include promoters, operators and ribosome binding sites. Regulatory elements that are used in eukaryotic cells can include, without limitation, transcriptional and translational control sequences, such as promoters, terminators, enhancers, insulators, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell. For example, a promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions (for example, a change in temperature). "Treating" or "treatment" of a condition may refer to preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21.sup.st Edition, Univ. of Sciences in Philadelphia (USIP), Lippincott Williams & Wilkins, Philadelphia, Pa., 2005.

The term "antibody" includes, but is not limited to, genetically engineered or otherwise modified forms of immunoglobulins, such as intrabodies, chimeric antibodies, fully human antibodies, humanized antibodies, antibody fragments, and heteroconjugate antibodies (e.g., bispecific antibodies, diabodies, triabodies, tetrabodies, etc.). The term "antibody" includes cys-diabodies and minibodies. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full-length antibody can be composed of two identical pairs of polypeptide chains, each pair having one "light" and one "heavy" chain (connected through a disulfide bond. The recognized immunoglobulin genes include the kappa, lambda, alpha, gamma, delta, epsilon, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same binding specificity. In some embodiments, the antibody binds specifically to a desired target.

The term "isolated," when applied to a nucleic acid or protein, denotes that the nucleic acid or protein is essentially free of other cellular components with which it is associated in the natural state. In some embodiments, it can be in either a dry or aqueous solution. Purity and homogeneity can be determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. In some embodiments, this can denote that the nucleic acid or protein is at least 85% pure, more preferably at least 95% pure, and most preferably at least 99% pure of molecules that are present under in vivo conditions.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an alpha.-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Signaling and Antigen-Presenting Bifunctional Receptors

Some embodiments provided herein relate to a signaling and antigen-presenting bifunctional receptor (SABR) comprising: an antigen presenting domain, and a signal transduction domain. The antigen presenting domain comprises a binding fragment of a major histocompatibility complex (MHC) molecule. In some embodiments, the SABRs herein allow transduction of a signal within a target cell, which has various application as describe herein. Some embodiments provided herein relate to a SABR comprising: one or more antigen presenting domains, and a signal transduction domain, wherein the one or more antigen presenting domains comprise a binding fragment of a MHC molecule. Some embodiments provided herein relate to a SABR comprising: an antigen presenting domain, and one or more signal transduction domains, wherein the antigen presenting domain comprises a binding fragment of a MHC molecule. Some embodiments provided herein relate to a SABR comprising: one or more antigen presenting domains, and one or more signal transduction domains, wherein the one or more antigen presenting domains comprises a binding fragment of a MHC molecule.

Figure 1B:
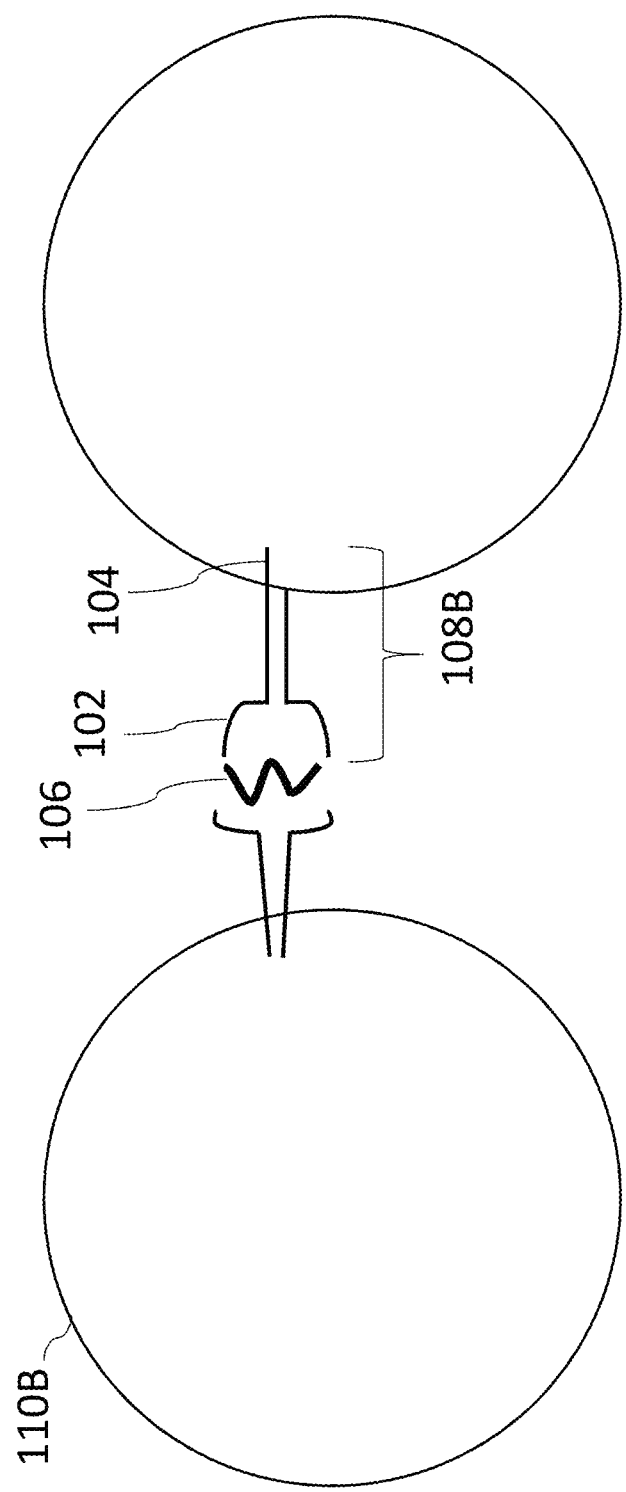
FIG. 1B illustrates an example SABR construct with CD4+ T cells according to various embodiments herein.

FIG. 1A illustrates an example SABR construct with CD8+ T cells according to various embodiments herein. FIG. 1B illustrates an example SABR construct with CD4+ T cells according to various embodiments herein. In some embodiments, SABRs are constructed by linking two parts: antigen-presenting domains 102 and signal transduction domains 104. Antigen presentation to a T cell is dependent on class I and class II MHC molecules, which present peptide epitopes 106 to T cells. Class I MHC molecules 108A usually present 8-11aa long peptide epitopes to CD8+ T cells 110A, whereas Class II MHC 108B usually molecules present 12-15aa long peptide epitopes to CD4+ T cells 110B. In some embodiments, SABRs are created by linking antigen presenting domains 102 to signal transduction domains 104.

Figure 1C:
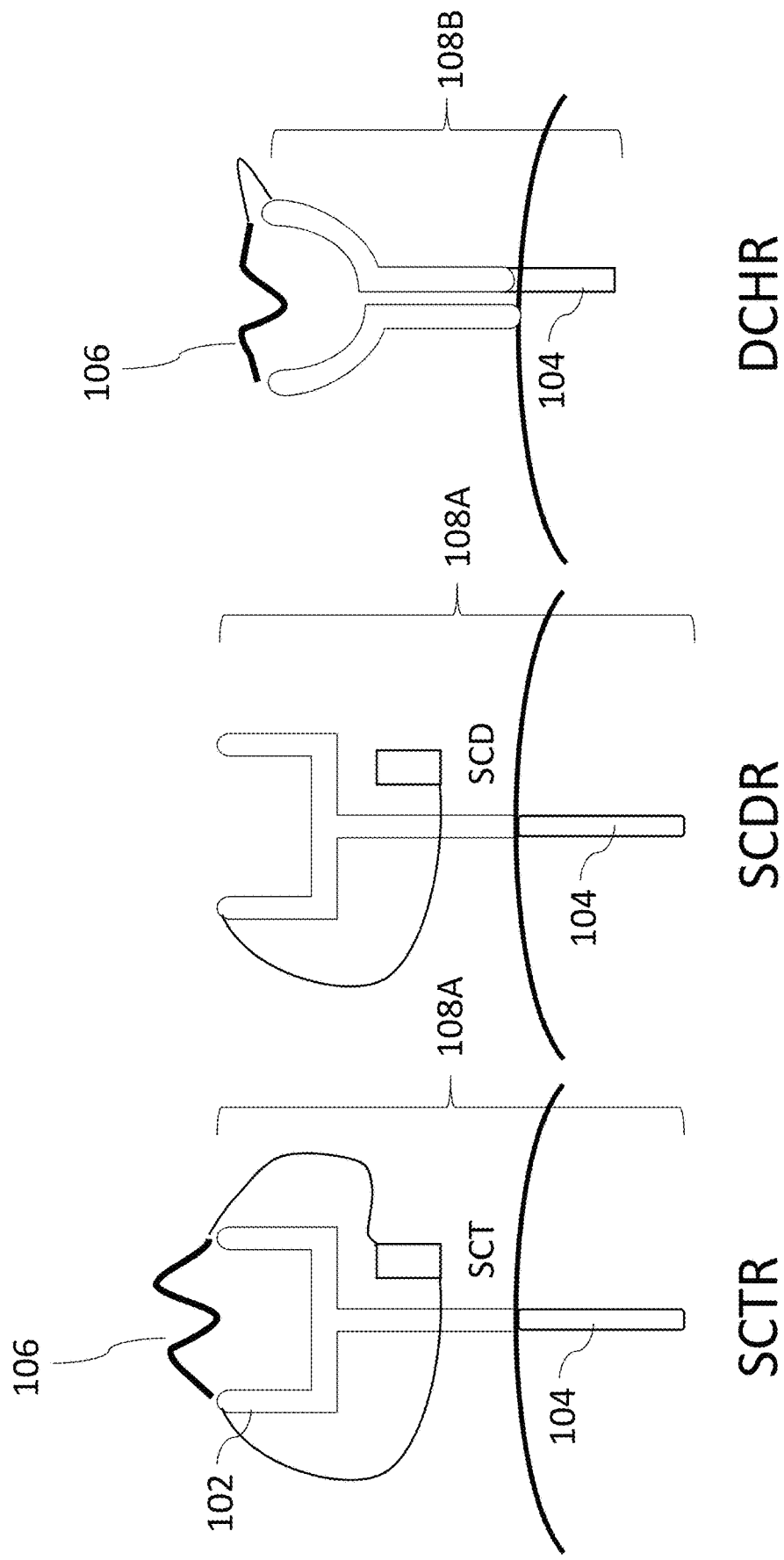
FIG. 1C illustrates SABR constructs according to various embodiments herein.

FIG. 1C illustrates SABR constructs according to various embodiments herein. In some embodiments, the antigen presenting domains 102 can be a class I MHC molecule 108A with covalently linked peptide 106 (SCTRs), or class I MHC molecule 108A without any peptide epitope (SCDRs), or a class II MHC molecules 108B with covalently linked peptide 106 (DCHR). In some embodiments, the signaling domains 104 can be derived from TCR-CD3 signaling domains similar to those used in chimeric antigen receptors (CARs), from cytokine receptors, or from other receptors that signal upon multimerization. In some embodiments, SABR-libraries can be constructed either by covalently linking the antigenic epitope or expressing the antigenic protein/epitope in SABR-expressing cells.

FIG. 1D illustrates a typical antigen presenting cell 100D with an antigen presenting domain 102D but no transduction signaling domain. FIG. 1E illustrates an antigen presenting cell 100E with a SABR comprising both an antigen presenting domain 102E and a transduction signaling domain 104E capable of signal induction within the antigen presenting cell 100E.

Some embodiments provided herein relate to a SABR comprising: an antigen presenting domain, and a signal transduction domain, wherein the antigen presenting domain comprises a binding fragment of a MHC molecule, and wherein the antigen presenting domain comprises a MHC.

Some embodiments provided herein relate to a nucleic acid encoding for any of the SABRs described herein. Some embodiments provided herein relate to a nucleic acid encoding for a SABR comprising: an antigen presenting domain, and a signal transduction domain, wherein the antigen presenting domain comprises a binding fragment of a MHC molecule.

Some embodiments provided herein relate to a cell comprising a nucleic acid encoding for any of the SABRs described herein. Some embodiments provided herein relate to a nucleic acid encoding for a SABR comprising: an antigen presenting domain, and a signal transduction domain, wherein the antigen presenting domain comprises a binding fragment of a MHC molecule.

Some embodiments provided herein relate to a SABR comprising: an antigen presenting domain, and a signal transduction domain, wherein the antigen presenting domain comprises a binding fragment of a MHC molecule, and wherein the MHC comprises a Class I MHC.

Some embodiments provided herein relate to a SABR comprising: an antigen presenting domain, and a signal transduction domain, wherein the antigen presenting domain comprises a binding fragment of a MHC molecule, and wherein the MHC comprises a Class II MHC.

Some embodiments provided herein relate to any of the SABRs described herein, further comprising a peptide. Some embodiments provided herein relate to a SABR comprising: an antigen presenting domain, a signal transduction domain, wherein the antigen presenting domain comprises a binding fragment of a MHC molecule, and a peptide. Some embodiments provided herein relate to a SABR wherein the peptide comprises an epitope. In some embodiments, any of the epitopes in tables 6.3 or 6.4 can be employed. Some embodiments provided herein relate to a SABR comprising: an antigen presenting domain, a signal transduction domain, wherein the antigen presenting domain comprises a binding fragment of a MHC molecule, and a peptide, wherein the peptide comprises an epitope, and wherein the peptide epitope is covalently linked to the SABR. Some embodiments provided herein relate to a SABR comprising: an antigen presenting domain, a signal transduction domain, wherein the antigen presenting domain comprises a binding fragment of a MHC molecule, and a peptide, wherein the peptide comprises an epitope, wherein the peptide epitope is covalently linked to the SABR, and wherein the antigen presenting domain binds to the peptide. Some embodiments provided herein relate to a SABR comprising: an antigen presenting domain, a signal transduction domain, wherein the antigen presenting domain comprises a binding fragment of a MHC molecule, and a peptide, wherein the peptide comprises an epitope, wherein the peptide epitope is covalently linked to the SABR, and wherein the antigen presenting domain does not bind to the peptide.

Some embodiments provided herein relate to a SABR comprising: an antigen presenting domain, and a signal transduction domain, wherein the antigen presenting domain comprises a binding fragment of a MHC molecule, and wherein the signal transduction domain comprises a T cell signaling domain. Some embodiments provided herein relate to a SABR comprising: an antigen presenting domain, and a signal transduction domain, wherein the antigen presenting domain comprises a binding fragment of a MHC molecule. Some embodiments provided herein relate to a SABR wherein the signal transduction domain comprises a T cell signaling domain. Some embodiments provided herein relate to a SABR wherein the T cell signaling domain comprises 4-1BB (CD137), CD28, CD27, DAP10, ICOS, OX40, PD1, CTLA4, TIM3, or CD3zeta. Some embodiments provided herein relate to a SABR comprising: an antigen presenting domain, and a signal transduction domain, wherein the antigen presenting domain comprises a binding fragment of a MHC molecule, wherein the signal transduction domain comprises a T cell signaling domain, and wherein the T cell signaling domain comprises PMID: 23667569, PMID: 22437870, PMID: 23667569, PMID: 22437870, PMID: 23667569, PMID: 22437870, PMID: 23667569, PMID: 22437870, PMID: 23667569, PMID: 22437870, PMID: 23667569, or PMID: 22437870. Some embodiments provided herein relate to a SABR comprising: an antigen presenting domain, and a signal transduction domain, wherein the antigen presenting domain comprises a binding fragment of a MHC molecule, wherein the signal transduction domain comprises a T cell signaling domain. Some embodiments provided herein relate to a SABR wherein the T cell signaling domain comprises one or more of the domains of Table 0.1. In some embodiments, fragments of one or more of the following items in Table 0.1 can also be employed.

TABLE 0.1

| Domain | Class/Source | Function | Ref |
|---|---|---|---|
| 4-1BB (CD137) | T cell signaling | Antigen discovery, Fratricide Immunotherapy, Tolerogenic Immunotherapy | PMID: 23667569, PMID: 22437870 |
| CD28 | T cell signaling | Antigen discovery, Fratricide Immunotherapy, Tolerogenic Immunotherapy | PMID: 23667569, PMID: 22437870 |
| CD27 | T cell signaling | Antigen discovery, Fratricide Immunotherapy, Tolerogenic Immunotherapy | PMID: 23667569, PMID: 22437870 |
| DAP10 | T cell signaling | Antigen discovery, Fratricide Immunotherapy, Tolerogenic Immunotherapy | PMID: 23667569, PMID: 22437870 |
| ICOS, OX40, PD1, CTLA4, TIM3 | T cell signaling | Antigen discovery, Fratricide Immunotherapy, Tolerogenic Immunotherapy, Modulating exhaustion | PMID: 23667569, PMID: 22437870 |
| CD3zeta | T cell signaling | Antigen discovery, Fratricide Immunotherapy, Tolerogenic Immunotherapy | PMID: 23667569, PMID: 22437870 |

Some embodiments provided herein relate to a SABR comprising: an antigen presenting domain, and a signal transduction domain, wherein the antigen presenting domain comprises a binding fragment of a MHC molecule. Some embodiments provided herein relate to a SABR wherein the signal transduction domain is derived from a cytokine receptor. Some embodiments provided herein relate to a SABR comprising: an antigen presenting domain, and a signal transduction domain, wherein the antigen presenting domain comprises a binding fragment of a MHC molecule, wherein the signal transduction domain is derived from a cytokine receptor. Some embodiments provided herein relate to a SABR wherein the cytokine receptor comprises IL2, IL4, EPO, GM-CSF, JAK-STAT, CCL10, a G protein coupled receptor, or a receptor of the TNF Receptor superfamily. Some embodiments provided herein relate to a SABR wherein the signal transduction domain is derived from a cytokine receptor, wherein the cytokine receptor comprises PMID: 17934481, PMID: 10808165, PMID: 27317733, PMID: 17934481, PMID: 10808165, PMID: 27317733, PMID: 24679437, PMID: 24679437, PMID: 19239902. Some embodiments provided herein relate to a SABR wherein the cytokine receptor comprises one or more of the domains of Table 0.2. In some embodiments, a fragment of the cytokine receptor can be employed.

TABLE 0.2

| Domain | Class/Source | Function | Ref |
|---|---|---|---|
| Cytokines such as IL2, IL4, EPO, GM-CSF | Cytokine signaling | Tolerogenic Immunotherapy, Immunomodulation, Vaccine boost | PMID: 17934481; PMID: 10808165; PMID: 27317733 |
| JAK-STAT | Cytokine signaling | Tolerogenic Immunotherapy, Immunomodulation, Vaccine boost | PMID: 17934481; PMID: 10808165; PMID: 27317733 |
| Chemokines such as CCL10 | Cytokine signaling | Tolerogenic Immunotherapy, Immunomodulation, Vaccine boost | PMID: 24679437 |
| G protein coupled receptors | Cytokine signaling | Tolerogenic Immunotherapy, Immunomodulation, Vaccine boost | PMID: 24679437 |
| TNF Receptor superfamily | Cytokine signaling | Immunomodulation, Vaccine boost | PMID: 19239902 |

Some embodiments provided herein relate to a SABR wherein the signal transduction domain comprises 4-1BB (CD137), CD28, CD27, DAP10, ICOS, OX40, PD1, CTLA4, TIM3, CD3zeta, Notch, synNotch, chemical-induced dimerization, CD79A, CD79B, CD72, CD22, CD5, CD19, CD45, IL2, IL4, EPO, GM-CSF, JAK-STAT, CCL10, a G protein coupled receptor, a receptor of the TNF Receptor superfamily, a NK cell receptor, a Fc receptor, a toll-like receptor, a RIG-I-like receptor, or a NOD-like receptor. Some embodiments provided herein relate to a SABR comprising: an antigen presenting domain, and a signal transduction domain, wherein the antigen presenting domain comprises a binding fragment of a MHC molecule, and wherein the signal transduction domain comprises PMID: 23667569, PMID: 22437870, PMID: 23667569, PMID: 22437870, PMID: 23667569, PMID: 22437870, PMID: 23667569, PMID: 22437870, PMID: 23667569, PMID: 22437870, PMID: 26830878, U.S. Pat. No. 9,670,281, PMID: 26431673, PMID: 21816833, PMID: 17934481, PMID: 10808165, PMID: 27317733, PMID: 17934481, PMID: 10808165, PMID: 27317733, PMID: 24679437, PMID: 19239902, PMID: 20567250, PMID: 25045879, PMID: 15932016, PMID: 21616437, or PMID: 26632377. Some embodiments provided herein relate to a SABR and wherein the signal transduction domain comprises one or more of the domains of Table 0.3. In some embodiments, a fragment of the signal transduction domain in Table 0.3 can be employed.

TABLE 0.3

| Domain | Class/Source | Function | Ref |
|---|---|---|---|
| 4-1BB (CD137) | T cell signaling | Antigen discovery, Fratricide Immunotherapy, Tolerogenic Immunotherapy | PMID: 23667569, PMID: 22437870 |
| CD28 | T cell signaling | Antigen discovery, Fratricide Immunotherapy, Tolerogenic Immunotherapy | PMID: 23667569, PMID: 22437870 |
| CD27 | T cell signaling | Antigen discovery, Fratricide Immunotherapy, Tolerogenic Immunotherapy | PMID: 23667569, PMID: 22437870 |
| DAP10 | T cell signaling | Antigen discovery, Fratricide Immunotherapy, Tolerogenic Immunotherapy | PMID: 23667569, PMID: 22437870 |
| ICOS, OX40, PD1, CTLA4, TIM3 | T cell signaling | Antigen discovery, Fratricide Immunotherapy, Tolerogenic Immunotherapy, Modulating exhaustion | PMID: 23667569, PMID: 22437870 |
| CD3zeta | T cell signaling | Antigen discovery, Fratricide Immunotherapy, Tolerogenic Immunotherapy | PMID: 23667569, PMID: 22437870 |
| Notch and synNotch | Synthetic domains | Antigen discovery, Immunomodulation, Vaccine boost, Modulating exhaustion | PMID: 26830878; U.S. Pat. No. 9,670,281 |
| Chemical-induced dimerization | Synthetic domains | Antigen discovery, Immunomodulation | PMID: 26431673 |
| CD79A, B | B cell signaling | Tolerogenic Immunotherapy, Immunomodulation, Vaccine boost | PMID: 21816833 |
| CD72 | B cell signaling | Tolerogenic Immunotherapy, Immunomodulation, Vaccine boost | PMID: 21816833 |
| CD22 | B cell signaling | Tolerogenic Immunotherapy, Immunomodulation, Vaccine boost | PMID: 21816833 |
| CD5 | B cell signaling | Tolerogenic Immunotherapy, Immunomodulation, Vaccine boost | PMID: 21816833 |
| CD19 | B cell signaling | Tolerogenic Immunotherapy, Immunomodulation, Vaccine boost | PMID: 21816833 |
| CD45 | B cell signaling | Tolerogenic Immunotherapy, Immunomodulation, Vaccine boost | PMID: 21816833 |
| Cytokines such as IL2, IL4, EPO, GM-CSF | Cytokine signaling | Tolerogenic Immunotherapy, Immunomodulation, Vaccine boost | PMID: 17934481; PMID: 10808165; PMID: 27317733 |
| JAK-STAT | Cytokine signaling | Tolerogenic Immunotherapy, Immunomodulation, Vaccine boost | PMID: 17934481; PMID: 10808165; PMID: 27317733 |
| Chemokines such as CCL10 | Cytokine signaling | Tolerogenic Immunotherapy, Immunomodulation, Vaccine boost | PMID: 24679437 |
| G protein coupled receptors | Cytokine signaling | Tolerogenic Immunotherapy, Immunomodulation, Vaccine boost | PMID: 24679437 |
| TNF Receptor superfamily | Cytokine signaling | Immunomodulation, Vaccine boost | PMID: 19239902 |
| NK cell receptors | Innate immune signaling | Immunomodulation, Vaccine boost | PMID: 20567250 |
| Fc Receptors | Innate immune signaling | Immunomodulation, Vaccine boost | PMID: 25045879 |
| Toll-like Receptors | Innate immune signaling | Immunomodulation, Vaccine boost | PMID: 15932016 |
| RIG-I-like receptors | Innate immune signaling | Immunomodulation, Vaccine boost | PMID: 21616437 |
| NOD-like receptors | Innate immune signaling | Immunomodulation, Vaccine boost | PMID: 26632377 |

In some embodiments, any of the options in table 0.1 can be combined with any of the options in table 0.2 and with any of the options in table 0.3. In some embodiments, any of the options in tables 0.1-0.3 can be combined with any antigen presenting domain (MHC I or MHC II or binding domain thereof). In some embodiments, any of the SABRs provided herein can have any of the components provided in tables 0.1-0.3 in it.

Some embodiments provided herein relate to a SABR comprising a transmembrane domain.

Some embodiments provided herein relate to a SABR comprising a transmembrane domain, wherein the transmembrane domain comprises a transmembrane domain from one or more of 4-1BB (CD137), CD28, CD27, DAP10, ICOS, OX40, PD1, CTLA4, TIM3, CD3zeta, Notch, syn-Notch, chemical-induced dimerization, CD79A, CD79B, CD72, CD22, CD5, CD19, CD45, IL2, IL4, EPO, GM-CSF, JAK-STAT, CCL10, a G protein coupled receptor, a receptor of the TNF Receptor superfamily, a NK cell receptor, a Fc receptor, a toll-like receptor, a RIG-I-like receptor, or a NOD-like receptor, or a MHC molecule. Some embodiments provided herein relate to a SABR comprising a transmembrane domain, wherein the transmembrane domain comprises a transmembrane domain from one or more of PMID: 23667569, PMID: 22437870, PMID: 23667569, PMID: 22437870, PMID: 23667569, PMID: 22437870, PMID: 23667569, PMID: 22437870, PMID: 23667569, PMID: 22437870, PMID: 26830878, U.S. Pat. No. 9,670,281, PMID: 26431673, PMID: 21816833, PMID: 17934481, PMID: 10808165, PMID: 27317733, PMID: 17934481, PMID: 10808165, PMID: 27317733, PMID: 24679437, PMID: 19239902, PMID: 20567250, PMID: 25045879, PMID: 15932016, PMID: 21616437, or PMID: 26632377. Some embodiments provided herein relate to a SABR comprising a transmembrane domain, wherein the transmembrane domain comprises a transmembrane domain from one or more of the domains of Table 0.3.

Some embodiments provided herein relate to a SABR comprising: an antigen presenting domain, a signal transduction domain, wherein the antigen presenting domain comprises a binding fragment of a MHC molecule, and a transmembrane domain, wherein the transmembrane domain comprises any one or more of the transmembrane domains of Tables 0.1, 0.2, or 0.3.

Some embodiments provided herein relate to a SABR comprising: an antigen presenting domain, and a signal transduction domain, wherein the antigen presenting domain comprises a binding fragment of a MHC molecule, wherein the antigen presenting domain comprises any one or more of the antigen presenting domains of Tables 0.1, 0.2, or 0.3.

Some embodiments provided herein relate to a SABR comprising: an antigen presenting domain, and a signal transduction domain, wherein the antigen presenting domain comprises a binding fragment of a MHC molecule, and wherein the signal transduction domain comprises any one or more of the signal transduction domains of Tables 0.1, 0.2, or 0.3.

Some embodiments provided herein relate to a SABR wherein the antigen presenting domain is fused to the signal transduction domain. In some embodiments, the MHC portion of the SABR includes some or all of a MHC. In some embodiments, the MHC is a human MHC. In some embodiments, the MHC includes one or more or all of the conserved sequences of the MHC (e.g., the conserved residues within any one of FIGS. 20A-20F.

Some embodiments provided herein relate to a SABR comprising one or more linkers.

Cell Compositions

Each of the embodiments provided herein with regard to Signaling and Antigen-Presenting Bifunctional Receptors (SABRs) can be used within the present embodiments described herein with regard to Cell Compositions.

Some embodiments provided herein relate to a cell comprising: an extracellular peptide-MHC complex comprising: an antigen presenting domain linked to a signal transduction domain, wherein the antigen presenting domain comprises an MHC molecule.

Some embodiments herein relate to a cell comprising any of the SABRs described herein. Some embodiments herein relate to a cell comprising a SABR comprising: an antigen presenting domain, and a signal transduction domain, wherein the antigen presenting domain comprises a binding fragment of a MHC molecule. Some embodiments herein relate to a cell comprising any of the SABRs described herein, wherein the antigen presenting domain comprises a MHC. Some embodiments herein relate to a cell comprising any of the SABRs described herein, wherein the MHC comprises a Class I MHC. Some embodiments herein relate to a cell comprising any of the SABRs described herein, wherein the MHC comprises a Class II MHC. Some embodiments herein relate to a cell comprising any of the SABRs described herein, the SABR further comprising a peptide, wherein the peptide comprises an epitope, wherein the peptide epitope is covalently linked to the SABR, and wherein the antigen presenting domain binds to the peptide. Some embodiments herein relate to a cell comprising any of the SABRs described herein, wherein the signal transduction domain comprises a T cell signaling domain. Some embodiments herein relate to a cell comprising any of the SABRs described herein, the SABR further comprising a transmembrane domain. Some embodiments herein relate to a cell comprising any of the SABRs described herein, the SABR further comprising a transmembrane domain comprising any one or more of the transmembrane domains of Tables 0.1, 0.2, or 0.3. Some embodiments herein relate to a cell comprising any of the SABRs described herein, wherein the antigen presenting domain comprises any one or more of the antigen presenting domains of Tables 0.1, 0.2, or 0.3. Some embodiments herein relate to a cell comprising any of the SABRs described herein, wherein the signal transduction domain comprises any one or more of the signal transduction domains of Tables 0.1, 0.2, or 0.3. Some embodiments herein relate to a cell comprising any of the SABRs described herein, wherein the antigen presenting domain is fused to the signal transduction domain. Some embodiments herein relate to a cell comprising any of the SABRs described herein, the SABR further comprising one or more linkers.

Some embodiments herein relate to a cell comprising any of the SABRs described herein, wherein the cell is sourced from any T cell line such as Jurkat cells, NFAT-GFP-Jurkat cells. Some embodiments herein relate to a cell comprising any of the SABRs described herein, wherein the cell is sourced from primary T cells from a patient or healthy donors or Natural Killer cells. Some embodiments herein relate to a cell comprising any of the SABRs described herein, wherein the cell is sourced from regulatory T cells, dendritic cells, B cells, macrophages, or Natural Killer cells.

Nucleic Acid Encoding

Each of the embodiments provided herein with regard to Signaling and Antigen-Presenting Bifunctional Receptors can be used within the present embodiments described herein with regard to Nucleic Acid Encoding.

Some embodiments herein relate to an isolated nucleic acid molecule comprising a nucleotide sequence encoding any one of the SABRs described herein. Some embodiments herein relate to an isolated nucleic acid molecule comprising a nucleotide sequence encoding any one of the SABRs described herein, the SABR comprising: an antigen presenting domain, and a signal transduction domain, wherein the antigen presenting domain comprises a binding fragment of a MHC molecule. Some embodiments herein relate to an isolated nucleic acid molecule comprising a nucleotide sequence encoding any one of the SABRs described herein, wherein the antigen presenting domain comprises a MHC. Some embodiments herein relate to an isolated nucleic acid molecule comprising a nucleotide sequence encoding any one of the SABRs described herein, wherein the MHC comprises a Class I MHC. Some embodiments herein relate to an isolated nucleic acid molecule comprising a nucleotide sequence encoding any one of the SABRs described herein, wherein the MHC comprises a Class II MHC. Some embodiments herein relate to an isolated nucleic acid molecule comprising a nucleotide sequence encoding any one of the SABRs described herein, the SABR further comprising a peptide, wherein the peptide comprises an epitope, wherein the peptide epitope is covalently linked to the SABR, and wherein the antigen presenting domain binds to the peptide. Some embodiments herein relate to an isolated nucleic acid molecule comprising a nucleotide sequence encoding any one of the SABRs described herein, wherein the signal transduction domain comprises a T cell signaling domain. Some embodiments herein relate to an isolated nucleic acid molecule comprising a nucleotide sequence encoding any one of the SABRs described herein, the SABR further comprising a transmembrane domain. Some embodiments herein relate to an isolated nucleic acid molecule comprising a nucleotide sequence encoding any one of the SABRs described herein, the SABR further comprising a transmembrane domain, wherein the transmembrane domain comprises any one or more of the transmembrane domains of Tables 0.1, 0.2, or 0.3. Some embodiments herein relate to an isolated nucleic acid molecule comprising a nucleotide sequence encoding any one of the SABRs described herein, wherein the antigen presenting domain comprises any one or more of the antigen presenting domains of Tables 0.1, 0.2, or 0.3. Some embodiments herein relate to an isolated nucleic acid molecule comprising a nucleotide sequence encoding any one of the SABRs described herein, wherein the signal transduction domain comprises any one or more of the signal transduction domains of Tables 0.1, 0.2, or 0.3. Some embodiments herein relate to an isolated nucleic acid molecule comprising a nucleotide sequence encoding any one of the SABRs described herein, wherein the antigen presenting domain is fused to the signal transduction domain. Some embodiments herein relate to an isolated nucleic acid molecule comprising a nucleotide sequence encoding any one of the SABRs described herein, the SABR further comprising one or more linkers.

Methods for Signaling Cell Preparation

Each of the embodiments provided above with regard Signaling and Antigen-Presenting Bifunctional Receptors (SABRs) can be used within the present embodiments described herein with regard to Methods for Signaling Cell Preparation.

Some embodiments herein relate to a method for preparing a signaling cell. The method comprises: providing a target cell, and introducing into the target cell a nucleic acid molecule comprising a nucleotide sequence coding for an SABR directed against at least one T-cell receptor (TCR) expressed at the surface of a T-cell, wherein the SABR comprises a MHC linked to a signal transduction domain.

Methods for Antigen Discovery

Each of the embodiments provided above with regard Signaling and Antigen-Presenting Bifunctional Receptors (SABRs) can be used within the present embodiments described herein with regard to Methods for Antigen Discovery.

Antigen discovery refers to identifying one or more peptide sequences of a protein. In some embodiments, the identified antigens can be used in making vaccines for treatment of patients. In some embodiments, antigen receptor discovery refers to identifying one or more antigen receptors that recognizes a specific antigen. For example, antigen receptor discovery may comprise identifying one or more specific TCRs of a plurality of TCRs that recognize a specific antigen. In some embodiments, identified antigen receptors (e.g. TCRs) can be used for immunotherapy. In some embodiments, the SABRs described herein can be used for both antigen discovery and antigen receptor discovery.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cells producing the measurable signal, thereby identifying an antigen by associating the SABR in the cell with the reporter, with the antigen receptor.

Some embodiments herein relate to a method for antigen discovery, the method comprising: expressing any of the SABRs described herein in at least one reporter cell, wherein the at least one reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, identifying the at least one reporter cells producing the measurable signal, thereby identifying an antigen by associating the SABR in the cell with the reporter, with the antigen receptor, and identifying at least one peptide in the at least one reporter cell producing the measurable signal, thereby associating the peptide with the SABR with the antigen receptor.

FIG. 2A illustrates a schematic describing the use of SABRs in a reporter cell line that expresses a signal upon TCR signal transduction according to various embodiments herein. In some embodiments, for the use of SABRs 200 for antigen-discovery, TCR-cross-reactivity, and related approaches, SABRs 200 can be expressed in reporter cells 202 that produce a measurable signal upon signal transduction. An example of the use of SABRs 200 relies on a reporter cell line (e.g. NFAT-GFP-Jurkat cells), which express green fluorescent protein (GFP) upon T cell signal transduction. In some embodiments, T cells expressing a given TCR can be incubated with SABR-expressing, for example, NFAT-GFP-Jurkat cells. In some embodiments, the SABR-expressing cells can express GFP if a cognate antigen 204 presented by SABRs 200 is recognized by the T cells. In some embodiments, presentation of an irrelevant antigen 206, or an irrelevant TCR 208, by SABRs will not result in GFP expression, allowing identification of the SABRs 200 presenting the cognate antigen 204 by flow cytometry.

Figure 2B:
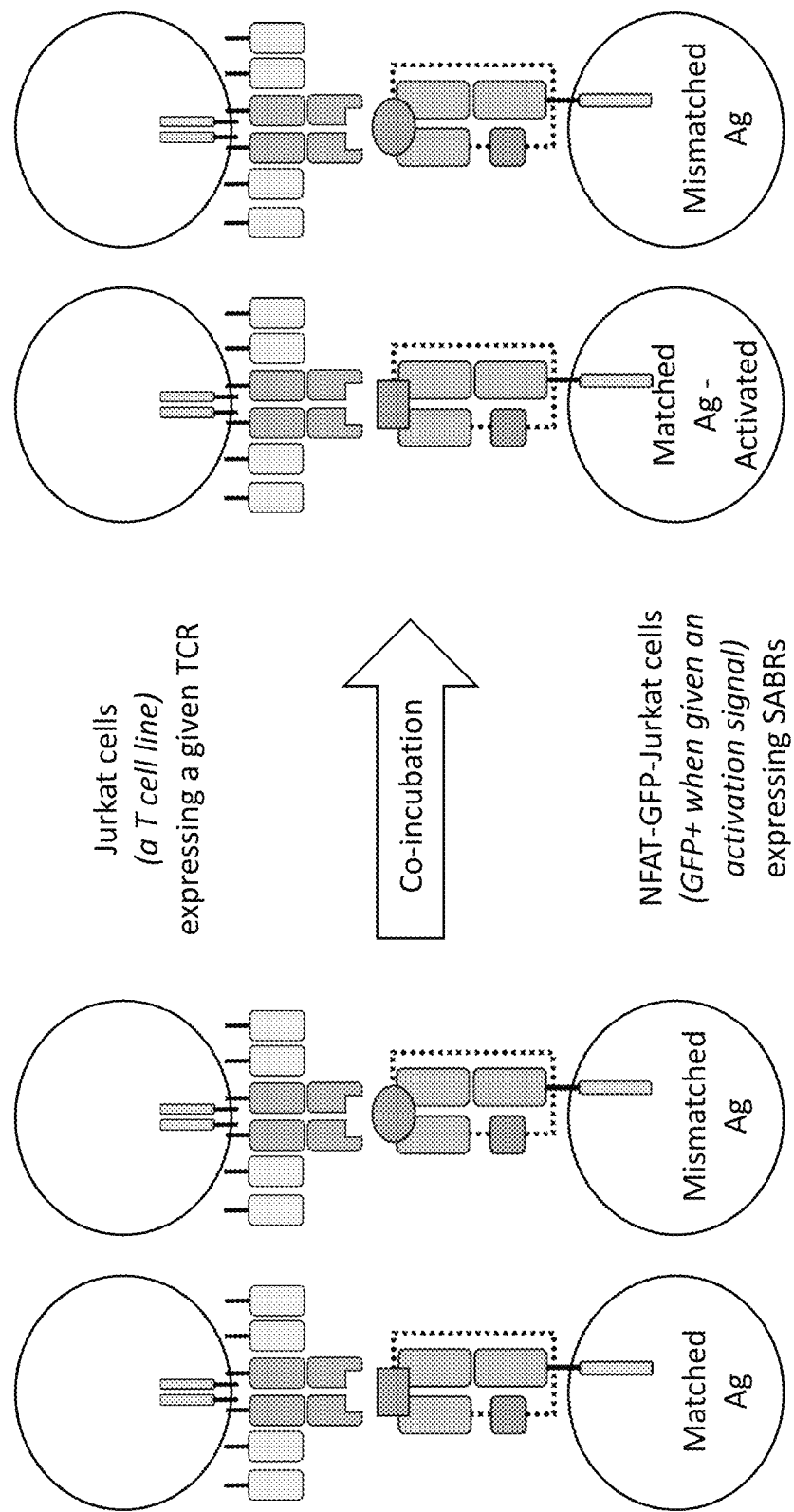
FIG. 2B illustrates a flowchart describing a process for antigen specific signaling by SABRs described herein.

FIG. 2B illustrates a flowchart describing a process for antigen specific signaling by SABRs described herein. Jurkat cells expressing a given TCR can be co-incubated with, for example, NFAT-GFP-Jurkat cells expressing SABRs. SABRs comprising matching antigens to the expressed TCR can activate upon recognition by the TCR, which can induce signaling with the NFAT-GFP-Jurkat cell. SABRs comprising mismatched or irrelevant antigens may not be recognized by the expressed TCR and may not activate.

Some embodiments herein relate to a method for antigen discovery, the method comprising: expressing any of the SABRs described herein in at least one reporter cell, wherein the at least one reporter cell produces a measurable signal upon a signal transduction event that occurs upon binding of an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor comprises a soluble molecule.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor comprises a soluble molecule, wherein the soluble molecule comprises an antibody.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor is expressed on a cell.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor is expressed on a cell, and wherein the antigen receptor comprises a TCR expressed on a T cell.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the at least one reporter cell comprises a library of cells, wherein the library of cells have numerous different SABRs, and wherein the numerous different SABRs can bind to different antigen receptors.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor comprises numerous antigen receptors Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein numerous different SABRs are expressed and one determines which SABR a particular antigen receptor binds to ("antigen discovery") by monitoring the measurable signal and identifying which SABR is in the cell that exhibited the measurable signal.

Some embodiments herein relate to a method for antigen discovery (and/or antigen receptor discovery), the method comprising: expressing any of the SABRs described herein in at least one reporter cell, wherein the reporter cell produces a measurable signal upon a signal transduction event that occurs upon binding of an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein more than one antigen receptor is present and one determines which antigen receptor binds to a particular SABR.

Some embodiments herein relate to a method for antigen discovery (and/or antigen receptor discovery_, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein more than one antigen receptor and more than one SABR are present.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the reporter cells comprise NFAT-GFP-Jurkat cells.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the reporter cells comprise NFAT-GFP-Jurkat cells, cells of any T cell line, cells of any B cell line, cells of any NK cell line, monocytic cell line, or myeloid cell line Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the measureable signal comes from expression of a detectable marker.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the reporter cells expressing the measurable signal are identified using flow cytometry.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor cells comprise cells expressing orphan T-cell receptors (TCR).

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the antigen receptor comprises an expressed orphan T-cell receptors (TCR).

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the at least one reporter cell expresses a genetically encoded antigen or antigenic epitope.

Some embodiments herein relate to a method for antigen discovery, the method comprising: expressing any of the SABRs described herein in at least one reporter cell, wherein the reporter cell produces a measurable signal upon a signal transduction event that occurs upon binding of a an antigen receptor to the antigen presenting domain, incubating the at least one reporter cell with an antigen receptor to be tested for binding to the SABR, detecting a presence of a measurable signal in the at least one reporter cell when the antigen receptor binds, and identifying the at least one reporter cell producing the measurable signal, thereby identifying an antigen by associating the SABR in the cell with the reporter, with the antigen receptor, wherein the at least one reporter cell expresses a genetically encoded antigen or antigenic epitope, and further comprising identifying the genetically encoded antigen or antigenic epitope by DNA sequencing.

Cell Libraries

Each of the embodiments provided herein with regard Signaling and Antigen-Presenting Bifunctional Receptors can be used within the present embodiments described herein with regard to Cell Libraries.

Some embodiments herein relate to a library comprising: any of the SABRs described herein, and at least one candidate antigen receptor.

Some embodiments herein relate to a library comprising: any of the SABRs described herein, and at least one candidate antigen receptor, wherein the at least one antigen receptor is expressed on a cell, wherein the cell is an antigen receptor cell. Some embodiments herein relate to a library comprising: any of the SABRs described herein, and at least one candidate antigen receptor, wherein the at least one antigen receptor is expressed on a cell, wherein the cell is a reporter cell.

Some embodiments herein relate to a library comprising: any of the SABRs described herein, and at least one candidate antigen receptor, wherein the at least one antigen receptor is expressed on a cell, wherein the SABR is expressed on a reporter cell, such that the cell provides a detectable marker upon binding of the SABR to the antigen receptor.

Some embodiments herein relate to a library comprising: any of the SABRs described herein, and at least one candidate antigen receptor, wherein the at least one antigen receptor is expressed on a cell, wherein the reporter cell comprises NFAT-GFP-Jurkat cells.

Some embodiments herein relate to a library comprising: any of the SABRs described herein, and at least one candidate antigen receptor, wherein the at least one antigen receptor is expressed on a cell, wherein the at least one antigen receptor is expressed on a cell, wherein the cell is an antigen receptor cell, and wherein the antigen receptor cell comprises T cells comprising TCR.

Some embodiments herein relate to a library comprising: any of the SABRs described herein, and at least one candidate antigen receptor wherein the at least one antigen receptor is expressed on a cell, wherein the cell is an antigen receptor cell, and wherein the antigen receptor cell comprises a cell expressing orphan TCR.

Figure 2C:
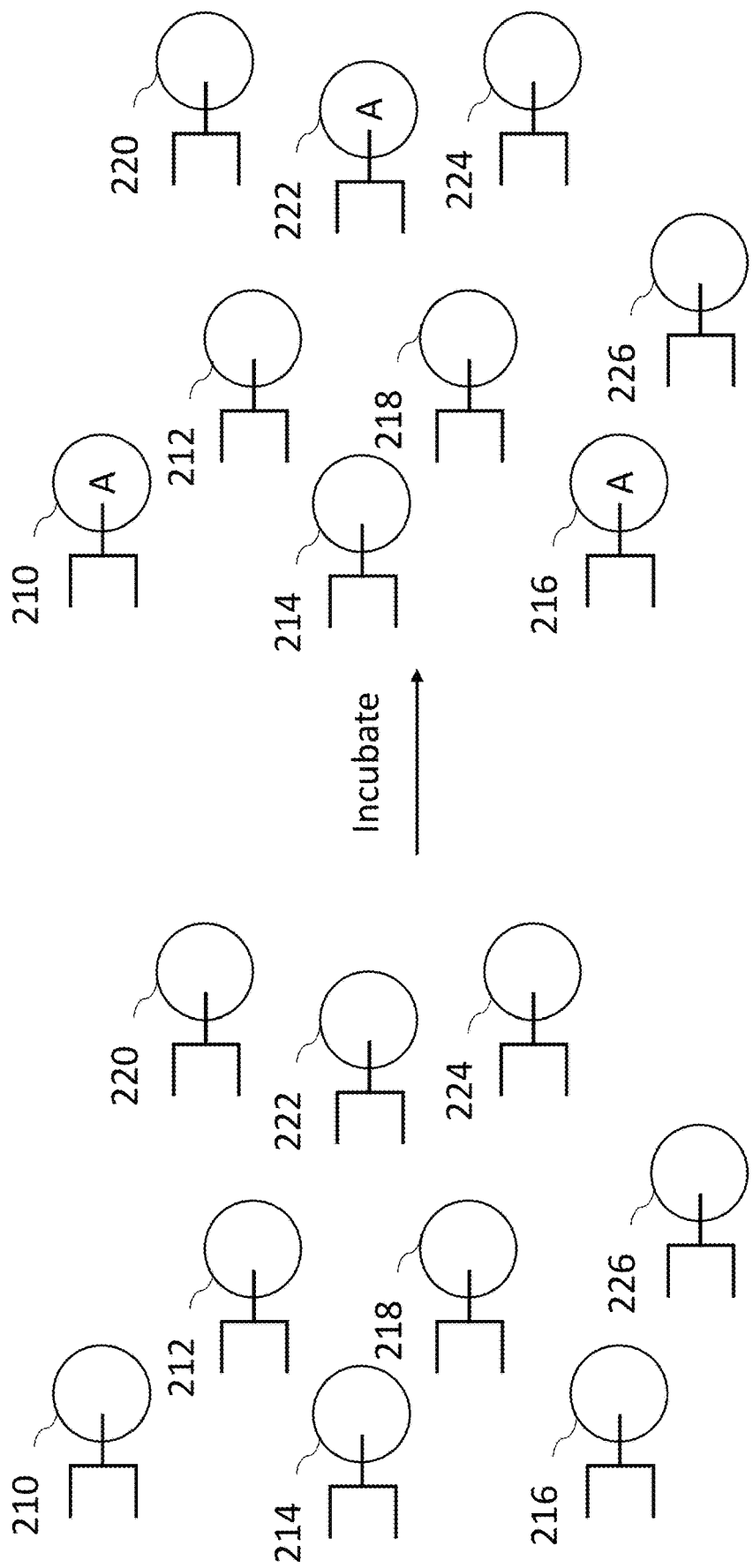
FIG. 2C illustrates a schematic demonstrating a use of a SABR library for antigen discovery according to various embodiments herein.

FIG. 2C illustrates a schematic demonstrating the use of a SABR library for antigen discovery according to various embodiments herein. In some embodiments, reporter cells, such as NFAT-GFP-Jurkat cells expressing a library of SABRs, can be used to uncover antigen specificities. In some embodiments, each cell 210, 212, 214, 216, 218, 220, 222, 224, and 226 in the SABR library expresses a unique genetically encoded antigen or antigenic epitope, which can be identified by DNA sequencing. In some embodiments, the SABR library can be co-incubated with T cells with unknown specificities, or T cell lines expressing a TCR with unknown specificity. In some embodiments, cells producing a signal, such as GFP+ cells 210, 216, and 222 can be sorted and the antigenic epitopes can be sequenced to determine the cognate antigen of the given T cell or TCR.

Therapeutic Methods

Each of the embodiments provided above with regard Signaling and Antigen-Presenting Bifunctional Receptors can be used within the present embodiments described herein with regard to Therapeutic Methods.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject. Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject, and wherein the therapeutic cell comprises CD8+ T cells, CD4+ T cells, Regulatory T cells, B cells, NK cells, Dendritic cells, Macrophages, Monocytes, or any hematopoietic cells including, for example hematopoietic stem cells, progenitors, lymphoid and myeloid cells.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject, and wherein the cellular response results in one or more of: cell mediated cytotoxicity, release of inflammatory cytokines, release of suppressive cytokines, direct suppression of target cells, release of anti-inflammatory cytokines, induction of pro-proliferative signals, induction of anti-proliferative signals, induction of apoptosis, induction of cell exhaustion markers, or direct target cell activation.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject, and wherein the therapeutic cell destroys a pathogenic T cell.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject, and wherein the therapeutic cell activates a target T cell.

Some embodiments herein relate to a method for initiating a therapeutic response, the method comprising: transducing a therapeutic cell with any one or more of the SABRs described herein, and administering the therapeutic cell to a subject in need of treatment, wherein the SABR directs a cellular response in the subject upon binding to an antigen receptor in the subject, and wherein the therapeutic cell suppresses a pathogenic T cell.

Some embodiments herein relate to a method for treating a patient comprising introducing into the patient a therapeutic T-cell comprising an extracellular peptide-MHC complex, the peptide-MHC complex comprising an antigen presenting domain linked to a signal transduction domain, wherein the antigen presenting domain comprises an MHC.

Therapeutic T Cell Compositions

Each of the embodiments provided herein with regard Signaling and Antigen-Presenting Bifunctional Receptors can be used within the present embodiments described herein with regard to Therapeutic T Cell Compositions.

Some embodiments herein relate to a composition comprising: a therapeutic T-cell comprising any of the SABRs described herein.

Additional SABR Compositions

Provided in this section are additional options for arrangements and combinations of SABRs and uses thereof.

Some embodiments herein relate to a SABR comprising: an extracellular binding domain comprising an MHC and a peptide epitope, a transmembrane domain, and a cytoplasmic signaling domain.

Cell-based Platform for T cell Antigen Discovery

Each of the embodiments provided herein with regard Signaling and Antigen-Presenting Bifunctional Receptors can be used within the present embodiments described herein with regard to a Cell-Based Platform for T cell Antigen Discovery.

Some embodiments herein relate to chimeric SABRs in a novel cell-based platform for TCR antigen discovery. In some embodiments, SABRs present an extracellular peptide-MHC complex and induce intracellular signaling via a TCR-like signal upon binding with a cognate TCR. Some embodiments herein relate to antigen discovery using SABR libraries to screen, for example, thousands of antigenic epitopes. This platform was verified by identifying the targets recognized by public TCRs of known specificities. Moreover, this approach can be extended for personalized neoantigen discovery. In some embodiments, the antigen discovery platform described herein can provide a scalable and versatile way to develop novel targets for immunotherapy.

A CD8+ T cell encodes a unique surface T Cell Receptor (TCR) that recognizes 8-12 residue long peptide epitopes presented on class I MHC molecules, also known as Human Leukocyte Antigens (HLA) in humans. When a TCR complex binds cognate peptide-MHC (pMHC), the CD3ζ chains associated with the TCR complex dimerize to initiate downstream signaling. Multiple signaling cascades are activated, leading to rapid gene expression driven by the transcription factors NF-κB, AP-1, and NFAT7. In CD8+ T cells, TCR signaling induces expression of early activation markers (CD69 and CD107a), release of cytotoxic granules, and secretion of cytokines (IFNγ, IL2, and TNFα), ultimately killing the target cell. The interaction of cognate TCR and pMHC complexes generates a high degree of specificity towards a target antigen. T cells can recognize epitopes presented by tumor cells and infiltrate the tumor microenvironment. Antitumor T cells respond to two kinds of tumor-derived epitopes: 1) Public or private epitopes originating from non-mutated, tissue specific antigens or cancer-testis antigens, and 2) Private neoantigens originating from non-synonymous mutations. Both endogenous antigens and neoantigens can be used to provide targets of immunotherapies.

One of the bottlenecks in the field of tumor immunology is the identification of the antigen recognized by a particular antitumor CD8+ T cell. Several techniques have been developed to identify cognate antigens for T cells. The most common approach uses pMHC multimers to identify antigen-specific T cells by flow cytometry. However, antigen discovery using pMHC multimers requires ab initio knowledge of the antigenic landscape, is not scalable beyond $10^3$ antigens, but can identify multiple antigenic specificities simultaneously. This approach has been used to discover public tumor antigens as well as private neoantigens. One approach uses degenerate libraries of covalently linked. Following multiple rounds of selection, outgrowth, sequencing, and referencing tumor exome data, the cognate antigen of the TCR is identified. However, this approach is technically challenging because of the requirement of soluble TCR, does not represent the physiological TCR-pMHC interaction, but is antigen-agnostic and scalable to 106-108 epitopes. These limitations underscore the need for new techniques for T cell antigen discovery.

Some embodiments herein thus relate to novel antigen discovery techniques to address the unmet need. In some embodiments, cell-based platforms for T cell antigen discovery are presented. In some embodiments, by combining antigen presentation by pMHC complexes with intracellular signaling, SABRs allow identification of a successful TCR-pMHC interaction. Some embodiments relate to TCR antigen discovery using SABR libraries and its use for known public TCRs. Some embodiments relate to adaptation of SABR libraries for a personalized neoantigen-directed approach. Some embodiments describe a flexible and scalable method for T cell antigen discovery.

Additional Contemplated Embodiments

Each of the embodiments provided above with regard Signaling and Antigen-Presenting Bifunctional Receptors can be used within the present embodiments described herein with regard to Additional Contemplated Embodiments.

Various embodiments described herein address the limitations of the TCR-Antigen-MHC interaction through the introduction of SABRs. The use of SABRs, as discussed herein, allows for the utilization of TCR-Antigen-MHC interactions for various functions.

In some embodiments, a function enabled by the SABRs disclosed herein comprises uncovering T cell antigenic specificities in cancers, infectious diseases, and autoimmune diseases. T cell-mediated responses to cancers target multitude of antigens expressed on cancer cells. Knowing the antigens that are targeted is immensely useful for immunotherapy approaches to treat cancers. There are several technologies to uncover epitopes that are targeted by T cells. The most widely used technologies are based on using MHC-peptide-multimers. The use of MHC multimers has several drawbacks—it is labor intensive and not easily scalable, it is not trivial for class II MHC-peptide complexes, and it is not sensitive towards low-affinity interactions. Yeast display has also been tested for TCR antigen discovery but suffers from several drawbacks as well. Yeast display relies on using peptide-MHC-b2microglobulin single chain trimers (SCTs), which mimic antigen presentation and link the antigen genetically to MHC. However, the use of SCT Yeast display technology requires production of soluble TCR molecules, which is not robust, and which cannot be scaled to multiple TCRs easily. Moreover, because yeast lacks endogenous MHC, the SCTs may not fold correctly and may not represent physiological TCR binding. Other technologies that are antigen-directed require prior knowledge of antigenic epitopes from patient samples, or that require expansion of patient T cells that may bias the antigen specificity, or that require large amounts of patient samples that may not be available. The SABR technology described here uses an unbiased approach that will use a library of target cells that are recognized by a given T cell or a TCR. SABRs allow scalability of this approach to, for example, over $10^6$ epitopes and virtually all MHC alleles, including class I and class II alleles, does not require soluble TCR production, allows for low-affinity TCR-pMHC interactions, and can be used without patient tumor samples.

In some embodiments, another function enabled by the SABRs disclosed herein comprises studying T cell receptor cross-reactivity and heteroclitic ligands. TCRs display considerable promiscuity in recognition of the variants of their cognate epitope. The study of TCR cross-reactivity is important to understand the safety and efficacy of a TCR or a T cell bearing a particular TCR. In cancer immunotherapy, the knowledge of the cross-reactivity of a TCR can help understand the off-target or on-target, but unintended effects of using that TCR therapeutically without undesirable side effects. In immunotherapy for viruses such as HIV, the knowledge of TCR cross-reactivity can help understand the propensity of immune escape of the pathogen from that TCR. The current technologies of studying TCR cross-reactivity are based either on low-throughput methods using individual variant peptides, or on yeast display technologies that are laborious and require production of soluble TCRs. In some embodiments, the SABR technology described herein allows for construction of libraries of, for example, $10^3$-$10^6$ antigenic epitope variants for any given MHC-peptide combination, and for subsequent identification of variants that are recognized, without the requirement for soluble TCR production. In addition, this approach can be used to identify variants of a given epitope that may have different binding properties, such as heteroclitic ligands with higher affinity and antagonists.

In some embodiments, yet another function enabled by the SABRs disclosed herein comprises inducing specific T cell responses. Vaccination approaches that elicit T cell responses require presentation of antigen epitopes to T cells and subsequent stimulation of those T cells. Professional antigen presenting cells (APCs) process endogenous or foreign antigens and present them to T cells. Antigen-specific immunity can be elicited by using live attenuated or inactive viruses, soluble antigenic proteins, or by using vectors. However, in these approaches, the antigenic epitopes are processed by the natural cellular machinery, and hence there is no control over whether a given epitope will elicit a strong immune response. To elicit a response to a given epitope, it is expressed in APCs via expression cassettes for entire proteins of via tandem minigenes encoding epitopes. Single chain trimers can also be used to express a given MHC-peptide complex on APCs to elicit an immune response. As single chain trimers cannot signal in the APC, they cannot manipulate how the APC will stimulate T cells. In some embodiments, the SABRs described herein can be coupled to specific signaling molecules that can allow the APCs to secrete cytokines and activate T cells that recognize them. In some embodiments, SABRs can be configured to elicit immunosuppressive cytokines in APCs, which can cause suppression of particular responses.

In some embodiments, yet another function enabled by the SABRs disclosed herein comprises eliminating T cell specificities. Pathogenic T cell clonal specificities may play a central role in T cell leukemias and autoimmune disorders. In T cell leukemia, the outgrown and transformed clones can be specifically targeted based on the antigenic epitopes recognized by them. In autoimmune disorders, T cell clones that are autoreactive can also be targeted based on their cognate epitopes Eliminating T cell clones based on their antigenic specificities allows for precise targeting with minimal off-target effects. The approaches tested so far have relied on monoclonal antibodies that recognize particular TCR variable regions. Targeting specific TCR variable regions provides precision but does not allow for targeting TCRs that may comprise of different variable regions while recognizing the same antigenic specificity. In addition, this approach can result in depletion of all TCRs comprising of a given variable region without regard for their specificities. In some embodiments, SABRs can allow for targeting of TCRs based on their antigen specificity. T cells transduced with SABRs presenting a given epitope can be used therapeutically to eliminate pathogenic T cell specificities. In addition, the identification of antigens that can be recognized by clonal T cells can be used for developing SABRs even without the knowledge of their natural cognate antigen. In some embodiments, the drawbacks of existing technologies can be overcome by linking signaling and antigen presentations through SABRs. By combining antigen presentation and signaling, SABRs allow a robust, scalable, high-throughput, and sensitive approach to initiate signal transduction in cells recognized by given TCRs, therefore allowing a functional output to be generated by them.

In some embodiments, MHC molecules present peptide epitopes on a cell surface for recognition by T cells. In their native form, MHC molecules lack signaling domains, and cannot transduce any signal into the antigen presenting cell. Some embodiments described herein relate to a chimeric construct (e.g. SABR) that adds a signal transduction domain to the intracellular end of MHC molecules. In some embodiments, these SABRs are able to present antigen, and induce an intracellular signal upon recognition by a T cell. In some embodiments, SABRs have two or more distinct functional parts including, for example, including one or more antigen recognition domains that are based on MHC molecules, which present peptide epitopes to T cells. In some embodiments, these can either be genetically encoded and covalently linked to the MHC molecule or expressed in the cell and presented naturally by the MHC molecule. Additionally, in some embodiments, the SABRs comprise one or more signal transduction domains that induce an intracellular signal to induce a transcriptional response upon binding of the SABRs to their cognate T cells. The SABRs constructs can be used for multiple different purposes, such as for antigen-discovery in cancer, autoimmune disorders, and infectious diseases, for immunotherapeutic approaches to eliminate T cell specificities, for inducing antigen specific cytokine signaling.

Figure 3A:
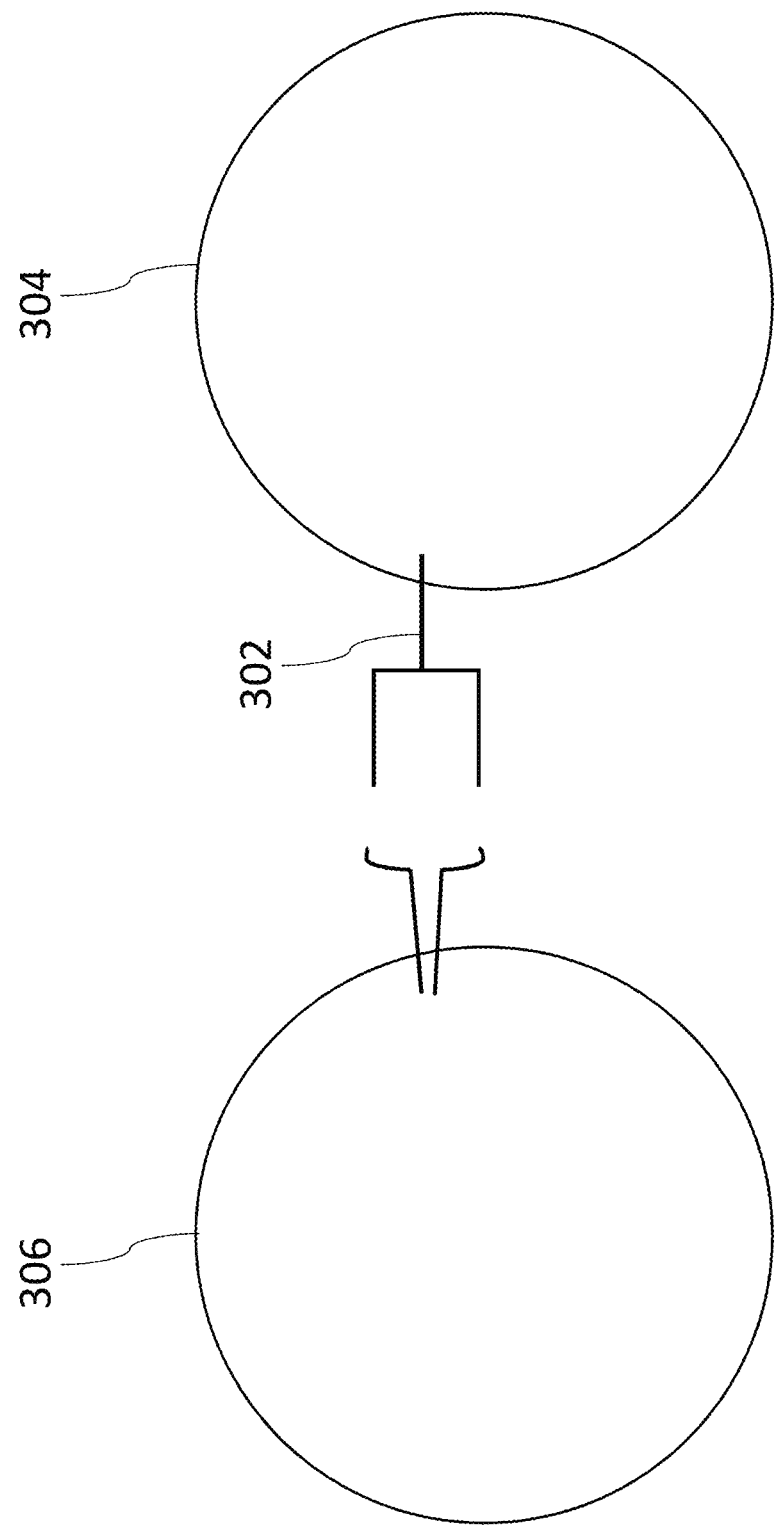
FIG. 3A illustrates a schematic of T cells and target cells used to demonstrate a function of SABRs according to various embodiments herein.

FIG. 3A illustrates a schematic of the T cells and target cells used to demonstrate the function of SABRs according to various embodiments herein. In some embodiments, class I SABRs 302 can be constructed based on the two constructs shown in FIG. 1C. These include the SCTR constructs, which consist of the peptide epitope covalently linked to MHC, and the SCDR constructs, which can, in some embodiments, be forced to present a peptide epitope that is not genetically linked to MHC. In some embodiments, the SCTR constructs can be constructed to express, for example, either A2-NYESO (a cancer-specific MHC-antigen combination) or B27-KK10 (an HIV-specific MHC-antigen combination). In some embodiments, the SCDR constructs for A2 and B27 can be constructed and a peptide can be used to present, for example, either NYESO or KK10 antigen. In some embodiments, for example, NFAT-GFP-Jurkats, can be transduced with the SCTR constructs or with SCDR constructs and pulsed with peptide antigen as reporter cells 304. In some embodiments, the reporter cells 304 can be transduced with Jurkat cells 306 expressing, for example, either A2-NYESO-specific TCR or B27-KK10-specific TCR, and the frequency of GFP+ cells can be measured with flow cytometry.

Figure 3B:
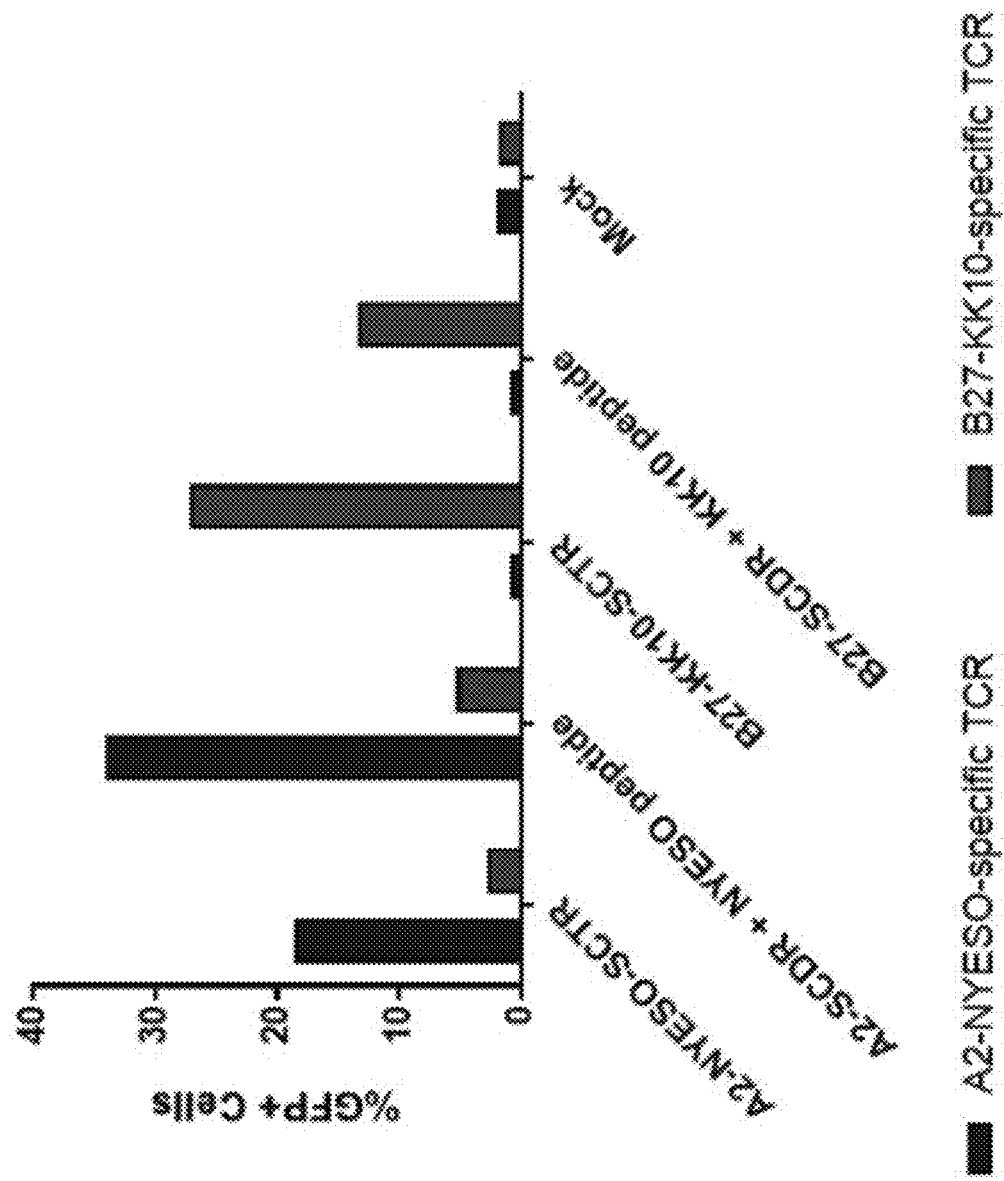
FIG. 3B illustrates a chart depicting measurement of GFP expression in SABR transduced reporter cells upon co-incubation with T cells expressing TCRs.
Figure 3C:
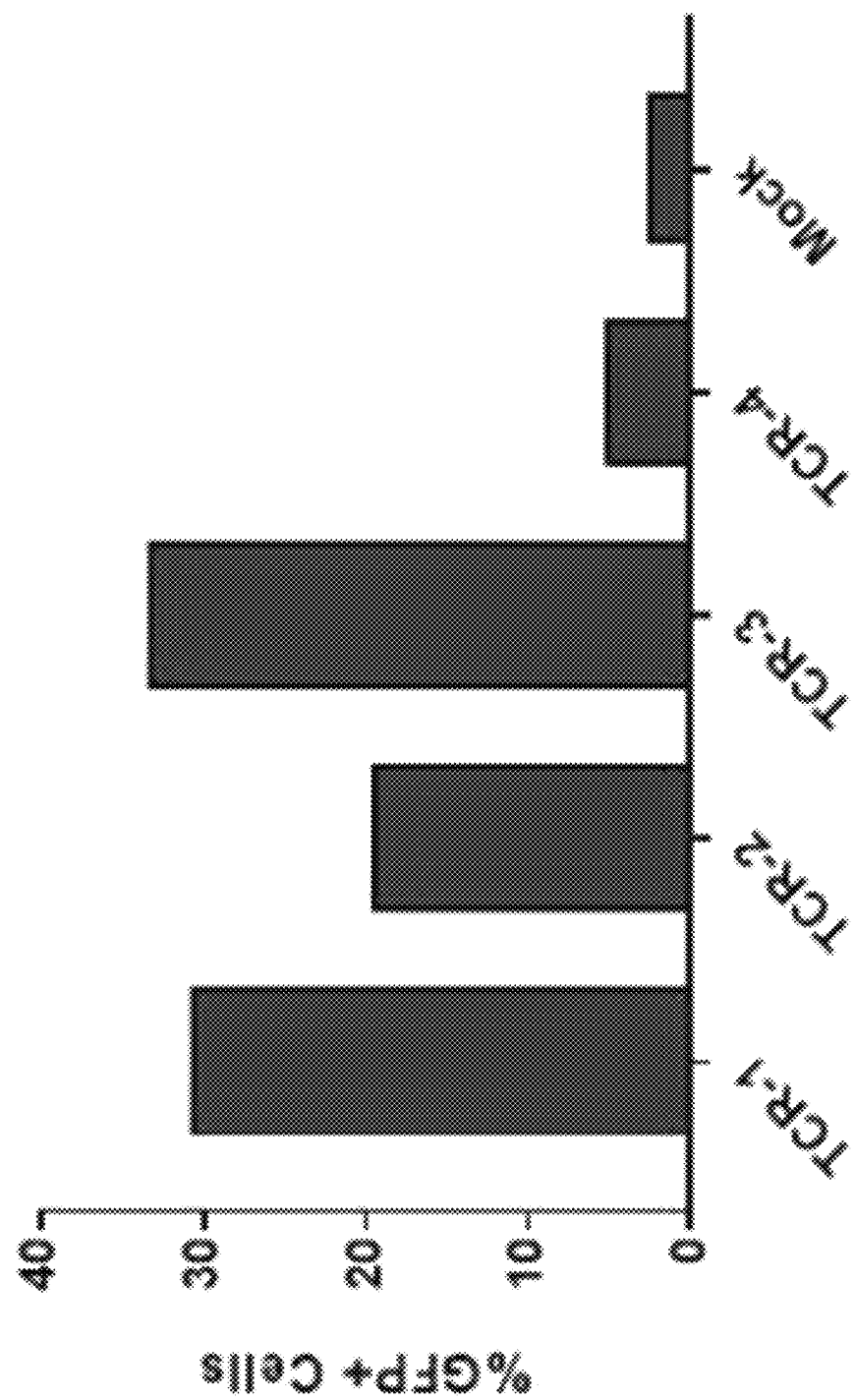
FIG. 3C illustrates a chart demonstrating a function of B27-KK10-SCTRs in response to four different TCRs from different patients.

As shown in FIG. 3B, NFAT-GFP-Jurkats may express GFP only upon specific recognition of MHC-antigen by SABRs. FIG. 3C illustrates a similar assay using NFAT- GFP-Jurkat cells expressing B27-KK10-SCTR constructs according to various embodiments. In some embodiments, Jurkat cells can be transduced with four different B27-KK10-specific TCRs from four different HIV patients and incubated them with the NFAT-GFP-Jurkat cells. As shown in FIG. 3C, the reporter cells can express GFP upon being recognized by all four TCRs. Therefore, in some embodiments, class I SABRs function in the proposed way discussed above and can be used in a reporter cell line.

Figure 4A:
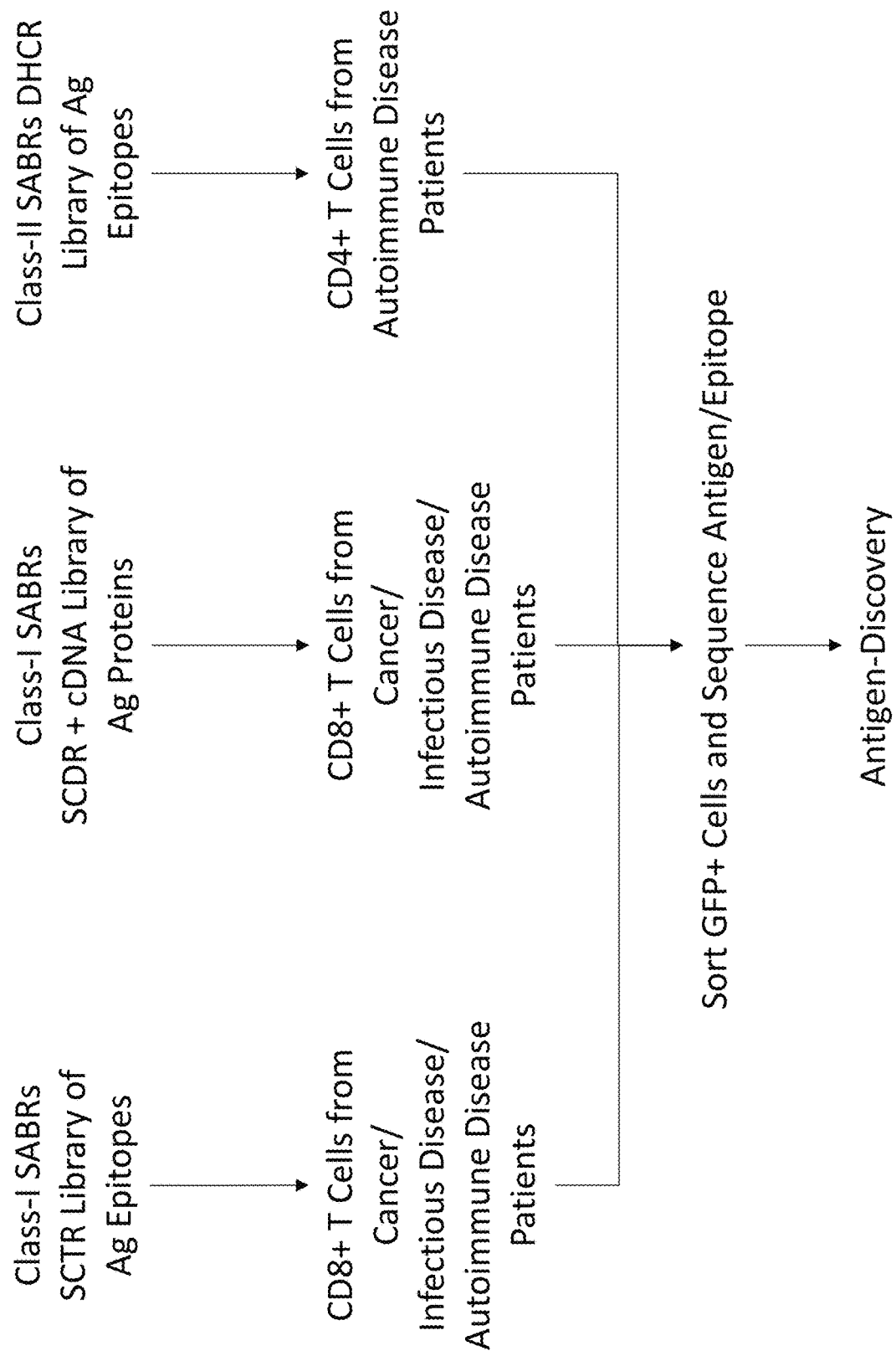
FIG. 4A illustrates a schematic describing a use of various SABR constructs for T cell antigen discovery according to various embodiments herein.
Figure 4B:
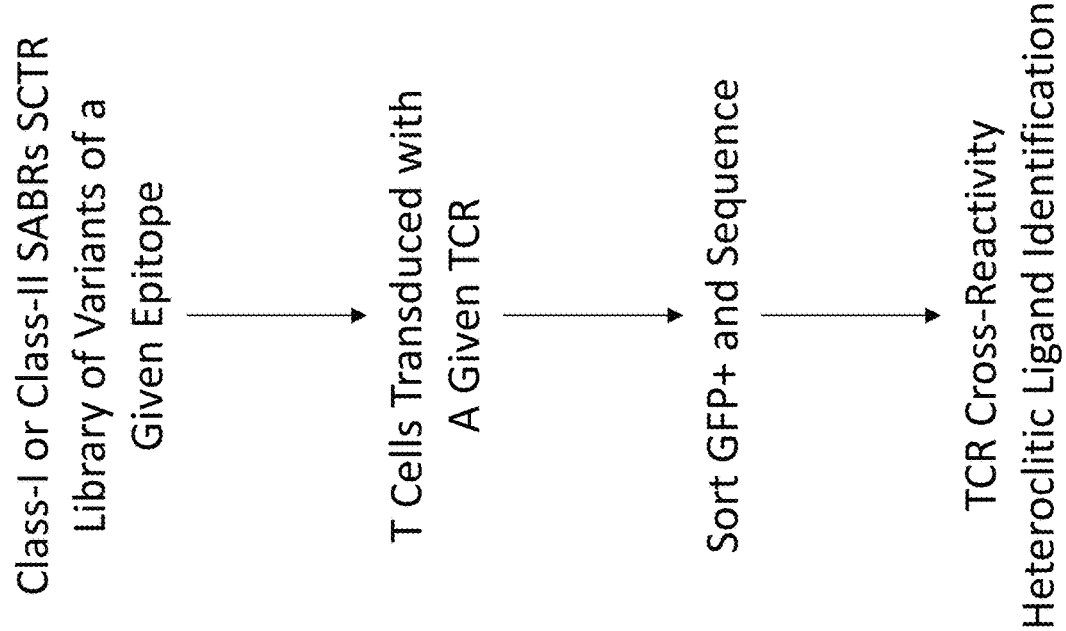
FIG. 4B illustrates a schematic describing a use of SCTRs to study TCR cross-reactivity or to identify heteroclitic ligands according to various embodiments herein.

FIG. 4A illustrates a schematic describing the use of various SABR constructs for T cell antigen discovery according to various embodiments herein. FIG. 4B illustrates a schematic describing the use of SCTRs to study TCR cross-reactivity or to identify heteroclitic ligands according to various embodiments herein. In some embodiments, using these approaches, the antigenic reactivities of cancer-specific, pathogen-specific, or autoreactive T cells can be identified. In some embodiments, SABR libraries expressing antigens or antigenic epitopes from cancers, pathogens, normal cellular proteome can be constructed. In some embodiments, these libraries can be used to identify T cell specificities in, for example, cancer immunity, in autoimmune disorders including diabetes and neurodegenerative disorders, in immunity against pathogens, and in vaccine responses (FIG. 4A). In some embodiments, for a given T cell specificity, SABR libraries expressing variants of the cognate epitope can be constructed and used to understand TCR cross-reactivity and to identify heteroclitic ligands (FIG. 4B).

Figure 5A:
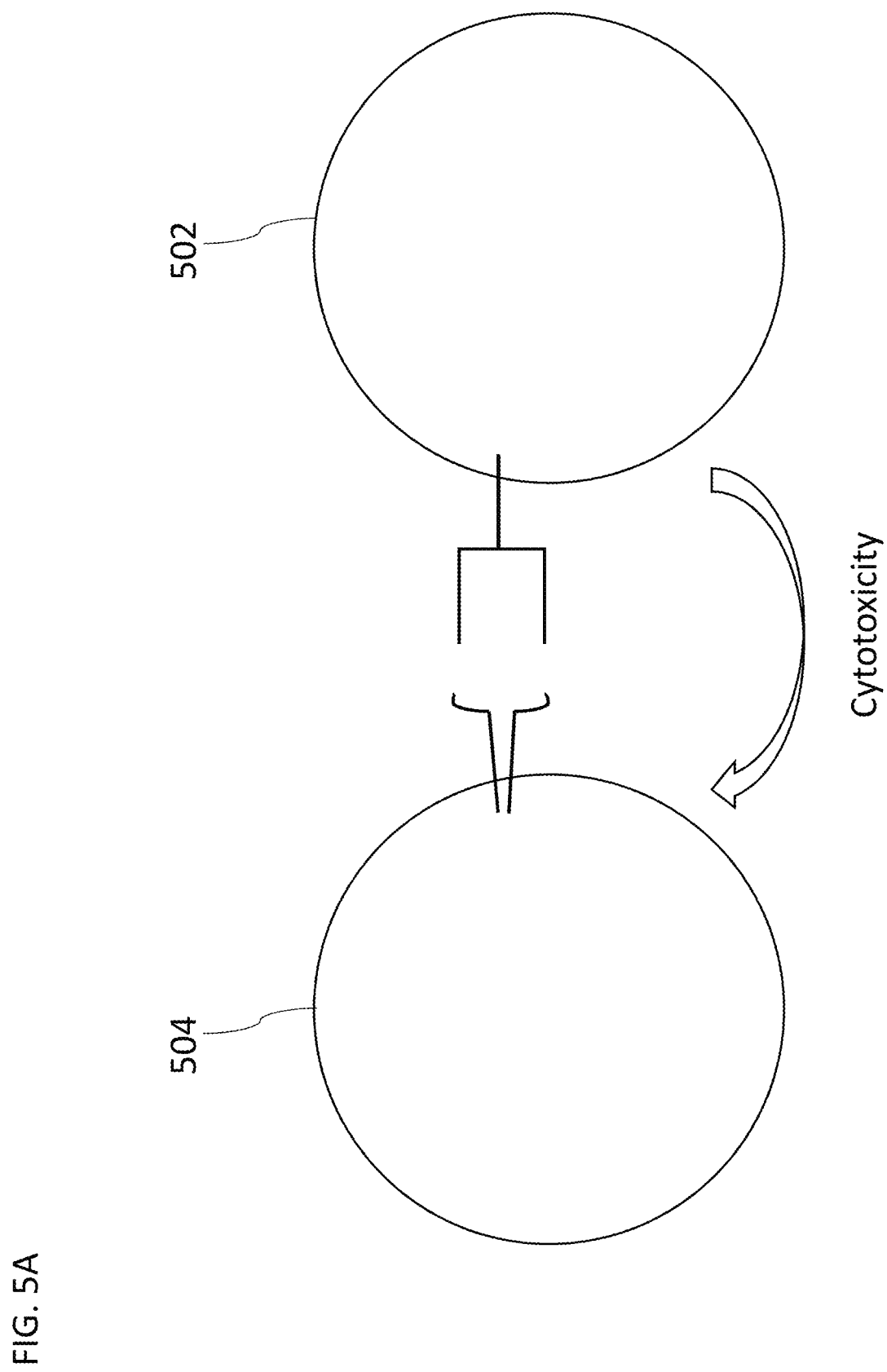
FIG. 5A illustrates a schematic describing an ability of SABRs to induce cytotoxicity in response to recognition of particular T cell antigenic specificities according to various embodiments herein.
Figure 5B:
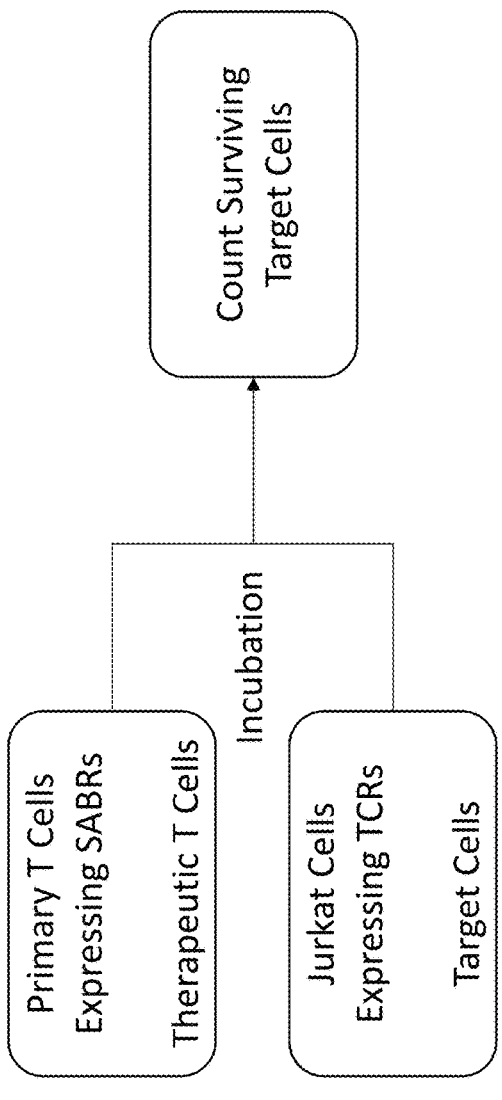
FIG. 5B illustrates a schematic describing a cytotoxicity assay used to test SABR-mediated cytotoxicity according to various embodiments herein.
Figure 5C:
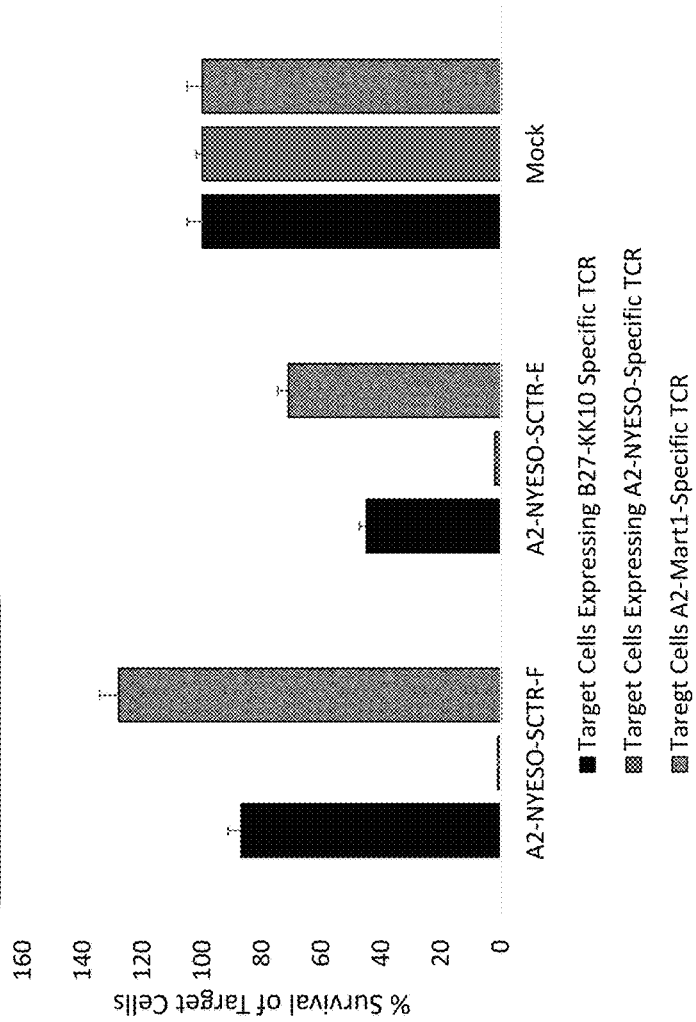
FIG. 5C illustrates a chart showing results demonstrating TCR specific cytotoxicity induced by A2-NYESO-SCTRs.

FIG. 5A illustrates a schematic describing the ability of SABRs to induce toxicity in response to recognition of particular T cell antigenic specificities according to various embodiments. In some embodiments, SABRs can also redirect T cell specificity to target other pathogenic T cells. As SABRs can induce signaling in T cells akin to CARs, they can be used to initiate a cytotoxic response towards T cells that recognize them. In some embodiments, a therapeutic T cell 502 transduced with SABRs recognizing a given antigen can be used to specifically eliminate pathogenic T cells 504 in a specific manner as described in FIG. 5A. In some embodiments, this ability can be tested using a cytotoxicity assay as described in FIG. 5B. In some embodiments, primary T cells can be transduced with two different A2-NYESO-SCTR constructs to allow their use as effector/therapeutic T cells. In some embodiments, Jurkat cells expressing A2-NYESO-, A2-MART1-, or B27-KK10-specific TCR can be used as target cells. In some embodiments, therapeutic T cells and target cells can be co-incubated and the survival of target cells can be measured after 24 hours. As described in FIG. 5B, A2-NYESO-SCTRs may be able to induce cytotoxicity specifically towards target cells expressing A2-NYESO-specific TCR, demonstrating the cytotoxic function of SABRs. In some embodiments, based on these results, SABRs can be used therapeutically to eliminate antigenic specificities from a T cell repertoire. In the case of, for example, autoimmune diseases, the pathogenic T cells may be autoreactive T cells, which can be recognized by the SABR expressing their cognate autoantigen. In the case of, for example, T cell leukemia, the pathogenic T cells may be clonally expanded T cells, which can be recognized by the SABR expressing either their cognate antigen or a heteroclitic ligand recognized by them. In some embodiments, the specificity of SABRs allows them to target particular T cell specificities while not targeting the normal T cell repertoire.

In summary, in various embodiments described herein, SABRs can be used as a robust, scalable, specific, and versatile way to couple antigen presentation and signaling. In various embodiments, this function can be exploited in several different ways to understand and manipulate T cell specificities.

In certain embodiments, SABRs can be used for antigen discovery. Current technologies for antigen discovery include MHC multimers, functional assays, yeast display, mass spectrometry, and DNA barcoding/NACS. These technologies have several disadvantages including a lack of scalability, lack of ability to expand to many MHC alleles, need for specialized instrumentation, and lack of robustness. Moreover, all the current technologies focus on cancer-specific T cells, and MHC-I antigens. There is a severe dearth of approaches/strategies to identify MHC-II antigens.

MHC multimers are produced by synthesizing peptide epitopes and re-folding them with biotinylated MHC molecules. However, MHC multimers are limited to 10-100 antigens at one time are therefore are not scalable. Moreover, making multimers for MHC-II antigens is technically challenging due to their inherent instability. Functional assays such as ELISPOT also rely on synthesizing peptide epitopes and presenting them on target cells. While it has been a popular technology, the scale up to include numerous MHC-I and MHC-II alleles, as well as a broad range of epitopes is complex. Yeast display techniques use MHC-peptide presentation on yeast cell surface followed by staining the yeast using a soluble TCR. Production of soluble TCRs is highly non-robust and time consuming, and therefore not easily scalable. Mass spectrometry techniques identify prospective antigenic epitopes based on mass spectrometry of antigen presenting cells. However, mass spectrometry requires a large amount of tissue, which is difficult to obtain for many diseases such as Type 1 Diabetes. Moreover, it also requires validation based on MHC multimers. Finally, DNA barcoding/NACS uses specialized barcoded MHC multimers that are immobilized on chips or beads. While effective, this technique is limited by the requirement for specialized equipment to capture cells and read their barcode, and by the inability to handle multiple sample at once.

Some embodiments herein are directed to novel technologies for discovering and validating antigen reactivity of T cells. T cells are an essential part of the adaptive immune system that fights infections and cancers. T cells use their surface TCR to recognize antigenic peptide epitopes presented by MHC proteins. Antigens displayed on MHC can be either from pathogens (e.g. peptides from Influenza virus), from cancerous cells (e.g. MART1/MelanA peptide expressed on Melanoma cells), or from normal cells (e.g. ProInsulin peptide from normal pancreatic cells). T cell responses are protective in their normal form but can be pathogenic if dysregulated.

T-cells are essential for immunity against viral infections and cancers but can cause autoimmune diseases like Type 1 Diabetes if they become dysfunctional. One of the biggest challenges in studying T cells is in the discovery of the specific protein antigens they recognize. In some embodiments, SABRs can be used to present protein antigens and induce a readable output of a T cell that recognizes them. In some embodiments, this ability of SABRs can solve the challenge of antigen identification and benefit the development of T cell mediated therapies. Some embodiments herein relate to using SABR technology for use in antigen discovery in numerous diseases including, for example, cancers, Type 1 Diabetes, multiple sclerosis, HIV/AIDS, and others. For example, FIG. 19 illustrates antigenic epitopes that, when combined with the SABR technology herein, could be useful in treatment of type 1 diabetes.

Protective cell responses, such as those towards pathogens or cancers, are manipulated for prevention/therapy via vaccines or immunotherapies. Dysfunctional T cell responses specific for autoantigens can be pathogenic, such as those targeting normal pancreatic cells in Type 1 Diabetes. Two types of T cells mediate the immune response: CD8+ T cells that recognize 8-12 residue long peptides presented on class I MHC (MHC-I) molecules and initiate direct killing of infected or cancerous cells, and CD4+ T cells that recognize 12-17 residue long peptides presented on class II MHC (MHCII) molecules and provide immunologic help to CD8+ T cells. Both CD8+ and CD4+ T cells play important roles in protective and pathogenic immunity. Understanding the antigens targeted by these cells is an important factor for manipulating these responses. There is a growing need for technologies to identify and validate targeted antigens.

Various embodiments herein are directed to novel technologies to identify and/or validate antigenic epitopes targeted by a given T cell. In some embodiments, the technology relies on synthetic proteins called SABRs.

In some embodiments, SABRs perform various functions including presenting an antigenic epitope via an extracellular MHC domain and initiating a readable cellular signal upon recognition of that epitope via an intracellular signaling domain. In some embodiments, by combining these two functions, SABRs can present an antigen, and then transduce a signal if a T cell recognizes that antigen. In some embodiments, the transduced signal is converted to a readable output, such as expression of a reporter gene, e.g. GFP, to mark a recognized cell.

In some embodiments, the various abilities of SABRs described herein can be used to screen for or validate reactivity to a given antigen, similar to ELISPOT assays. Example uses of this strategy according to various embodiments include monitoring vaccine/disease induced T cell responses in Influenza infection and screening for pathogenic autoreactive T cells in Type 1 Diabetes. Alternatively, in some embodiments, libraries of SABRs presenting numerous antigens can be constructed to identify antigens recognized by T cells of unknown specificity. Example uses of this strategy according to various embodiments include identification of tumor antigens recognized by tumor infiltrating lymphocytes and identification of neoantigen-specific T cell responses in cancer patients.

In accordance with various embodiments herein, The SABR technologies present major advantages over existing technologies including scalability, ease of use, ability to identify MHC-II antigens, and easier commercialization. Therefore, in some embodiments, SABR technology can be used into a commercial method or kit that can enable T cell antigen discovery, diagnostics, and validation for infectious diseases, cancers, and autoimmune diseases. In some embodiments, the SABR technology can be commercialized include pre-packaged lentiviral vectors to express SABRs and cell-based libraries expressing SABRs.

Advantages of SABR Technology

In some embodiments, the SABR library technology described herein has multiple advantages. In some embodiments, the SABR libraries described herein can be built at a flexible scale, from, for example, 1 to $10^6$ antigens or more, 100, 200, 300, 400, 1000, or more antigens in a library, depending on the disease in question. In some embodiments, the library can include hundreds of antigens for identifying a full protein's epitope, a couple of thousand antigens for diseases (neoantigen, listeria), or hundreds of thousands of antigens for broad identification Moreover, in some embodiments, this scale up/down can be performed in a standard immunology laboratory without the need for specialized equipment. SABR libraries can also be built for any given number of MHC alleles, making it easier to toggle between universal or patient-specific antigen libraries. Additionally, in some embodiments, the intended product and its use is in a format that requires routine laboratory procedures. Therefore, the turnaround time for using the product can be as low as 3-5 days. Furthermore, unlike yeast display or DNA barcoding, the SABR technology can be used on multiple samples at a time, increasing the throughput. Finally, in some embodiments, SABR libraries can be built for both MHC-I and MHC-II antigens, unlike the current technologies, which are restricted largely to MHC-I antigens. In some embodiments, this versatility allows the use of the SABR technology to a large number of autoimmune diseases.

In some embodiments, The SABR technology may have a significant cost advantage over other approaches. In some embodiments, the implementation of the technology does not require the use of any specialized equipment that a standard immunology laboratory would not have. For instance, in some embodiments, a flow cytometry-based cell sorter and access to Illumina sequencing facilities is sufficient to implement the technology in an academic/industrial laboratory. Current technologies are limited by the need for specialized equipment, for instance, access to Mass Spectrometer (MS), or specialized chips for DNA barcoding/NACS. Also, in some embodiments, unlike other technologies, the SABR technology does not require synthesizing any specialized reagents that are critical to its implementation. For example, yeast display technology requires synthesizing a soluble TCR, which is highly non-robust and requires time consuming/expensive protein purification. In some embodiments, SABRs are used in simple cell-based assays which can be performed in a general BSL2 laboratory setting. In some embodiments, the SABR technology offers a higher throughput because of its ability to process multiple samples at once. Most of the current technologies can handle only one patient sample at a time.

In some embodiments, the SABR technology can be manufactured on a mass scale. In some embodiments, the number of antigens that can be encoded in the library can be scaled up/down as per the requirements that are diseases/user specific. For example, a library for cancer neoantigens for patient-specific screening may encode for 6000 peptides, whereas a universal library for multiple class I HLA alleles may have ~$10^6$ peptides. In some embodiments, the scalability at this level is dependent on large scale oligonucleotide synthesis. In some embodiments, a given SABR library, for instance, can be around $10^5$-$10^6$ cells. In some embodiments, this number can be scaled up relatively easily, similar to commercially available cell lines.

Any one or more of the embodiments described herein can be combined with another one or more of the embodiments described below. Any one or more of the compositions described below can be combined or substituted into any one of the methods and/or mechanisms described below.

EXAMPLES

Example 1

SABRs, Peptide Fusion, Signaling Domain-MHC, MHC-Peptide Antigen

Figure 6A:
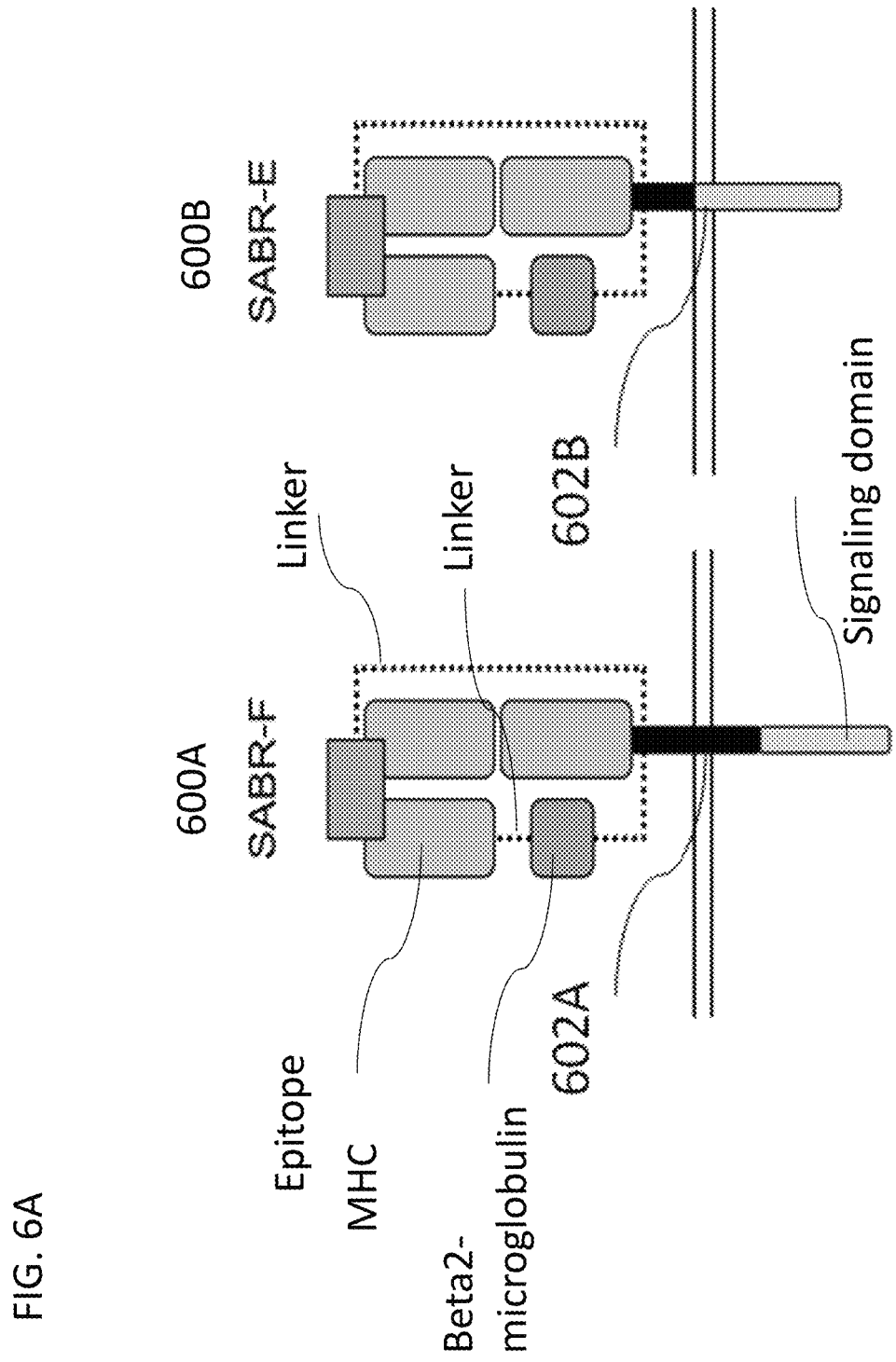
FIG. 6A illustrates schematics showing SABR-F and SABR-E constructs according to various embodiments herein.
Figure 6B:
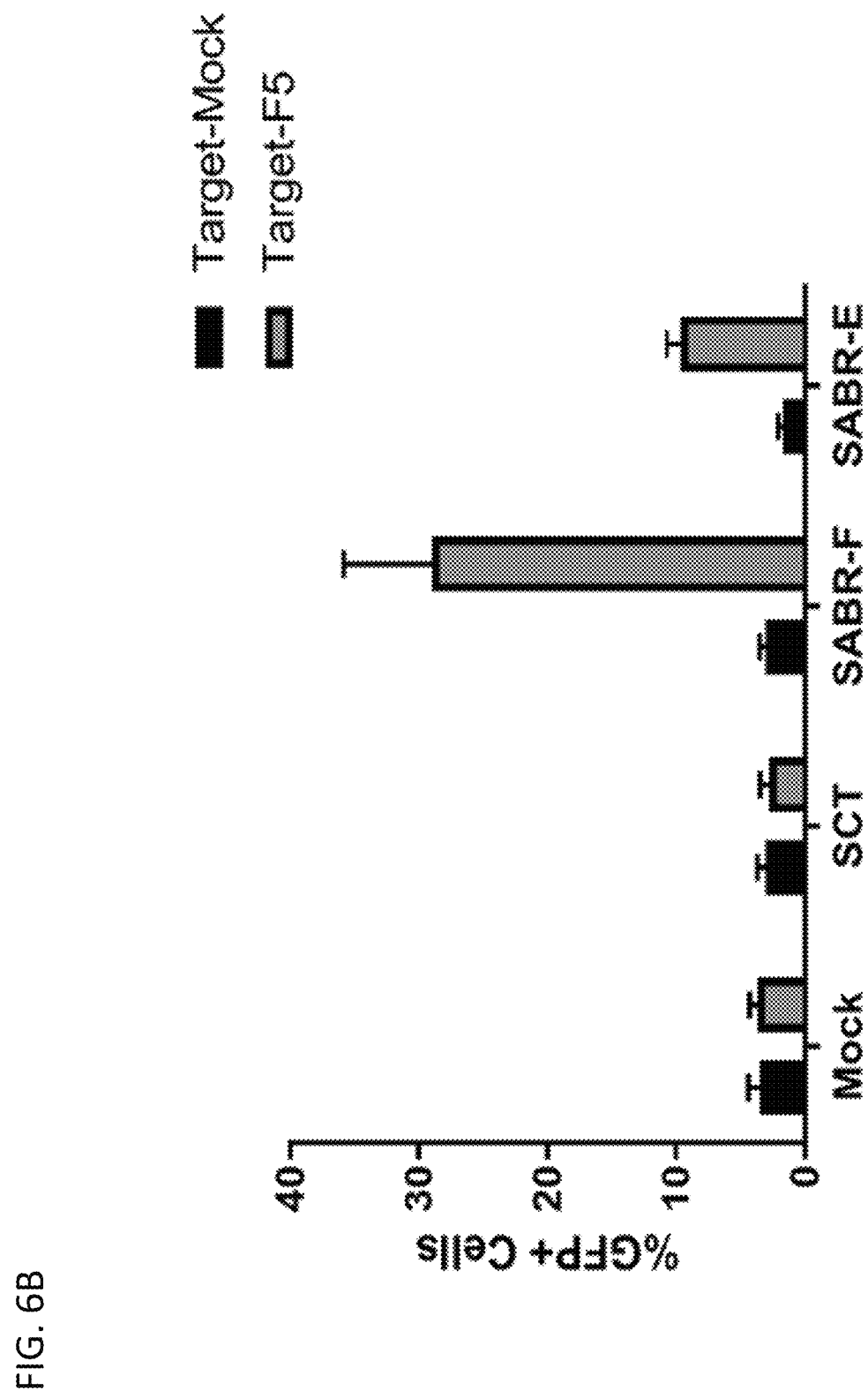
FIG. 6B illustrates a bar graph showing, on the Y-axis, % GFP+ cells at 8 hours in NFAT-GFP-Jurkats transduced with A2-MART1-SABRs and co-cultured with Jurkat cells transduced with TCRs.

T cell activation upon recognizing a target antigen induces detectable gene expression. However, as MHC molecules lack signaling domains, detection of recognized APCs is challenging. Fusing an intracellular signaling domain to pMHC complexes enables signal transduction. Chimeric receptors called SABRs were constructed. The extracellular domain of a SABR was a covalently linked peptide-β2microglobulin-MHC trimer, fused to an intracellular CD3ζ signaling domain with a CD28 co-stimulatory domain. Two variations of SABRs, SABR-F and SABR-E, were constructed which contained the entire MHC molecule or only the extracellular part of the MHC molecule respectively, as seen in FIG. 6A. FIG. 6A illustrates schematics showing the SABR-F and SABR-E constructs according to various embodiments. SABR-F 600A contains the transmembrane domain 602A from HLA, whereas SABR-E 600B contains the transmembrane domain 602B from CD3ζ. The two horizontal lines indicate two leaflets of the plasma membrane. FIG. 6B illustrates a bar graph showing, on the Y-axis, % GFP+ cells at 8 hours in NFAT-GFP-Jurkats transduced with A2-MART1-SABRs and co-cultured with Jurkat cells transduced with TCRs. Co-culture assays were performed using 50,000 target cells and 50,000 effector cells. Within FIG. 6B, bars indicate mean±sd, n=12.

Upon interaction with a TCR, SABRs presenting its cognate antigen can induce an intracellular signal. FIG. 7A illustrates schematics demonstrating SABRs and TCR-pMHC specific signaling, with single chain trimer (SCT) and antigen (Ag). Within FIG. 7A, dotted lines indicate Gly-Ser linkers. An SCT without a signaling domain will not induce an intracellular signal in an antigen presenting cell when recognized by a TCR. Similarly, a SABR presenting an irrelevant antigen will not induce an intracellular signal when recognized by a TCR. However, a SABR presenting a cognate antigen will induce an intracellular signal when recognized by a TCR.

Figures 7B, 7C:
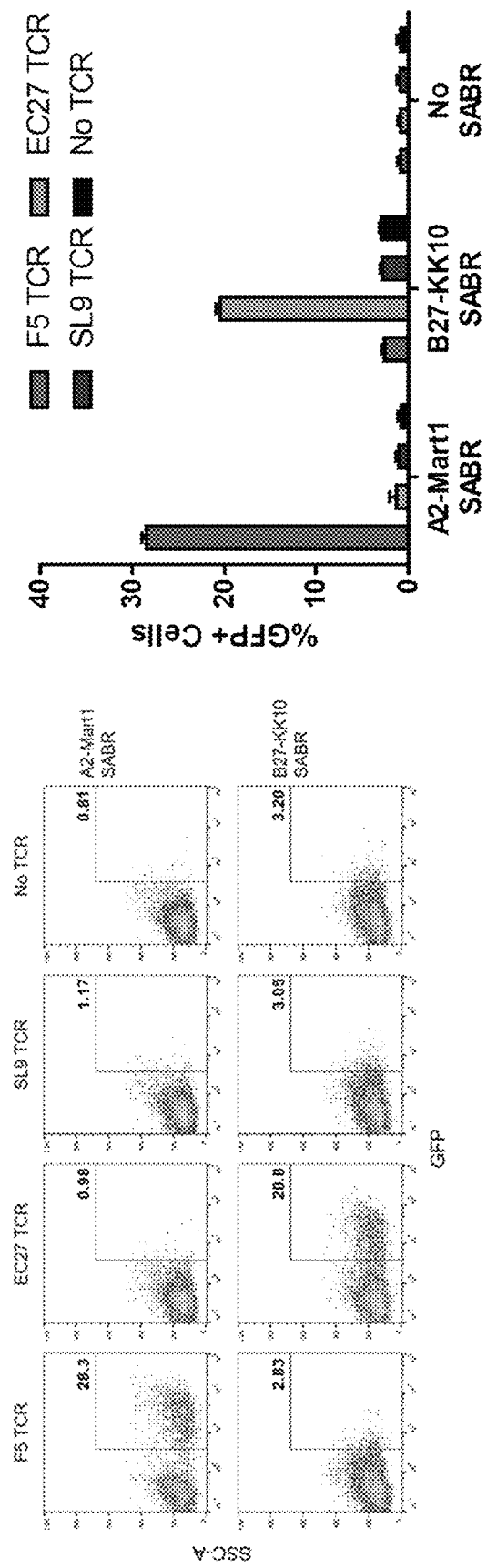
FIG. 7B illustrates representative flow cytometry plots from an experiment 8 hours from incubation.
FIG. 7C illustrates a bar graph of GFP expression by SABR transduced NFAT-GFP-Jurkat cells upon co-culture with TCR-transduced Jurkat cells.

To detect the signal induced by SABRs, NFAT-GFP-Jurkat cells were used, which express GFP upon receiving a signal via CD3ζ. NFAT-GFP-Jurkat cells were transduced with SABRs presenting the EAAGIGILTV epitope (from the MART1 protein) on HLA-A*0201 (hereafter known as A2-MART1-SABR) or the KRWIILGLNK epitope (KK10, from the HIV-1 Gag protein) from HIV-1 on HLA-B*2705 (hereafter known as B27-KK10-SABR). NFAT-GFP-Jurkat cells were co-incubated and transduced with Jurkat cells expressing TCRs and GFP expression was measured by flow cytometry after 8 hours. Specifically, F5 (recognizes A2-MART1), EC27 (recognizes B27-KK10), SL9 (recognizes A2-SLYNTVATL) TCRs or untransduced Jurkat cells were used. Robust GFP expression was detected only in co-culture assays with the cognate TCR-SABR-F pairs. FIG. 7C illustrates GFP expression by SABR transduced NFAT-GFP-Jurkat cells upon co-culture with TCR-transduced Jurkat cells. Within FIG. 7B, the Y-axis shows % GFP+ cells in co-culture assays performed with 10,000 effector and 10,000 target cells at 8 hours after co-culture. In FIG. 7C, bars indicate mean±sd, n=3. FIG. 7B illustrates representative flow cytometry plots from assays of FIG. 7C. Within FIG. 7B, frequency of GFP+ cells are indicated as a percentage.

The SABR-F construct showed higher signal than SABR-E construct, and therefore, was used for further experiments. To test if SABRs can detect T cell specificities in a polyclonal population, a number of Jurkat cells expressing F5 TCR were titrated with untranduced Jurkat cells and co-incubated them with NFAT-GFP-Jurkat cells expressing A2-MART1-SABR. SABR signaling was titratable and sensitive enough to detect at least as low as 10 F5+ Jurkat cells mixed with 10,000 mock-transduced Jurkat cells.

FIG. 7D illustrates a graph of detection of low cell numbers by SABRs. Within FIG. 7D, the Y-axis shows number of GFP+ cells in co-culture assays performed with 10,000 effector and 10,000 target cells at 8 hours after co-culture. The X-axis shows the number of F5+ Jurkat cells mixed with untransduced Jurkat cells. Within FIG. 7D, bars indicate values for n=1. FIG. 7E illustrates a timecourse of GFP expression by A2-MART1-SABR transduced NFAT-GFP-Jurkat cells co-cultured with F5-transduced Jurkat cells. The Y-axis shows % GFP+ cells in co-culture assays performed with 50,000 effector and 50,000 target cells. Within FIG. 7E, dots indicate mean±sd, n=3.

Figure 7F:
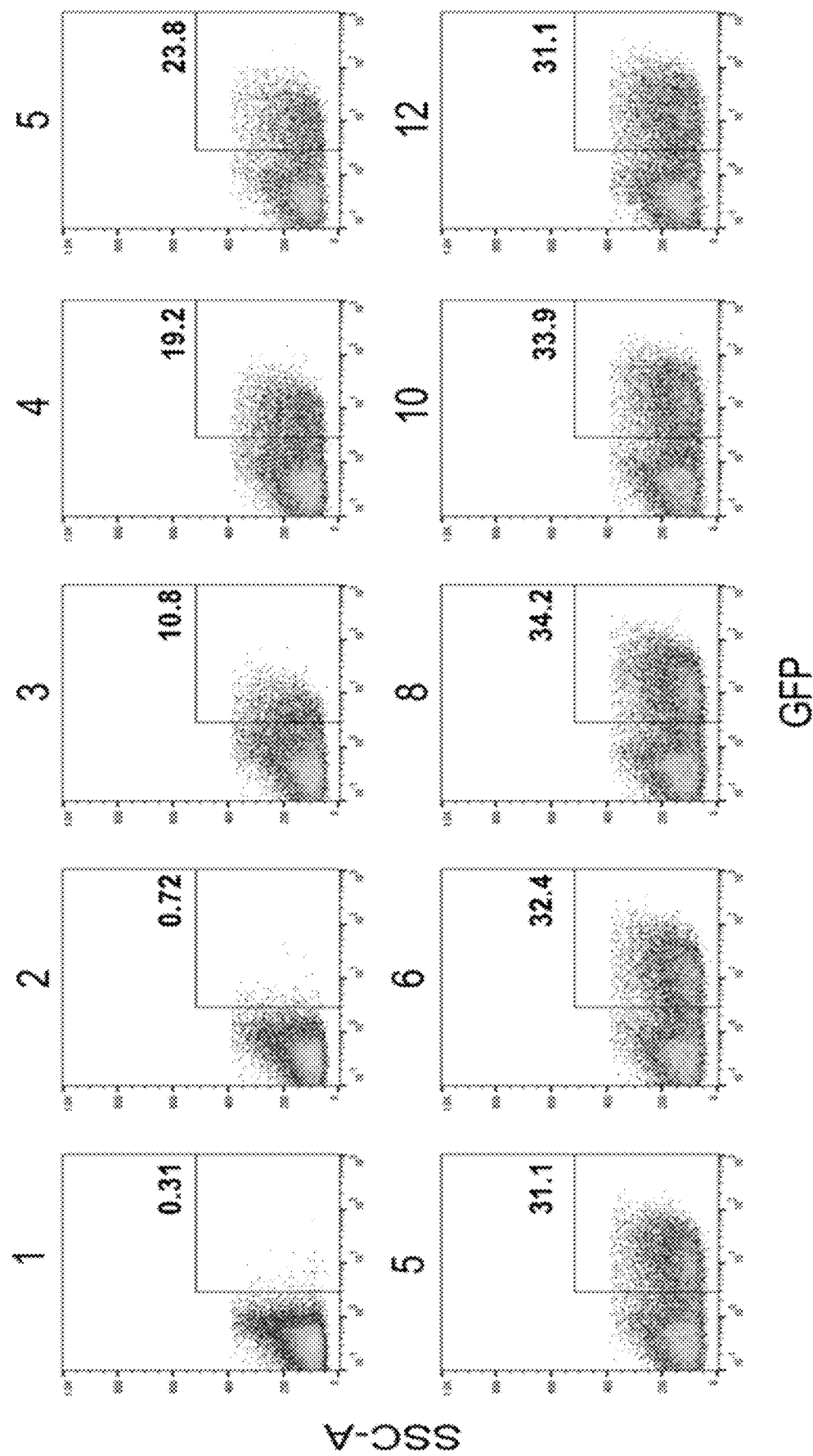
FIG. 7F illustrates representative flow cytometry plots from the experiment of FIG. 7E.

SABR signaling was also rapid, as GFP signal was detectable within 3 hours of co-incubation, and reached saturation within 6-8 hours, as shown in FIG. 7E and FIG. 7F. FIG. 7F illustrates representative flow cytometry plots from the experiment enumerated in FIG. 7E. Within FIG. 7F, the rectangle in the right bottom corners shows the gate for counting GFP+ cells. The time at which each sample was collected is shown as hours. The frequency of cells in the GFP+ gate is indicated as a percentage.

Taken together, these results show that SABRs can induce signaling upon successful and specific TCR-pMHC interaction, allowing identification of recognized APCs.

Example 2

SABRs Allow Different Modes of Antigen Presentation

Figure 8A:
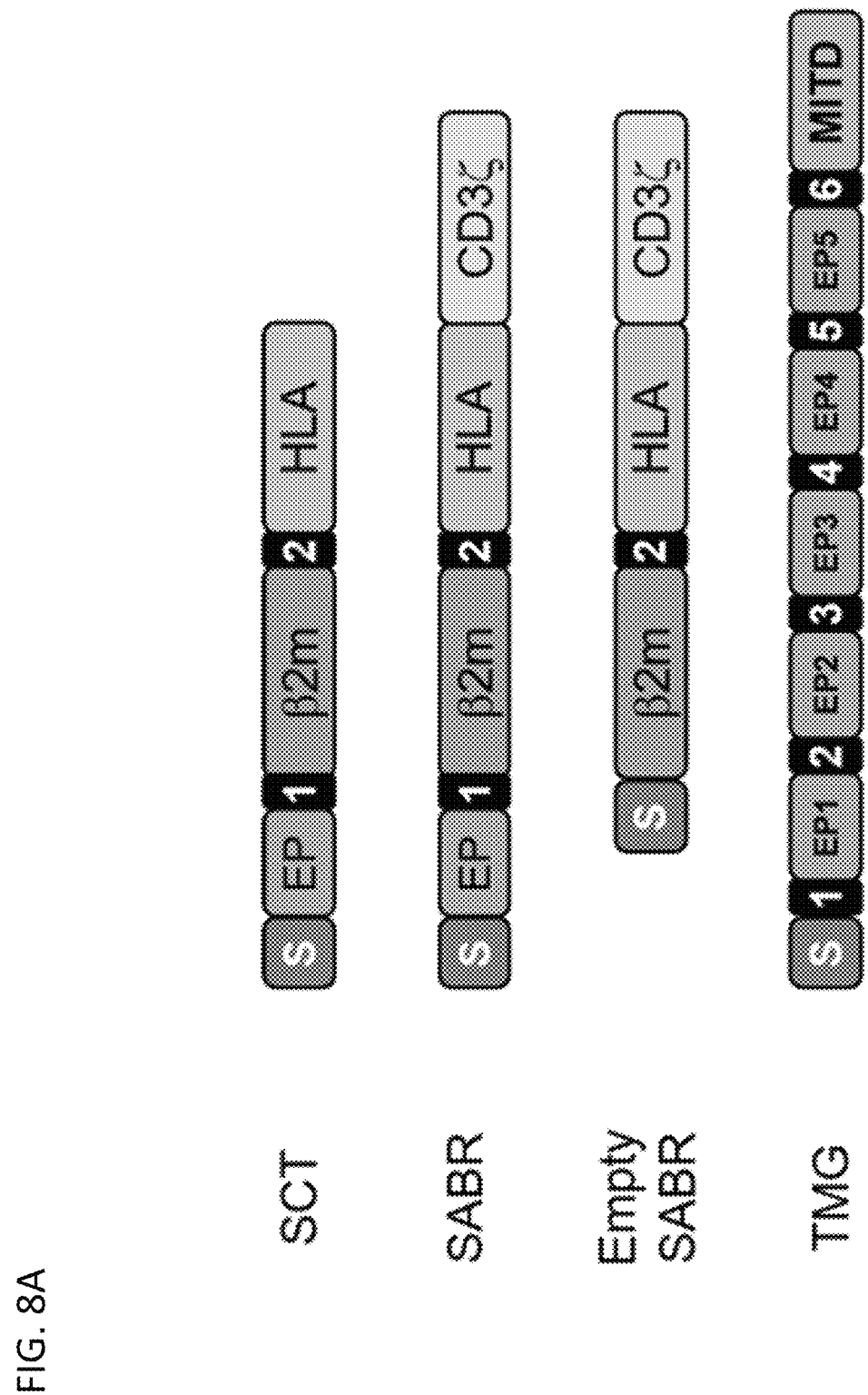
FIG. 8A illustrates a schematic showing SCT, SABRs, empty SABRs, and tandem minigenes (TMGs) according to various embodiments.
Figure 8B:
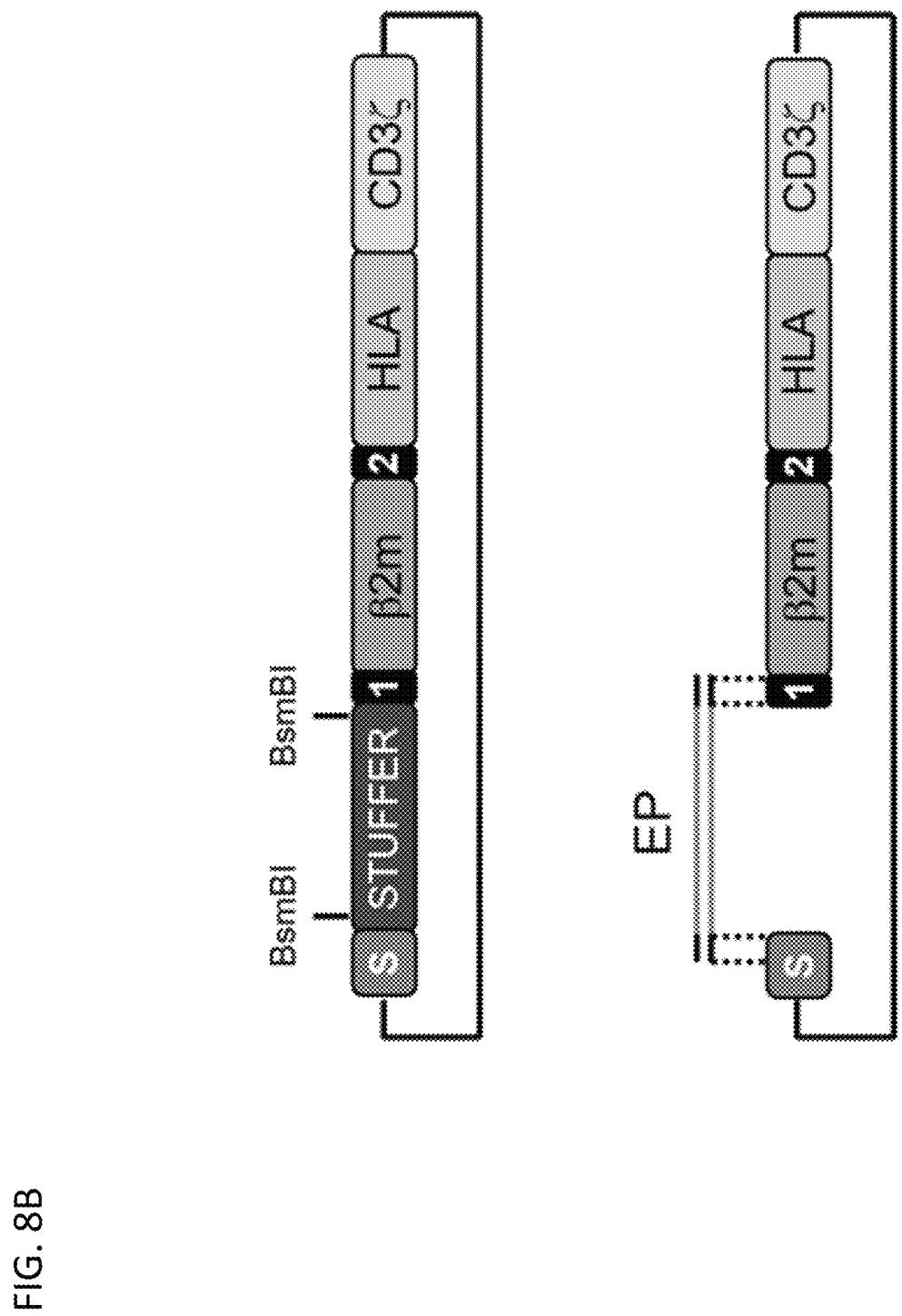
FIG. 8B illustrates SABR vector constructs with a stuffer fragment showing BsmBI sites, and a cloning strategy using double stranded oligonucleotides with encoding an epitope flanked by overlaps according to various embodiments.
Figure 8C:
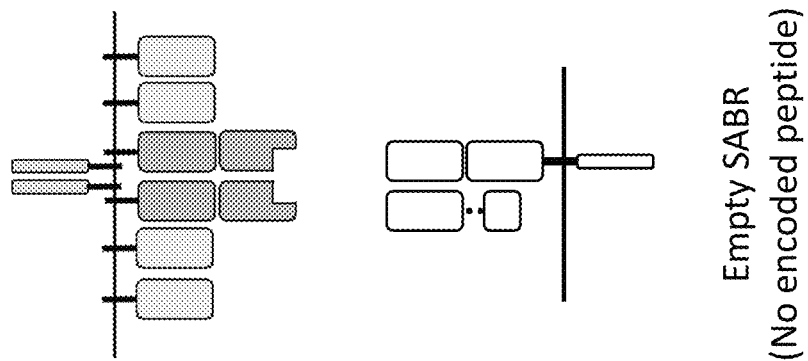
FIG. 8C illustrates an empty SABR construct according to various embodiments.
Figure 8D:
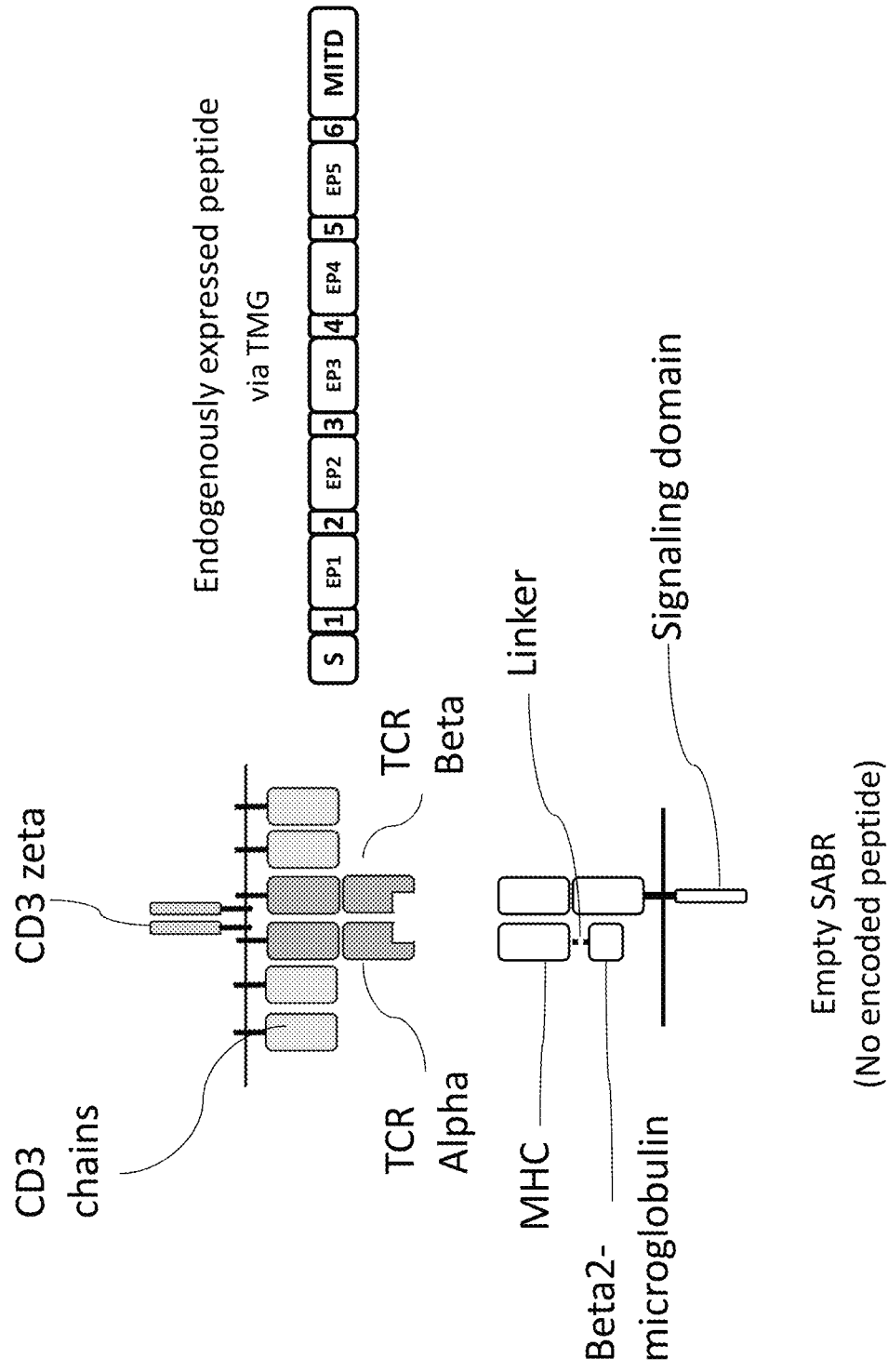
FIG. 8D illustrates an empty SABR (i.e. no encoded peptide) and endogenously expressed peptide according to various embodiments herein.

The endogenous MHC complexes described above present epitopes from newly translated proteins or endocytosed proteins via cross-presentation. To test if SABRs can also utilize these pathways for antigen presentation, an 'empty' version of SABRs was constructed that linked β2-microglobulin with A2 or B27 but did not genetically encode for an epitope. FIG. 8A illustrates a schematic showing SCT, SABRs, empty SABRs, and tandem minigenes (TMGs) according to various embodiments, with epitope (EP), signal sequence (S), and MHC class I trafficking signal (MIHC). Within FIG. 8A, numbers 1-6 indicate Gly-Ser linkers. FIG. 8B illustrates SABR vector constructs with a stuffer fragment showing BsmBI sites, and a cloning strategy using double stranded oligonucleotides with encoding the epitope flanked by overlaps according to various embodiments. FIG. 8C illustrates an empty SABR construct according to various embodiments. FIG. 8D illustrates an empty SABR (i.e. no encoded peptide) and endogenously expressed peptide according to various embodiments herein.

SABR-APCs were incubated with soluble peptides to test presentation and recognition of those peptides. FIG. 8E illustrates a schematic of empty SABRs pulsed with exogenous peptide. NFAT-GFP-Jurkat cells expressing the empty SABRs were incubated with soluble MART1 or KK10 peptides and co-cultured them with Jurkat cells expressing F5 or EC27 TCRs.

FIG. 8F illustrates a graph showing GFP expression by NFAT-GFP-Jurkats transduced with empty SABRs pulsed with soluble MART1 or KK10 peptides and co-cultured with Jurkat cells transduced with F5 or EC27 TCRs. The Y-axis shows % GFP+ cells in co-culture assays performed with 10,000 effector and 10,000 target cells at 8 hours after co-culture. The bars indicate mean±sd, n=3. Both A2 and B27 empty SABRs induced a signal only in presence of the soluble peptide corresponding to the TCRs, and not in presence of mismatched peptide or in absence of soluble peptide. Moreover, the signal induced by correct peptide-TCR combinations was comparable to the signal induced by the corresponding SABRs presenting covalently linked epitopes.

Figure 8H:
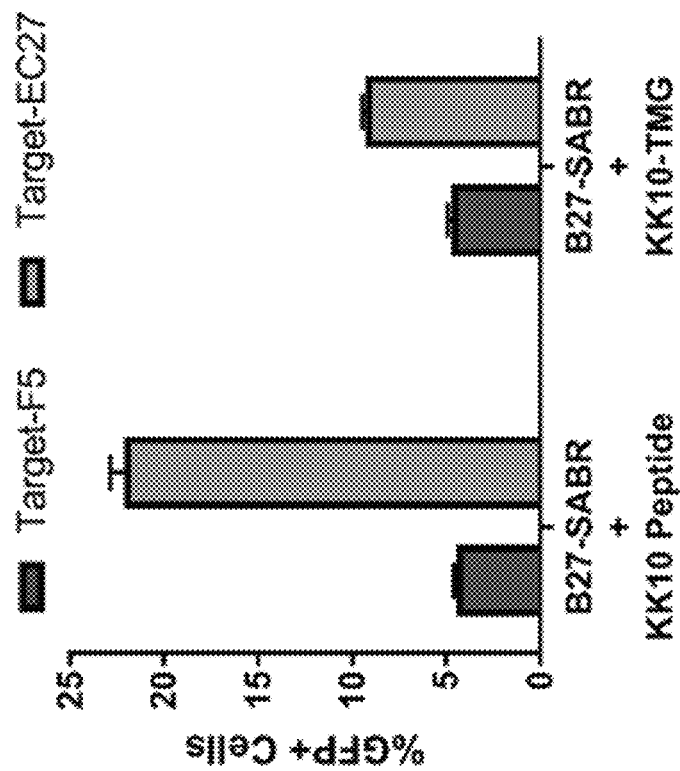
FIG. 8H illustrates a graph of GFP expression by NFAT-GFP-Jurkats co-transduced with empty B27-SABRs KK10-TMG or transduced with empty B27-SABRs and pulsed with KK10 peptide, and co-cultured with Jurkat cells transduced with F5 or EC27 TCRs.
Figure 8G:
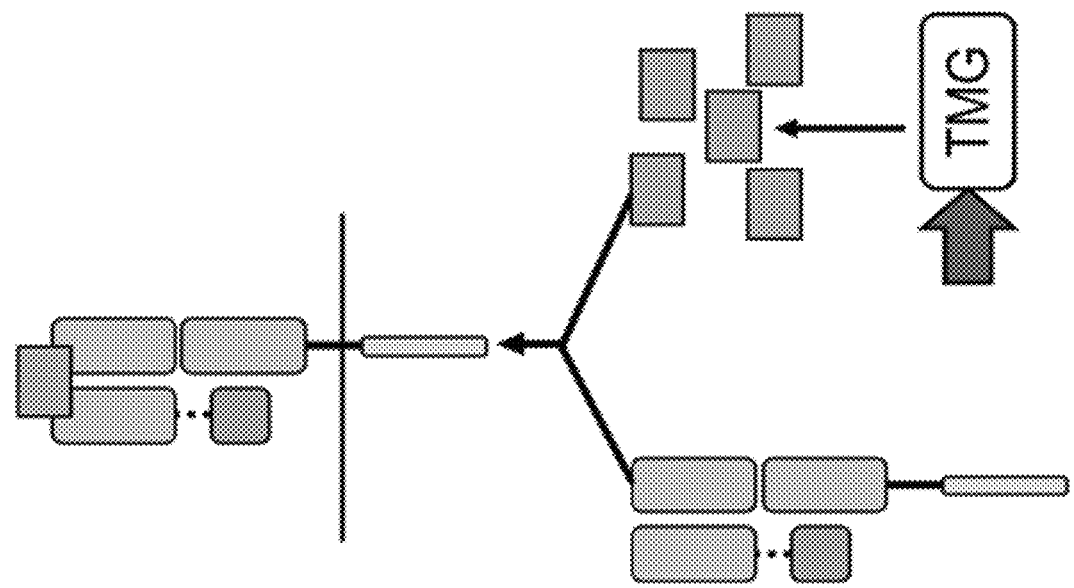
FIG. 8G illustrates a schematic of empty SABRs presenting newly translated epitopes with a TMG.

Endogenously processed peptide epitopes were tested to determine if they could be presented on 'empty' SABRs. Therefore, pentameric TMGs were constructed to express the KK10 epitope along with four irrelevant CMV-derived epitopes. FIG. 8G illustrates a schematic of empty SABRs presenting the newly translated epitopes, with a TMG.

NFAT-GFP-Jurkat cells were co-transduced with the empty B27-SABR and the KK10 TMG. Following co-incubation with EC27- or F5-expressing Jurkat cells, the 'empty' SABRs were able to present the endogenously expressed epitopes and induce specific signaling, as illustrated in FIG. 8H. FIG. 8H illustrates a graph of GFP expression by NFAT-GFP-Jurkats co-transduced with empty B27-SABRs KK10-TMG or transduced with empty B27-SABR and pulsed with KK10 peptide, and co-cultured with Jurkat cells transduced with F5 or EC27 TCRs. The Y-axis shows % GFP+ cells in co-culture assays performed with 50,000 effector and 50,000 target cells at 8 hours after co-culture. Within FIG. 8H, bars indicate mean±sd, n=3. However, the overall signal was lower than the corresponding empty SABRs were pulsed with soluble peptide. These results show that SABRs can present non-covalently linked epitopes generated through endogenous antigen processing and presentation pathways.

Figures 8I, 8J, 8K:
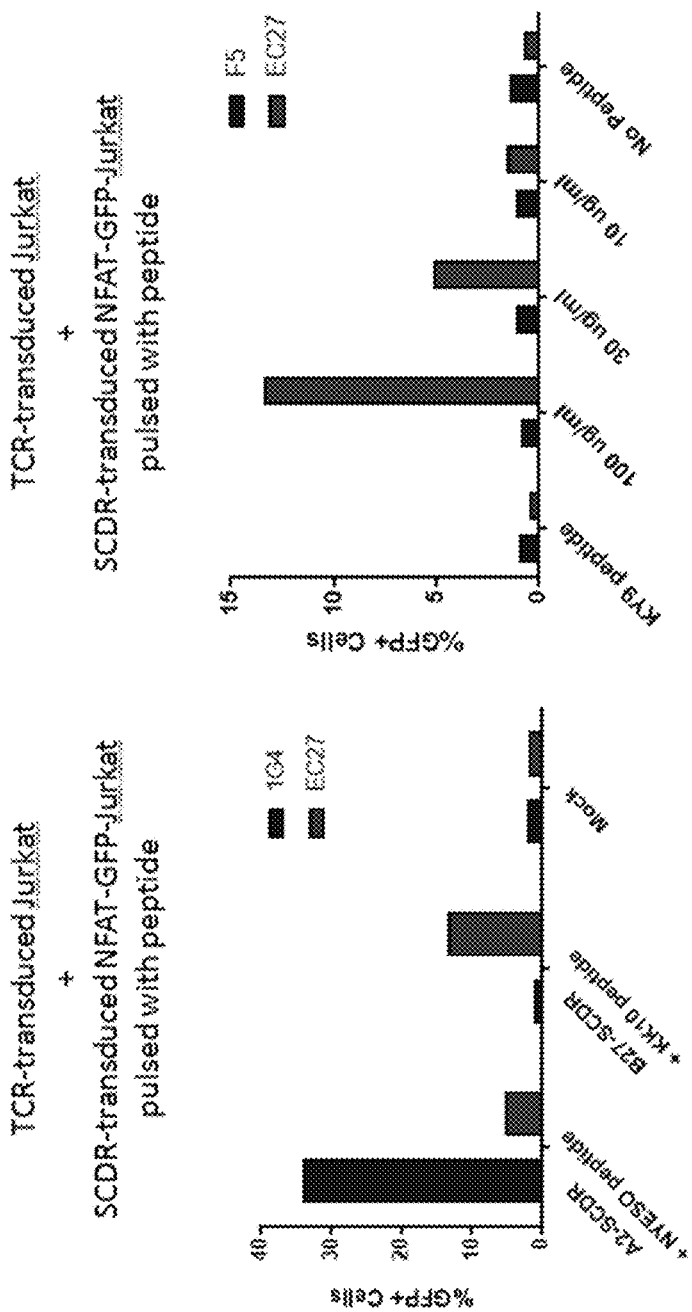
FIG. 8I illustrates an SCDR construct with a CD3z signal transduction domain according to various embodiments herein.
FIG. 8J illustrates a bar graph showing % GFP+ frequency for various TCR-peptide variations.
FIG. 8K illustrates a bar graph showing % GFP+ frequency for various TCR-peptide composition and concentration variations.

SABRs can present non-covalently linked epitopes generated through endogenous antigen processing and presentation pathways. FIG. 8I illustrates an SCDR construct with a CD3z signal transduction domain according to various embodiments herein. TCR-transduced Jurkat cells were incubated with the SCTR constructs and pulsed with peptide antigen. FIG. 8J illustrates a bar graph showing % GFP+ frequency for various TCR-peptide variations. FIG. 8K illustrates a bar graph showing % GFP+ frequency for various TCR-peptide composition and concentration variations. The results show that, like T cell signaling, SABR signaling is titratable with the amount of peptide presented.

Figures 8L, 8M:
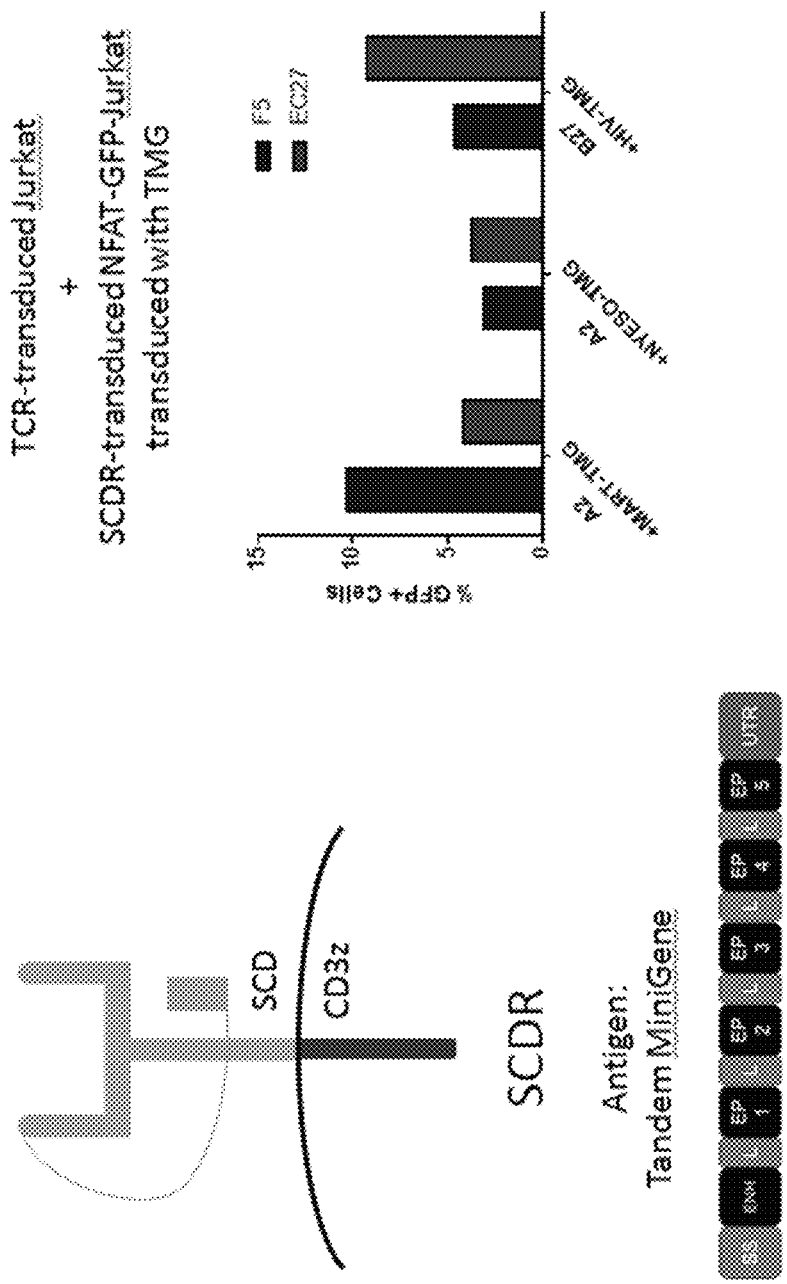
FIG. 8L illustrates a schematic showing an SCDR construct with a tandem minigene (TMG) antigen according to various embodiments herein.
FIG. 8M illustrates a bar graph showing % GFP+ frequency for various TCR-peptide variations.

FIG. 8L illustrates a schematic showing an SCDR construct with a tandem minigene (TMG) antigen according to various embodiments herein. TCR-transduced Jurkat cells were incubated with the SCTR-transduced NFAT-GFP-Jurkat cells transduced with TMG. FIG. 8M illustrates a bar graph showing % GFP+ frequency for various TCR-TMG variations. The results show that SABRs will present endogenous peptide (fragmented protein sequences derived from proteins in the cell) when not directly linked to an antigen.

Example 3

SABRs Initiating Bona Fide TCR Signal

To use SABRs as a therapeutic target, a SABR that binds to a pathogenic T cell in a patient can be identified. The SABR can be cloned into appropriate vectors for immunotherapy, such as lentiviral or retroviral vectors. The patient's own blood can be subjected to leukapheresis followed by isolation of T cells. The T cells can be activated and expanded using commercial methods such as using the OKT3 antibody. The expanded T cells can be transduced with the vector containing the SABR. The transduced cells can be reinfused into the patient as a therapeutic. The expanded T cells expressing the appropriate SABRs should target the pathogenic T cells in the patient and lead to elimination of the pathogenic T cells, leading to disease amelioration.

This can be done for type 1 diabetes, where a pathogenic T cell can target an insulin-derived epitope in the context of HLA-A2.1 (A2.1-Insulin). In this case, a SABR comprising of HLA-A2.1, presenting the Insulin epitope, and a signaling domain can be cloned into a lentiviral vector. The patient's own T cells can be expanded and transduced with the A2.1-Insulin-SABR expressing vector. The cells can be reinfused into the patient, where they can eliminate the pathogenic T cells that target A2.1-Insulin.

Figure 9A:
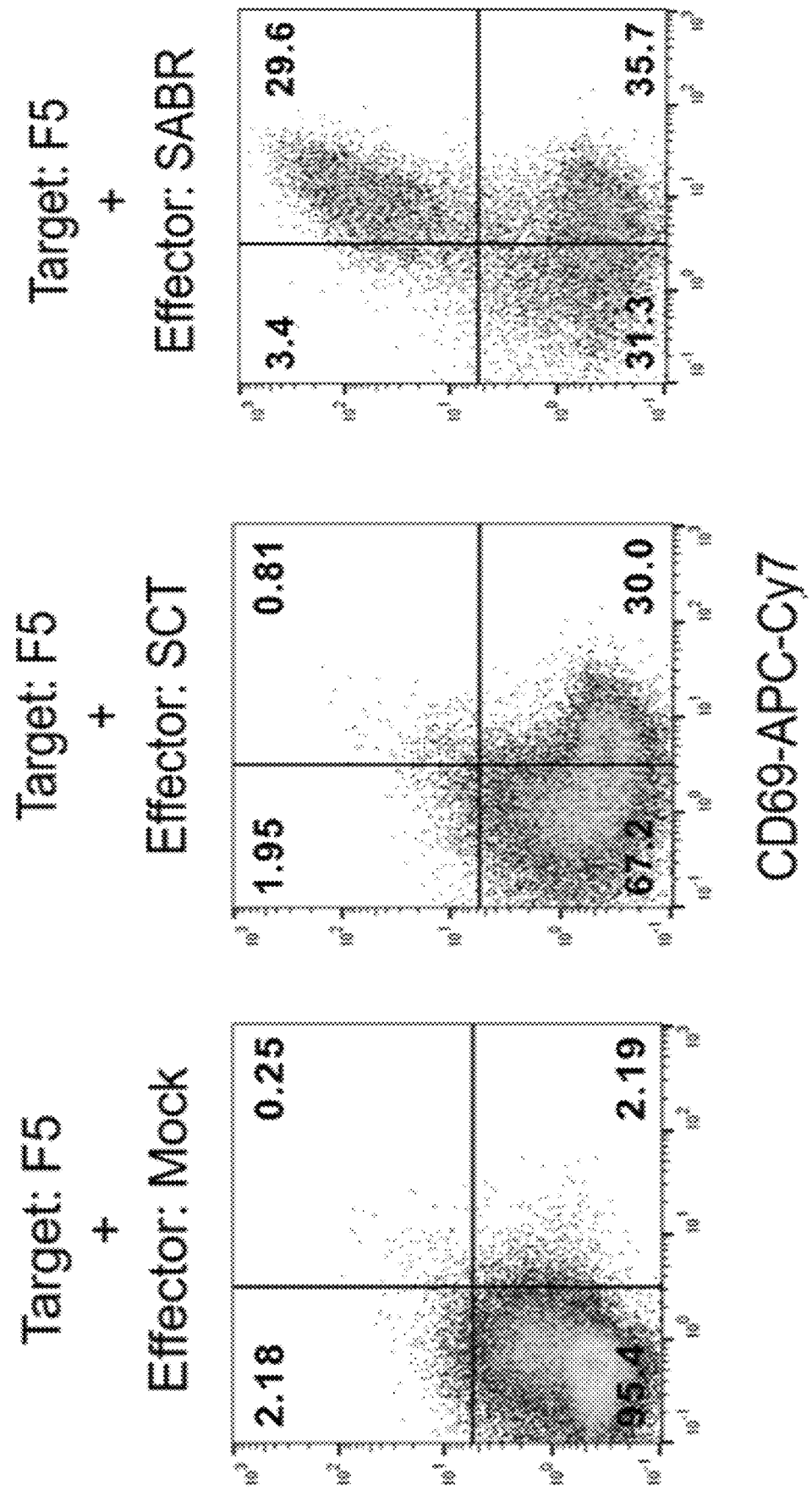
FIG. 9A illustrates representative flow cytometry plots of induction of CD69 by SABRs.

SABRs use a CD3ζ-CD28 domain for intracellular signaling, similar to chimeric antigen receptors (CARs) and TCRs. Therefore, intracellular signaling ability of SABRs is comparable to TCRs was tested. SABRs ability to induce early activation markers in NFAT-GFP-Jurkat cells was tested. NFAT-GFP-Jurkat cells transduced with the A2-MART1-SABR expressed CD69, an early T cell activation marker, upon co-culture with Jurkat cells transduced with F5 TCR. Co-expression of reporter-driven GFP and endogenous CD69 in cells expressing A2-MART1-SABR, but not the A2-MART1 single chain trimer implies that SABR signaling activates endogenous gene expression, as shown in FIG. 9A. FIG. 9A illustrates representative flow cytometry plots from one experiment of induction of CD69 by SABRs. GFP and CD69 expression in co-culture assays using 10,000 NFAT-GFP-Jurkat cells transduced with the indicated SABRs and 10,000 Jurkat cells transduced with F5 TCR is shown. The frequencies of cells in each gate are indicated as percentage.

Figure 9B:
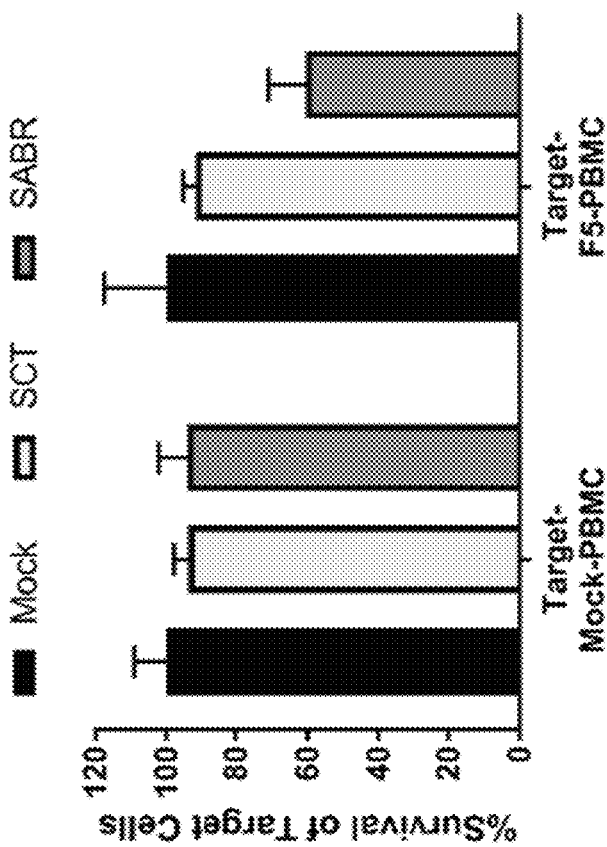
FIG. 9B illustrates a graph of cytotoxicity induced by SABR-expressing primary T cells against Jurkat cells.
Figure 9C:
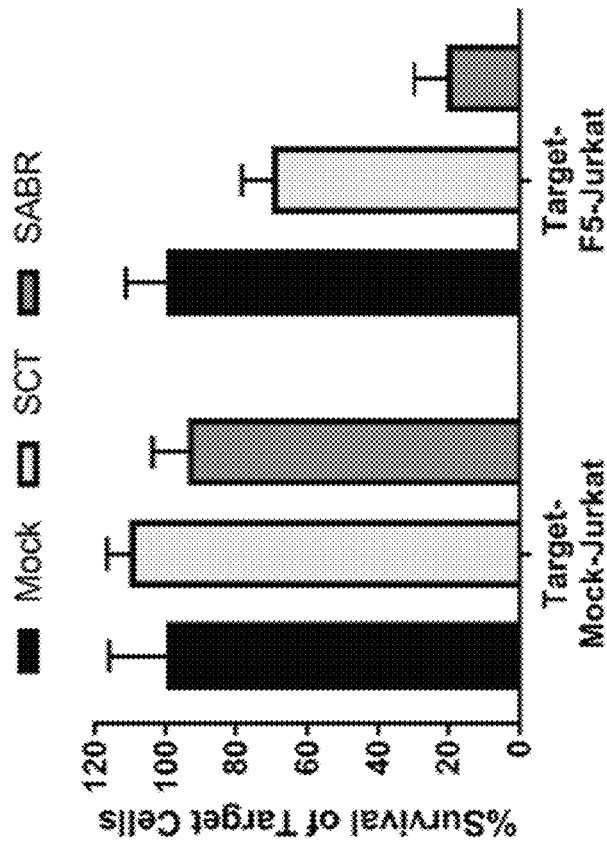
FIG. 9C illustrates a bar graph of cytotoxicity induced by SABR-expressing primary T cells against autologous target cells.

In some embodiments, if SABRs induce a bona fide TCR signal, they can confer cytotoxic capabilities to primary T cells. Activated primary T cells were transduced with A2-MART1-SABR and incubated with CFSE-labeled target cells expressing F5 TCR. Transduced primary T cells lysed Jurkat cells or primary T cells expressing the F5 TCR specifically, as shown in FIG. 9B and FIG. 9C. FIG. 9B illustrates a graph of cytotoxicity induced by SABR-expressing primary T cells against Jurkat cells. The Y-axis shows % survival of CFSE-labeled target cells at 24 hours after co-culture. Cytotoxicity assays were performed with 200,000 SABR-transduced cells and 50,000 TCR-transduced cells. With FIG. 9B, bars indicate mean±sd, n=8. FIG. 9C illustrates a bar graph of cytotoxicity induced by SABR-expressing primary T cells against autologous target cells. The Y-axis shows % survival of target cells at 24 hours after co-culture. Cytotoxicity assays were performed with 200,000 SABR-transduced cells and 50,000 TCR-transduced cells. Within FIG. 9C, bars indicate mean±sd, n=8.

Figure 9E:
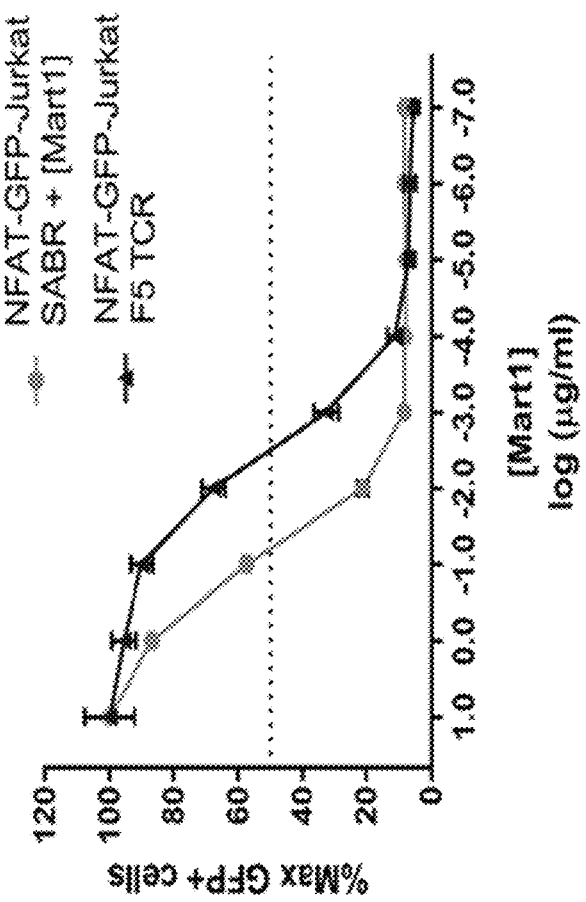
FIG. 9E illustrates a plot of antigen sensitivity of SABR and TCR signaling.
Figure 9D:
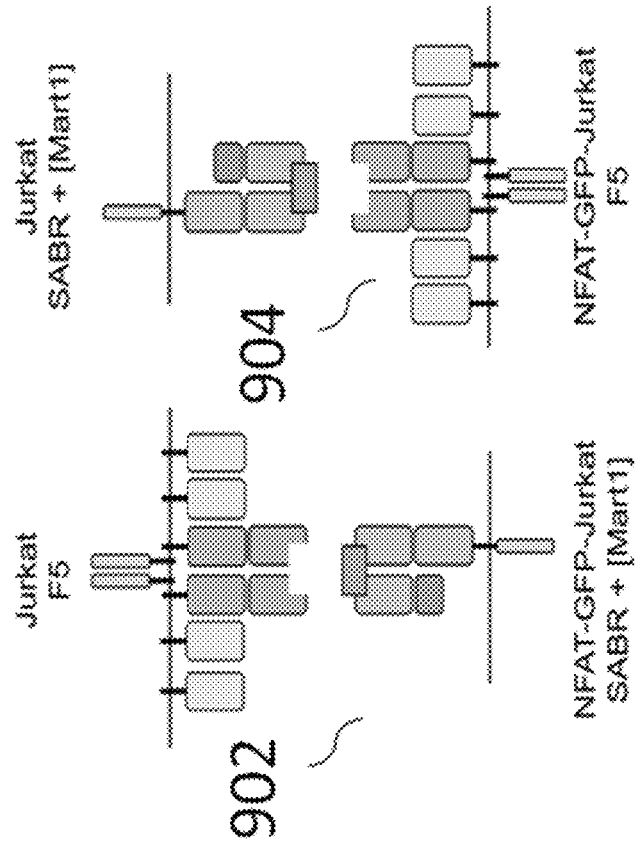
FIG. 9D illustrates a schematic of an assay to measure antigen sensitivity of A2-SABR and of F5-TCR.

The antigen sensitivity of SABRs and TCRs was compared. To that end, NFAT-GFP-Jurkat cells were transduced with either empty A2-SABR or F5 TCR and used as effectors. As targets, Jurkat cells transduced with A2-SABR or F5 TCR were used, as shown in FIG. 9D. FIG. 9D illustrates a schematic of the assay to measure antigen sensitivity of A2-SABR 902 and of F5-TCR 904.

Effectors were co-cultured with their cognate targets in presence of a range of concentrations of the MART1 peptide, and GFP expression was measured. Antigen sensitivity was determined as the concentration of the peptide required for half-maximal signaling. The antigen sensitivity of SABRs was 30-fold lower as compared to TCRs, as shown in in FIG. 9E. FIG. 9E illustrates a plot of antigen sensitivity of SABR and TCR signaling. The Y-axis shows % maximum of % GFP+ cells at 8 hours in co-culture assays using 50,000 SABR- or TCR-transduced cells pulsed with the MART1 peptide. The X-axis shows the concentration of the MART1 peptide used to pulse the cells. Within, FIG. 9E, dots indicate mean±sd, n=3. The dotted horizontal line indicates half-maximal signal.

Taken together, these results show that SABRs signal similar to TCRs, albeit, in some examples, with lower antigen sensitivity.

Example 3 above is also an example of SABRs as a therapeutic. For example, in a case where the F5 TCR can be substituted with a pathogenic TCR, such as a TCR recognizing type 1 diabetes antigens. In the therapeutic scenario, a similar experiment to show efficacy can be done where the SABR is presenting the antigen recognized by the pathogenic TCR. Primary T cells expressing the said SABR can then be used to induce cytotoxicity against the pathogenic TCR, and subsequently eliminate them for therapeutic benefit Example 4

Antigen Discovery using SABR Libraries

Figure 10A:
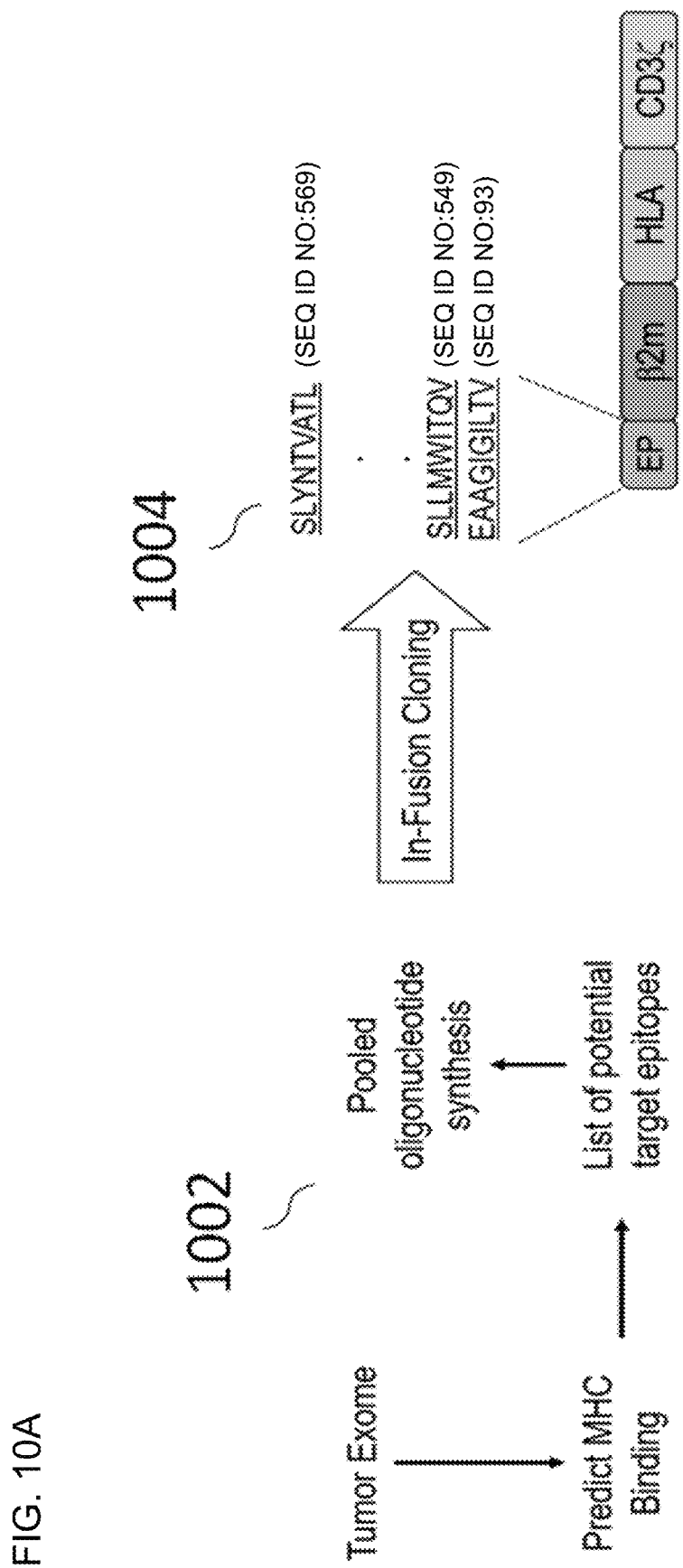
FIG. 10A illustrates a schematic showing a pipeline to construct custom SABR libraries according to various embodiments.

In some embodiments, by virtue of genetically linking the peptide epitope with MHC, SABRs can be used to present a defined antigen and to report its successful recognition by a TCR. Therefore, SABR libraries ability to present a large number of epitopes to be used to screen successful TCR-pMHC interactions was tested. A strategy to construct and use SABR libraries for T cell antigen discovery of 'orphan' antitumor TCRs with unknown antigens was created. First, a list of target epitopes was generated from an existing database or from tumor exome data followed by prediction of MHC binding. Pooled oligonucleotide libraries encoding for target epitopes were synthesized and cloned into the SABR plasmid, according to FIG. 10A. FIG. 10A illustrates a schematic showing the pipeline to construct custom SABR libraries according to various embodiments. The left panel 1002 shows the procedure to obtain and synthesize a list of epitopes. The right 1004 shows the schematic of the SABR library.

Figure 10B:
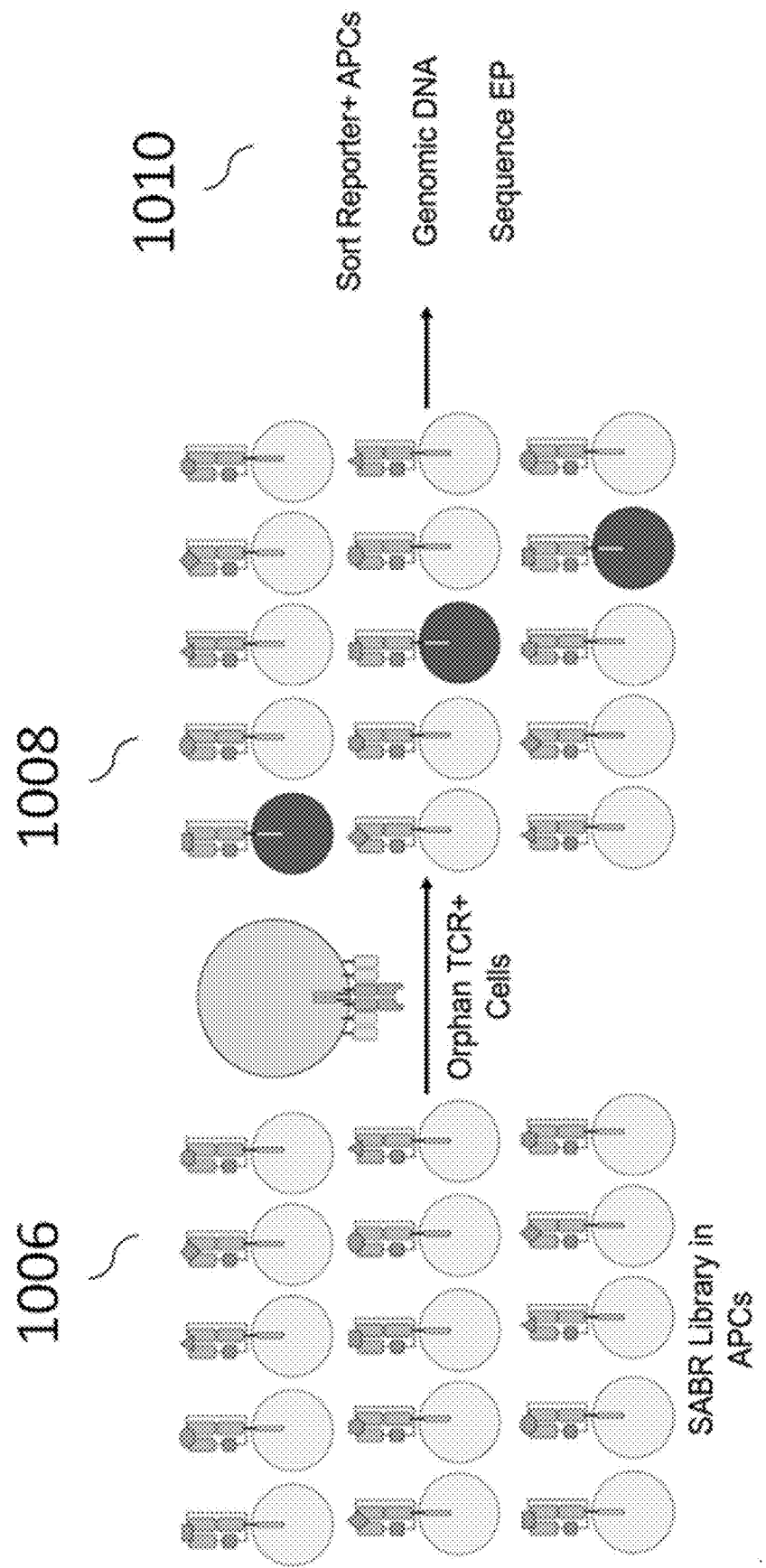
FIG. 10B illustrates a schematic showing a co-culture experiment to select cells from a SABR library that are recognized by an orphan TCR according to various embodiments.

The SABR libraries were packaged into lentiviral vectors and used to transduce NFAT-GFP-Jurkat cells. NFAT-GFP-Jurkat cells expressing the SABR library were co-cultured with Jurkat cells expressing an 'orphan' TCR. GFP+CD69+ NFAT-GFP-Jurkat cells were sorted using fluorescence activated cell sorting (FACS), followed by genomic DNA extraction. The epitope portion of the SABRs was amplified and subjected to high throughput sequencing, as shown in FIG. 10B. FIG. 10B illustrates a schematic showing the co-culture experiment to select cells from the SABR library that are recognized by an orphan TCR according to various embodiments. The left panel 1006 shows a SABR library presenting numerous unique epitopes. The middle panel 1008 shows cells APCs showing reporter expression induced by SABRs presenting the cognate epitope for the orphan TCR. The right panel 1010 shows processing steps of the selected cells.

Figure 10C:
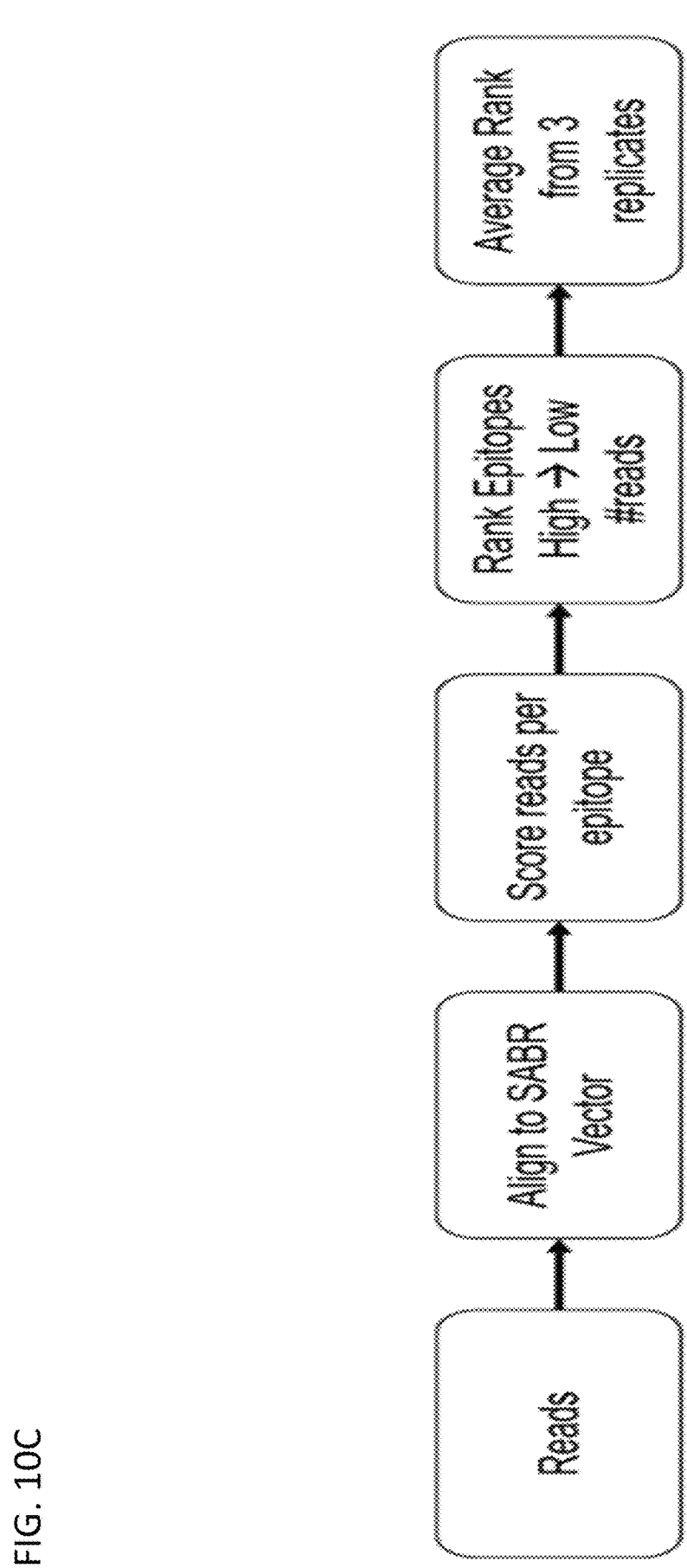
FIG. 10C illustrates a flowchart showing a computational analysis pipeline according to various embodiments.

The sequencing reads were aligned with the SABR vector backbone using Burrows-Wheeler alignment. Aligned reads were translated to reveal the epitope. The number of reads corresponding to each epitope was counted and reported in a list. A minimum of three replicates of the co-incubation assay were performed. For each replicate, a numerical rank was given to each epitope based on descending order of the number of reads. The rank from three replicates for each assay was averaged and reported as 'Average Rank', according to the flowchart in FIG. 10C. FIG. 10C illustrates a flowchart showing the computational analysis pipeline.

The top ranked epitopes were putative antigens for that TCR and are subsequently validated by constructing individual SABRs presenting each of the epitopes and measuring GFP expression in co-culture assays.

Figure 11A:
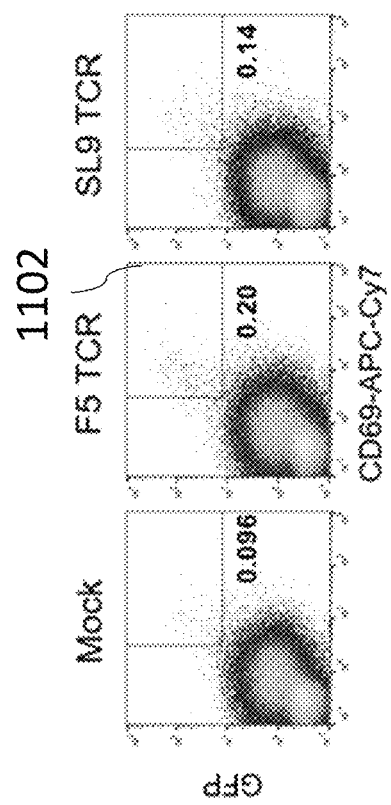
FIG. 11A illustrates representative flow cytometry plots.

To demonstrate proof-of-concept of the approach detailed in FIGS. 10A-10C, the SABR libraries ability to identify the cognate antigens of known public TCRs in an unbiased manner was tested. A SABR library encoding 12,055 epitopes presented on HLA-A*0201 (A2-SABR-library) consisting of all known HLA-A*0201-restricted epitopes from the Immune Epitope Database (IEDB) was constructed. The ability of the A2-SABR-library to identify the cognate antigen for two TCRs with known specificities (F5, which recognizes EAAGIGILTV, and SL9, which recognizes SLYNTVATL) was tested. NFAT-GFP-Jurkat cells were transduced with the A2-SABR-library and incubated with Jurkat cells expressing F5 or SL9 TCRs. After 10 hours of co-culture, GFP+CD69+ cells were sorted by FACS, the genomic DNA was extracted, the epitopes were sequenced, and average ranks for each epitope as described were calculated in FIGS. 10A-10C. FIG. 11A illustrates representative flow cytometry plots from one replicate. The A2-SABR library cells were sorted based on reporter gene expression. Co-culture assays using 9 million library cells with 9 million TCR-transduced Jurkat cells were set up. At 10 hours post co-culture, the cells were stained for CD69 and sorted using FACS. The rectangle 1102 in the top right corner of each flow plot shows the gate used for the sort. The frequency of cells in the sort gate is indicated as a percentage.

Figure 11B:
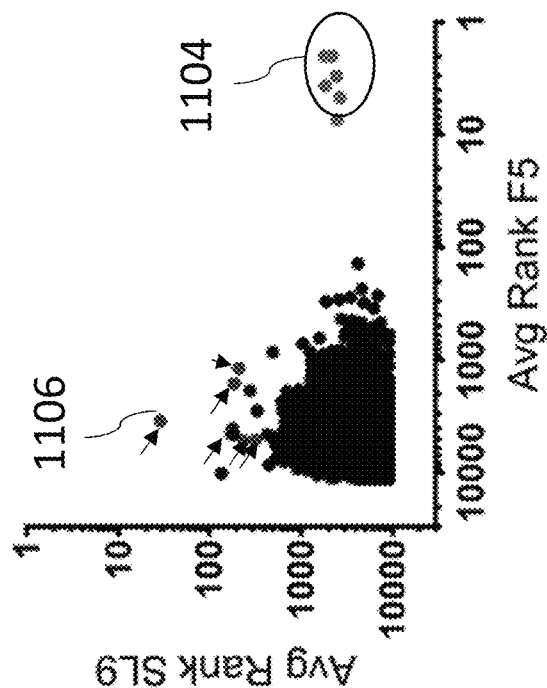
FIG. 11B illustrates a plot of average ranks from F5 and SL9 sorts.

The average ranks of each of the epitopes from the SL9 sort against those from F5 sort were plotted. FIG. 11B illustrates a plot of average ranks from the F5 and SL9 sorts. Within FIG. 11B, each dot represents the average rank for a unique epitope as calculated using the procedure described in FIGS. 10A-10C. The Y-axis shows the average rank in the SL9 sort, and the X-axis shows the average rank in the F5 sort. Dots 1104 indicate SEQ ID NO: 12174 analogs and dots 1106 indicate SEQ ID NO: 12194 analogs.

Six epitopes formed a distinct cluster by their rank in the F5 sort. In the SL9 sort, the top ranks were outliers, but did not form a separate cluster. FIG. 11C illustrates a plot of the average ranks for the top 24 hits from the F5 sort. The epitopes with asterisks indicate SEQ ID NO: 12174 analogs. The top six epitopes in the F5 sort were analogs of SEQ ID NO: 12174, indicating successful identification of its antigen, as shown in FIG. 11C.

Figure 11D:
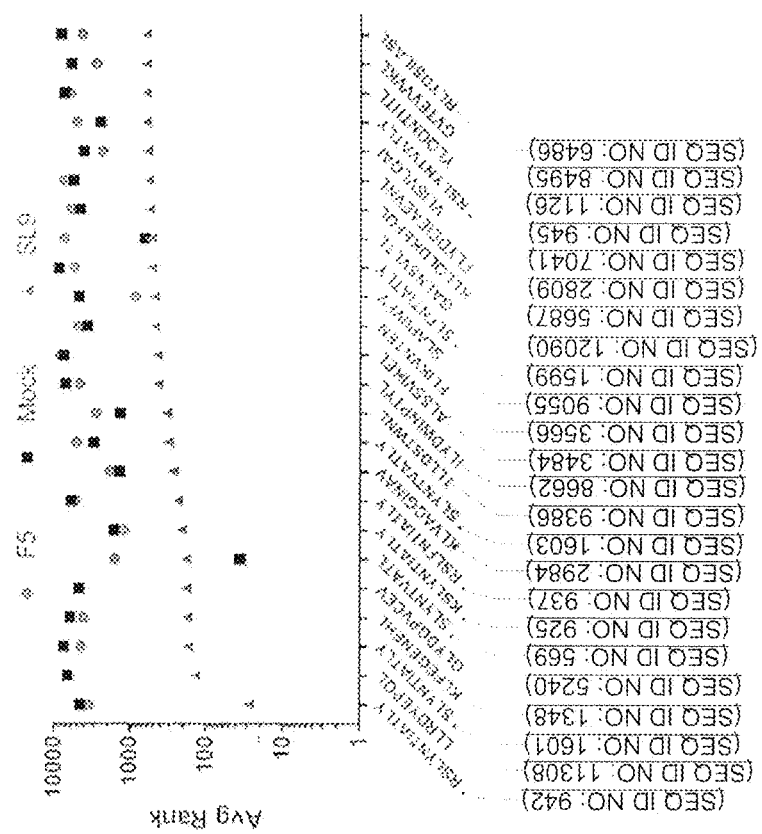
FIG. 11D illustrates a plot of average ranks for hits from an SL9 sort.
Figure 11C:
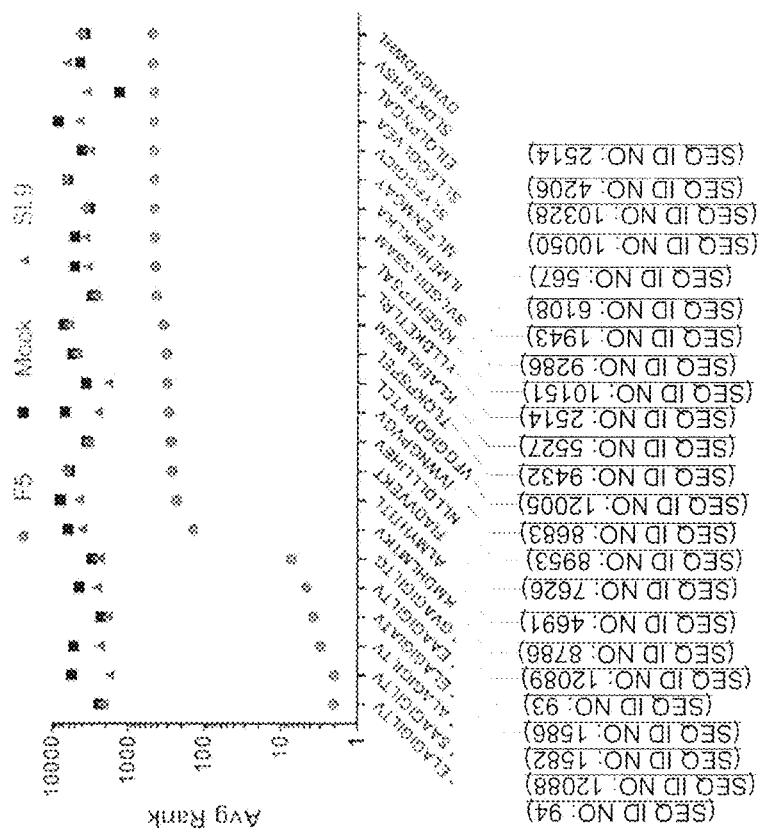
FIG. 11C illustrates a plot of average ranks for hits from an F5 sort.
Figure 11F:
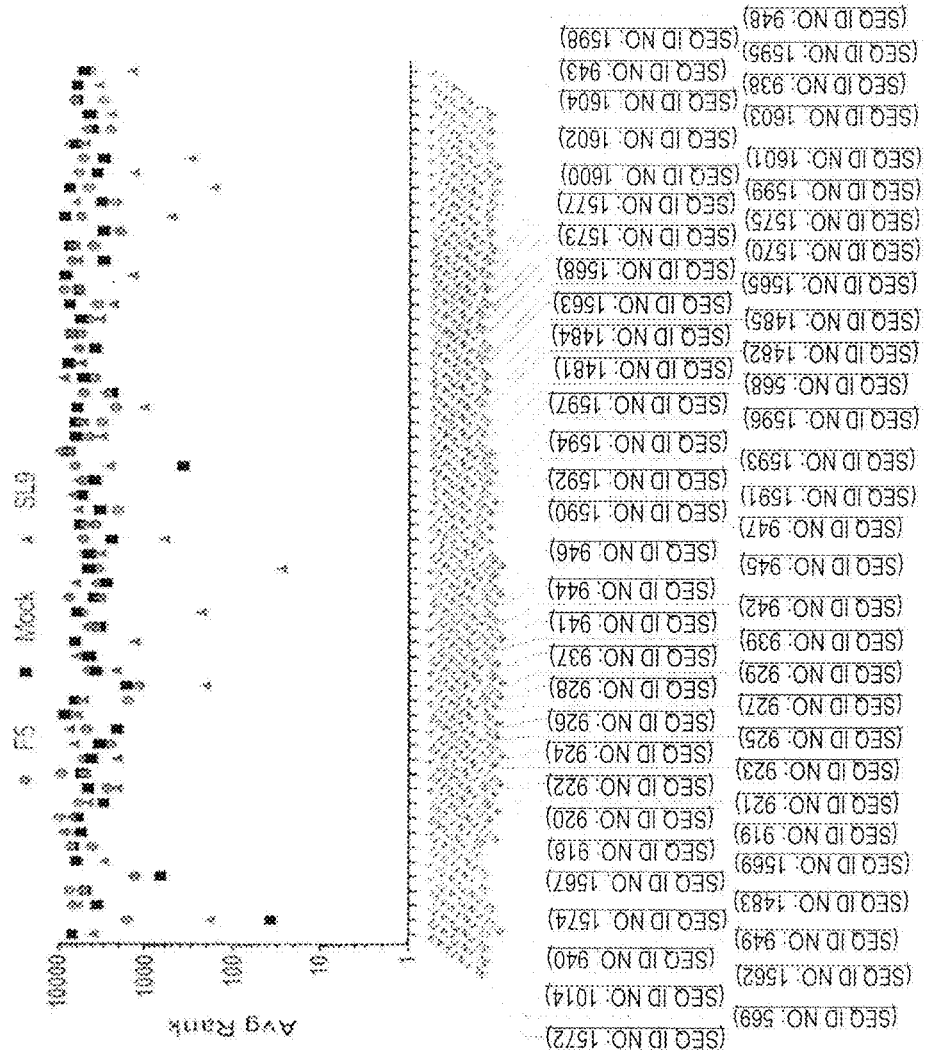
FIG. 11F illustrates a plot of average ranks for SLYNT-VATL (SEQ ID NO: 12194) analogs in an A2-SABR library.
Figure 11E:
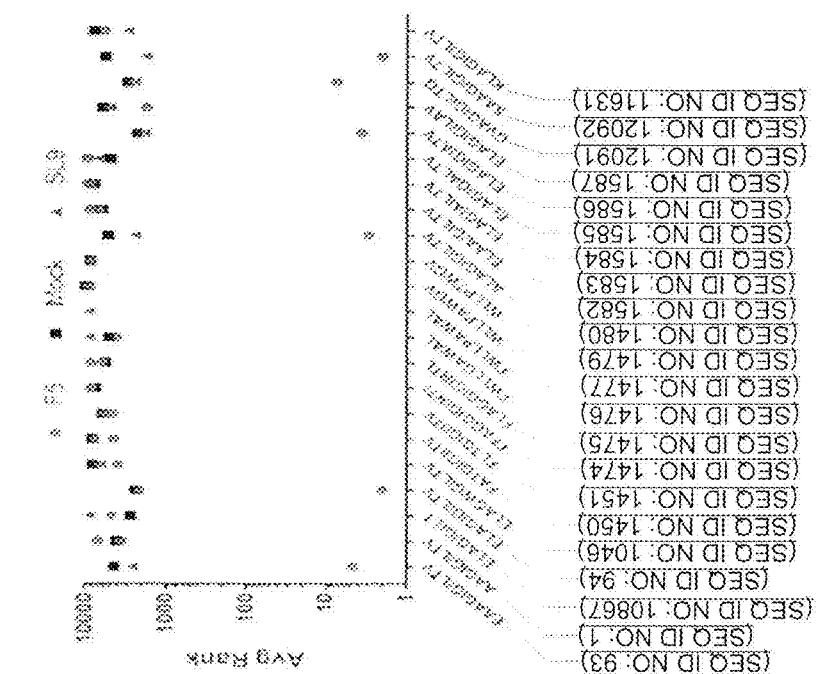
FIG. 11E illustrates a plot of average ranks for EAA-GIGILTV (SEQ ID NO: 12174) analogs in an A2-SABR library of Example 4.

FIG. 11D illustrates a plot of the average ranks for the top 24 hits from the SL9 sort. The epitopes with asterisks indicate SLYNTVATL analogs. Six out of the top ten epitopes from the SL9 sort were analogs of SLYNTAVATL, as shown in FIG. 11D. FIG. 11E illustrates a plot of the average ranks for all the EAAGIGILTV analogs in the A2-SABR library. FIG. 11F illustrates a plot of the average ranks for all the SLYNTVATL analogs in the A2-SABR library. Epitopes enriched for their corresponding TCRs were not enriched in mismatched TCRs, as shown in FIGS. 11E and 11F.

The noise observed in the SL9 sort was presumably due to the higher number of analogs of the SLYNTVATL peptide. The A2-SABR library contains 22 analogs EAA-GIGILTV and 60 analogs of SLYNTVATL. A higher number of recognized analogs would lower the average rank for each of the epitopes because of competition among the epitopes.

The ranks of all the analogs of EAAGIGILTV and SLYNTVATL in the sorts were compared. Six out of twenty-two EAAGIGILTV analogs were identified in the F5 sort, as shown in FIG. 11E, whereas nine out of sixty SLYNTVATL analogs were identified in the SL9 sort, as shown in FIG. 11F. The lack of identification of all the analogs is presumably due to reduced cross-reactivity of the F5 or SL9 TCRs towards them. Indeed, analogs SLYNTIATL (V6I) and SLFNTVATL (Y3F) are documented escape mutations in the SLYNTVATL epitope. Nevertheless, these experiments showed that a SABR library approach could identify the cognate antigen of a TCR by screening thousands of epitopes.

Example 5

Personalized Neoantigen Discovery Using SABRs

SABRs can be implemented to identify candidate T cell receptors (TCRs) for immunotherapy of a tumor. Genomic DNA or RNA from a tumor biopsy would first be sequenced and compared to non-tumor tissue from that patient. Mutations specific to the tumor, termed "neo-antigens", would be an ideal target for immunotherapy, with the hope of not inducing an immune response anywhere else in the patient's body. A list of these mutations would be generated, filtering out mutations that do not change the amino acid sequence of the patient's proteins. This list would be used to generate a list of short peptides (8-12 amino acids for class I MHC and 12-17 amino acids for class II MHC) that would contain these mutations. The peptide list would then be converted to short oligonucleotide sequences that contain the genetic encoding of those peptides flanked by the nucleotide sequences required for cloning into the SABR vector. These oligonucleotides would be synthesized and then cloned into the vector, using whatever molecular techniques are appropriate. Then that vector will be put in cells, using appropriate techniques. In our case, we used the In-Fusion kit that simplifies Gibson assembly to clone the vector. We generated lentivirus from the resultant plasmid, and infected NFAT-GFP-Jurkat cells. This batch of cells, each expressing a unique SABR, is what we call the SABR library. Overall, each cell contains an MHC molecule linked to a unique short peptide with a tumor mutation, and those MHC molecules are directly linked to a signaling domain, creating a SABR. Enough cells were infected with lentivirus so that the batch of cells cover all mutations in the list of short peptides.

To use the library to find a patient-specific therapy, the same tumor biopsy would be sequenced for RNA of TCR alpha and beta fragments. These fragments are from T cells that were invading the tumor in an attempt to suppress the tumor, known as tumor-infiltrating lymphocytes (TILs). Individual TCRs from these cells would be reconstructed from the sequencing, a fragment of DNA containing that TCR sequence would be synthesized and cloned into a vector, using whatever techniques are appropriate. Lentivirus of that plasmid would be generated and Jurkat cells (without the NFAT-GFP reporter) would be infected with that virus. The candidate TCR cells would then be co-incubated with the SABR library, for about 8 hours, then sorted on FACS sort for cells that show positive signal. In our case, the reporters were GFP and expression of CD69 cell marker. Genomic DNA from the sorted cells would be extracted, sequenced, and analyzed to determine which specific antigen is recognized by the candidate TCR. In our case, the genomic DNA was extracted with the NucleoSpin column extraction kit, PCR amplified with primers flanking the genetically encoded antigen sequence, re-amplified with primers specific for illumina sequencing, and sequenced. The resultant sequencing data was compared to a database of the short peptide sequences, and if the TCR recognizes those peptides, we expect to see an enriched genetic sequence in the pool of extracted genomic DNA.

If the TCR recognizes a mutation sequence, but not the unmutated sequence, it would be a good candidate for immunotherapy. That would involve extracting immune cells from the patient, using whatever technique desired to make those cells express the desired TCR, and infusing those adoptive cells back into the patient so that they can start attacking the tumor.

Figure 12A:
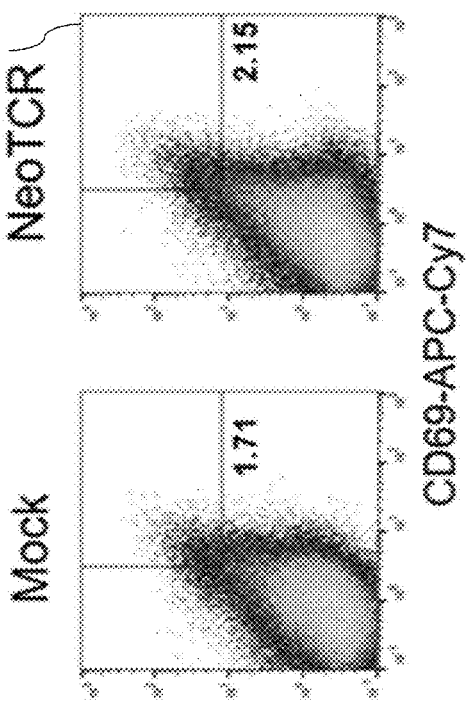
FIG. 12A illustrates a representative flow cytometry plots.

To further demonstrate the versatility of SABR libraries, a personalized approach for neoantigen discovery was tested. A recent study identified a neoantigen-specific, tumor-reactive TCR from a melanoma patient using DNA-barcoded tetramers. The identified TCR (neoTCR) was shown to recognize a neoantigen epitope created by a non-synonymous mutation in the USP7 protein. The SABR library approach was used to identify the neoantigen epitope recognized by the neoTCR by screening all possible neoepitopes identified in the tumor sample. To that end, a SABR library presenting 3291 predicted HLA-A*0201-restricted epitopes (NeoAg-SABR library) corresponding to 108 non-synonymous mutations found in the tumor was generated. The neoTCR was used as a surrogate for a tumor-reactive orphan TCR and the NeoAg-SABR library was used to identify its antigen. Jurkat cells transduced with neoTCR were co-cultured with NFAT-GFP-Jurkat cells expressing the NeoAg-SABR library, GFP+CD69+ cells were sorted, and epitopes from the sorted cells were sequenced and ranked. FIG. 12A illustrates a representative flow cytometry plots from one replicate. NeoAg-SABR library cells based on reporter gene expression were sorted. Co-culture assays using 6 million library cells with 6 million TCR-transduced Jurkat cells were set up. At 10 hours post co-culture, cells were stained for CD69 and sorted using FACS. The rectangle 1202 in the top right corner of each flow plot shows the gate used for the sort. The frequency of cells in the sort gate is indicated as percentage.

Figure 12B:
FIG. 12B illustrates a plot of average ranks from neoTCR and mock sorts.

For each epitope, the average ranks from the neoTCR sort against a mock-sort were plotted. FIG. 12B illustrates a plot of the average ranks from the neoTCR and the mock sorts. Within FIG. 12B, each dot represents the average rank for a unique epitope as calculated using the procedure described in FIGS. 10A-10C. The Y-axis shows average rank in the neoTCR sort, and the X-axis shows the average rank in the mock sort. Dots 1204 indicate USP7-derived epitopes. Seven epitopes formed a distinct cluster separated by their rank in the neoTCR sort.

Figure 12D:
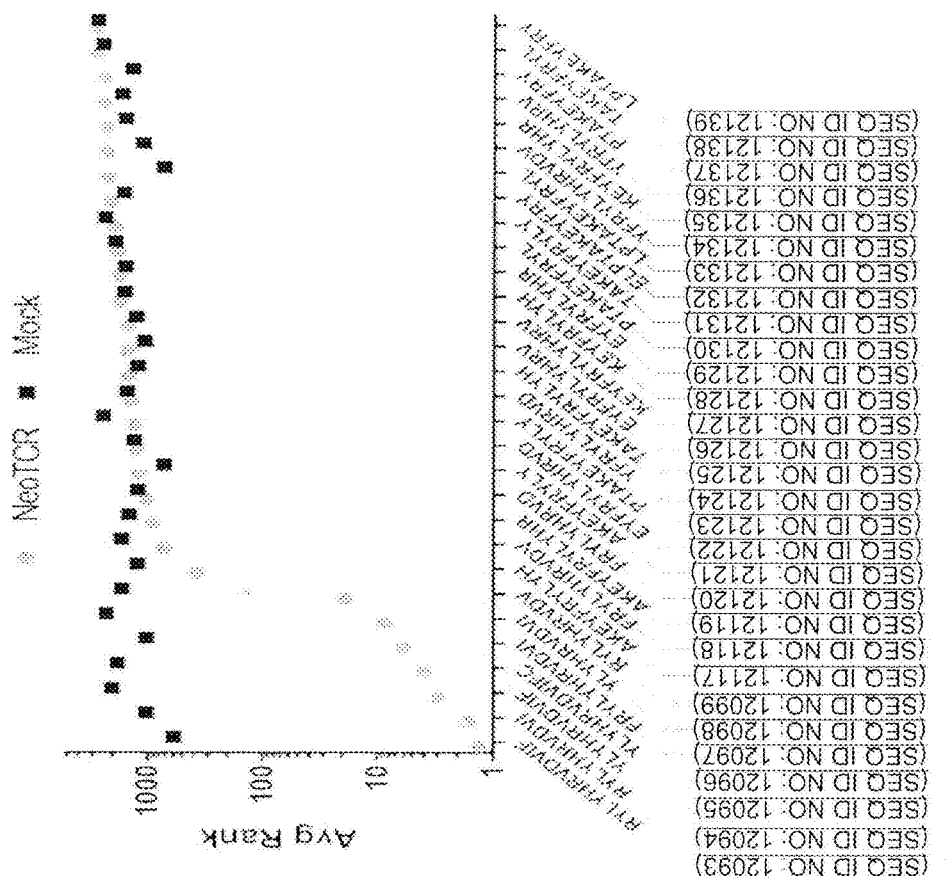
FIG. 12D illustrates a plot of average ranks for USP7-derived epitopes in a NeoAg-SABR library.
Figure 12C:
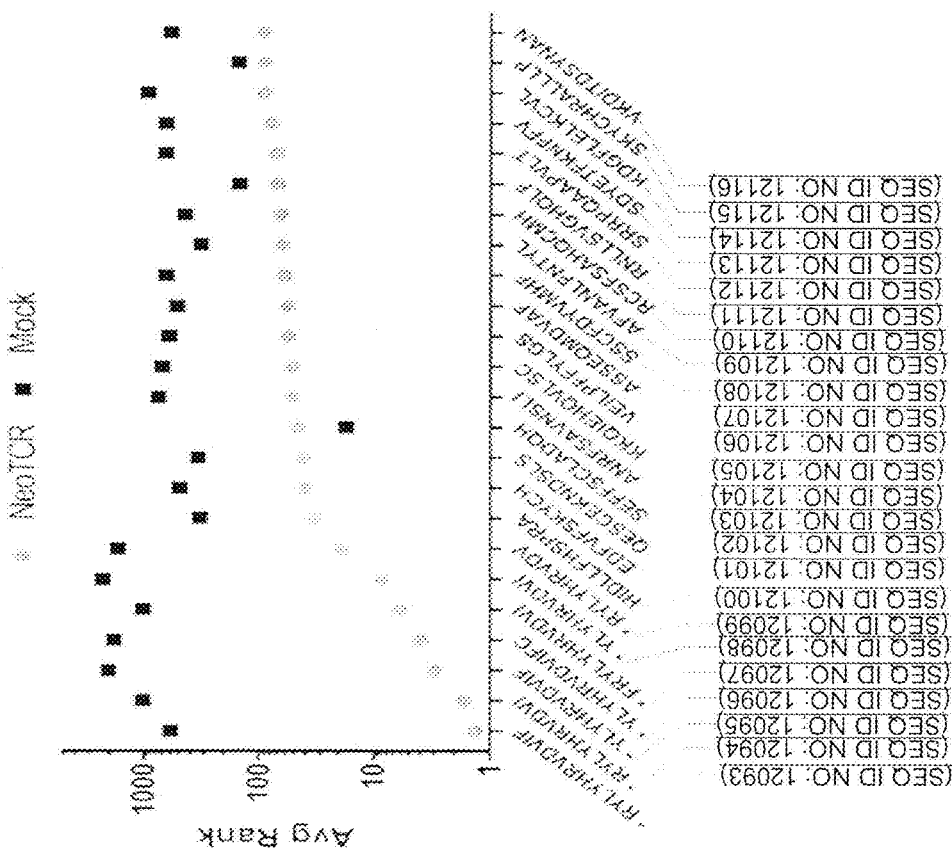
FIG. 12C illustrates a plot of average ranks for hits from a neoTCR sort.

FIG. 12C illustrates a plot of the average ranks for the top 24 hits from the neoTCR sort. Epitopes with asterisks indicate USP7-derived epitopes. The top seven hits in the neoTCR sort were epitopes derived from USP7, demonstrating successful identification of the neoantigen using our approach.

Figure 12E:
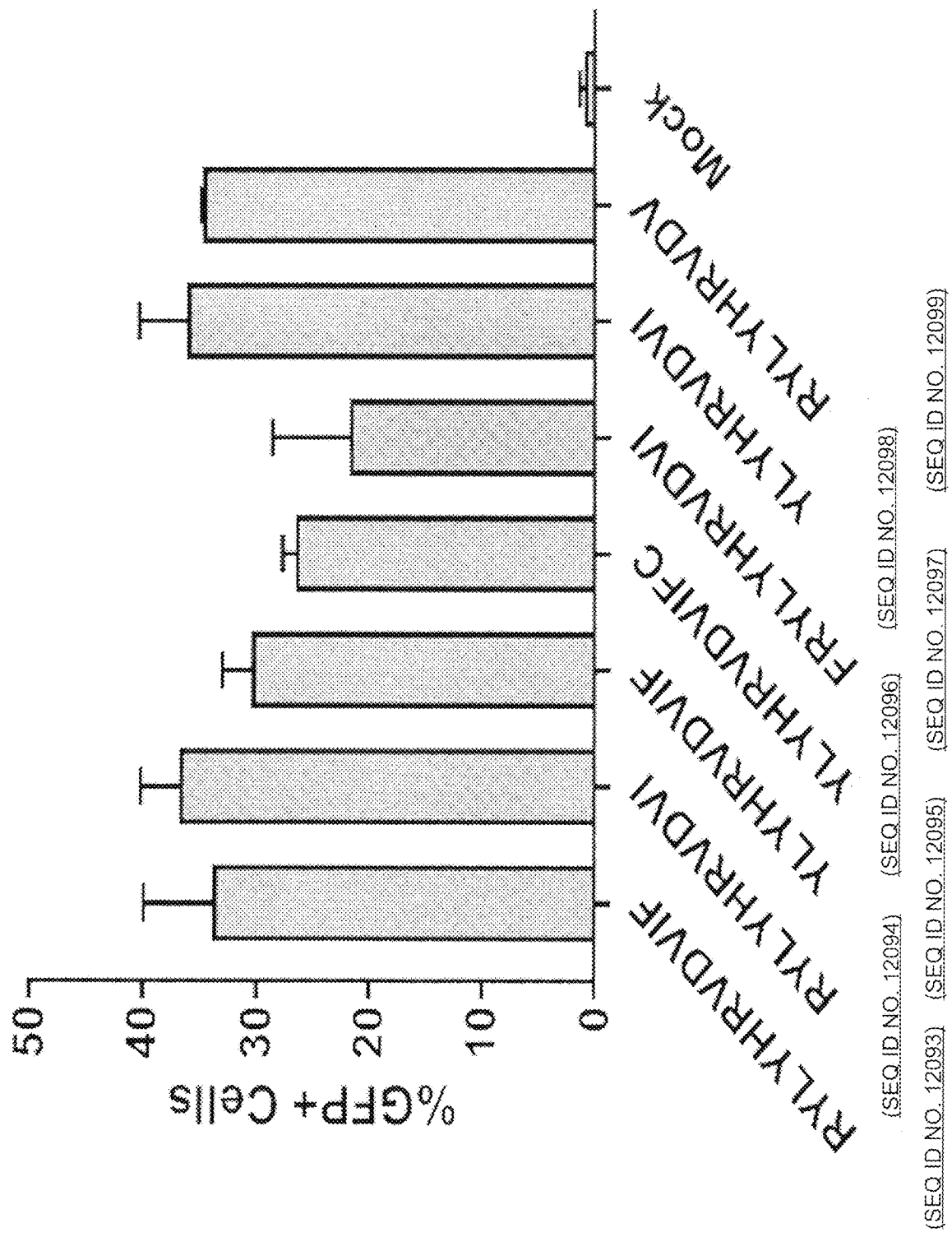
FIG. 12E illustrates a plot showing validation of top hits identified in a NeoAg-SABR screen.

FIG. 12D illustrates a plot of the average ranks for all the USP7-derived epitopes in the NeoAg-SABR library. The non-synonymous D798Y mutation in USP7 was predicted to generate thirty overlapping neoepitopes, out of which seven were identified as cognate epitopes of neoTCR. The reason the remaining 23 epitopes were not recognized in the screen is probably due to the restricted register of the epitope recognized by the neoTCR. To validate the seven detected epitopes, individual SABRs to present them were constructed. NFAT-GFP-Jurkat cells transduced with these SABRs induced GFP expression upon co-culture with Jurkat cells expressing neoTCR, as shown in FIG. 12E. FIG. 12E illustrates a plot showing validation of top hits identified in the NeoAg-SABR screen. The Y-axis shows GFP expression at 8 hours in NFAT-GFP-Jurkat cells co-cultured with Jurkat cells transduced with neoTCR. Co-culture assays were set up using 10,000 Jurkat cells transduced with neoTCR and 10,000 NFAT-GFP-Jurkat cells expressing SABRs presenting epitopes indicated on the X-axis. The mock comprised untransduced NFAT-GFP-Jurkat cells. Within FIG. 12E, the bars represent mean±sd, n=4.

These results demonstrate validation as well as successful personalization of the antigen discovery approach presented herein. Collectively, the results demonstrate that the SABRs are powerful tools for T cell antigen discovery.

Example 6

Materials and Methods

The specific reagents used in Examples 1-5 are detailed in Table 6.1. The oligonucleotide primers used for cloning and sequencing are listed in Table 6.2. The lists of epitopes in the A2-SABR libraries are listed in Tables 6.3

TABLE 6.1

| Product Name | Manufacturer/Source | Cat. No |
| --- | --- | --- |
| Jurkat Cells, Clone E6-1 | ATCC, Manassas, VA | TIB-152 |
| NFAT-GFP-Jurkat Cells | Provided by Arthur Weiss and Yvonne Chen | N/A |
| Primary T Cells | UCLA, CFAR Virology Core | N/A |
| HEK-293T Cells | ATCC, Manassas, VA | CRL-3216 |
| RPMI 1640, 1X with L-glutamine | Corning ™, Corning, NY | 10-040-CV |
| 10% Fetal Bovine Serum | Corning ™, Corning, NY | 35-015-CV |
| Penicillin-Streptomycin Solution, 100X | Corning ™, Corning, NY | 30-002-CI |
| G-418 Sulfate | Corning ™, Corning, NY | 30-234-CI |
| Immunocult ™ CD3/28 T Cell Activator | StemCell Technologies ™, Vancouver, Canada | 10991 |
| Human IL-2 IS, premium grade | MACS Miltenyi Biotec, Bergisch Gladbach, Germany | 130-097-746 |
| EAAGIGILTV | Synthesized by Pierce Thermo Fisher | N/A |
| KRWIILGLNK | Synthesized by Pierce Thermo Fisher | N/A |
| DMEM, 1X with L-Glutamine, 4.5 g/L Glucose and Sodium Pyruvate | Corning ™, Corning, NY | 10-013-CV |
| Clontech In-Fusion ® HD Cloning Kit | Clontech, Takara Bio USA, Mountain View, CA | 639650 |
| BsmBI | New England BioLabs ®, Inc, Ipswich, MA | R0580S |
| Clontech Stellar ™ Competent Cells | Clontech, Takara Bio USA, Mountain View, CA | 636763 |
| Zyppy ™ Plasmid Miniprep Kit | Zymo Research, Irvine, CA | D4036 |
| Carbenicillin (disodium) | Gold Biotechnology ®, Saint Louis, MO | C-103-SL10 |
| NucleoBond ® Xtra Maxi EF Kit | Clontech, Takara Bio USA, Mountain View, CA | 740424.50 |
| TransIT ®-293 Transfection Reagent | Mirus ® Bio, LLC Madison, WI | MIR 2704 |
| Gibco ™ Opti-MEM ™ I Reduced Serum Medium | Life Technologies, Thermo Fisher Scientific, Waltham, MA | 31985-062 |
| Millex ®-HV Syringe Filter Unit, 0.45 µm, PVDF, 33 mm, gamma sterilized | EMD Millipore, Burlington, MA | SLHV033RS |
| MACSQuant ® Analyzer 10 | MACS Miltenyi Biotec, Bergisch Gladbach, Germany | 130-096-343 |
| APC/Cy7 anti-human CD69 Clone: FN50 | BioLegend ®, San Diego, CA | 310913 |
| BD FACSort ™ | Becton Dickinson, Franklin Lakes, NJ | |
| CFSE Cell Division Tracker Kit | BioLegend ®, San Diego, CA | 423801 |
| Invitrogen ™ PureLink ™ Genomic DNA Mini Kit | Invitrogen ™ Life Technologies, Thermo Fisher Scientific, Waltham, MA | K182001 |
| KOD DNA Polymerase | EMD Millipore, Burlington, MA | 71085 |
| Macherey-Nagel NucleoSpin ® Gel and PCR Purification Kit | Clontech, Takara Bio USA, Mountain View, CA | 740609.250 |
| 2100 Bioanalyzer Instrument | Agilent, Santa Clara, CA | G2939BA |
| Ilumina ® HiSeq 2500 Sequencing System | Illumina ® San Diego, CA | SY-401-2501 |
| TreeStar FlowJo ® Flow Cytometric Data Analysis Software v10 | FlowJo, LLC Ashland, Oregon | N/A |
| GraphPad Prism v7 | GraphPad, San Diego, California | N/A |

TABLE 6.2

| Primer name | Sequence (5'-3') | Purpose |
|---|---|---|
| SS-Fwd | AGCTCCTCGAGATGGCGACGGGTTCAAG (SEQ ID NO: 12138) | SABR cloning |
| CD28-Overlap-HLA-A2-Rev | CCACCGCGAGACCTCTTGCTCCGCACTTTA CAAGCTGTGAGAGACACA (SEQ ID NO: 12139) | SABR cloning |
| CD28-Overlap-HLA-B27-Rev | CCACCGCGAGACCTCTTGCTCCGAGCTGTG AGAGACACATCAGAGC (SEQ ID NO: 12140) | SABR cloning |
| CD28Intracell-Fwd | CGGAGCAAGAGGTCTCGC (SEQ ID NO: 12141) | SABR cloning |
| XhoI-CD3z-Rev | TTGACCTCGAGTCATCTTGGTGGCAGAGCC (SEQ ID NO: 12142) | SABR cloning |
| Oligo-Insert-Fwd | CAGGAGGGCTCGGCA (SEQ ID NO: 12143) | Cloning epitopes in SABRs |
| Oligo-Insert-Rev | GGACCCTCCGCATCC (SEQ ID NO: 12144) | Cloning epitopes in SABRs |
| Epitope-Oligo | CAGGAGGGCTCGGCA NNN . . . NNN GGATGCGGAGGGTCC (SEQ ID NO: 12145) | Cloning epitopes in SABRs |
| TruSeq-Univ-SCTfixed-F | AATGATACGGCGACCACCGAGATCTACAC TCTTTCCCTACACGACGCTCTTCCGATCTG GCCTGCTTTGTTTGCC (SEQ ID NO: 12146) | High throughput sequencing |
| TruSeq-Read2-SCTfixed-R | GTGACTGGAGTTCAGACGTGTGCTCTTCCG ATCTCCTCCACCACCGCTACCTC (SEQ ID NO: 12147) | High throughput sequencing |
| Truseq-Adapter-Index | CAAGCAGAAGACGGCATACGAGAT[index] GTGACTGGAGTTCAGACGTGTGCTCTTCCG ATCT (SEQ ID NO: 12148) | High throughput sequencing |

Within Table 6.2, NNN . . . NNN indicates a back-translated epitope and [index] indicates the 6-nucleotide unique index used for sequencing.

For Examples 1-5, Jurkat cells (ATCC) were cultured in R10 (RPMI1640 (Corning) supplemented with 10% fetal bovine serum (Corning) and Penicillin/Streptomycin (Corning)). NFAT-GFP-Jurkat cells were cultured in R10 supplemented with 2 mg/ml G-418 (Corning). Primary T cells were activated in R10 supplemented with Immunocult CD3/28 (StemCell Technologies) and 40 U/ml IL-2 (Miltenyi Biotec). HEK-293T cells (ATCC) were cultured in D10 (DMEM (Corning) supplemented with 10% fetal bovine serum (Corning) and Penicillin/Streptomycin (Corning)). Peptides EAAGIGILTV and KRWIILGLNK were synthesized by Pierce Thermo Fisher.

For constructing the SABRs of Examples 1-5, single molecules encoding for β2-microglobulin and HLA were synthesized as gBlocks (IDT) and amplified using primers SS-Fwd and CD28-Overlap-HLA-Rev. CD3ζ/CD28 signaling domains were cloned from the J3 CAR using primers CD28Intracell-Fwd and XhoI-CD3z-Rev. The two parts of SABRs were assembled via PCR or via InFusion HD cloning kit (Takara). A synthetic 2 kb fragment of non-specific stuffer DNA (IDT) flanked by BsmBI sites was cloned in place of the epitope. To clone a given epitope into a SABR vector, the vector was first linearized by BsmBI digestion (NEB) and gel purified using Nucleospin Gel and PCR kit (Takara). A single stranded oligonucleotide containing overlaps with the vector and the epitope was synthesized (IDT). The oligonucleotides were amplified using KOD polymerase (Milipore) and Oligo-Insert-Fwd and Oligo-Insert-Rev. Amplified oligonucleotide was cloned into the linearized SABR vector using InFusion HD cloning kit (Takara). All cloning reactions were transformed into Stellar competent cells (Takara), grown on LB+Agar plates containing 100 μg/ml Carbenicillin (Life Technologies), and individual colonies were inoculated in liquid culture. Plasmid minipreps were performed using Zyppy Miniprep kit (Zymo). Plasmids were verified by Sanger sequencing (Laragen).

For TCR cloning of Examples 1-5, sequences for the F5, SL9, and neoTCR were synthesized as gBlocks (IDT) and cloned in the pCCLc-MND-X backbone along with a truncated form of LNGFR gene as previously described. EC27 TCR was cloned as described previously.

To generate lists of epitopes to be cloned into SABR vectors in Examples 1-5, two approaches were taken. In the universal A2-SABR library, all HLA-A*0201-restricted epitopes from Immune Epitope Database (IEDB) were downloaded. In the neoantigen SABR library, HLA-A*0201-restricted neoepitopes generated from the tumor mutanome data were used. Protein sequences were back-translated to nucleotide sequences using the most abundant codon for each amino acid based on the GenScript Codon Usage Frequency Table Tool (GenScript). Oligonucleotides encoding for the epitopes and containing overlaps with the SABR vector were synthesized in pooled single stranded oligonucleotide libraries (Twist Biosciences). Oligonucleotide libraries were amplified and cloned into the SABR vector as described previously. To ensure sufficient coverage, bacterial cells transformed with the cloning reaction were inoculated directly into 500 ml liquid cultures overnight. The plasmid DNA containing the libraries was prepared using Nucleobond Xtra Maxi Plus EF.

Lentiviral vectors to express SABRs or TCRs were packaged using previously described procedures. Briefly, 5,000,000 HEK-293T cells were plated on poly-L-Lysine coated plates for 24 hours, followed by transfection of a mixture of the lentiviral shuttle plasmid, pMDG-VSVG, and pCMV-RD8.9 using TransIT-293 (Mirus Bio) and OPTI-MEM (Life Technologies). Viruses were filtered through 0.45 micron syringe filters (Milipore) and stored at −80° C. until further use. To transduce Jurkat, NFAT-GFP-Jurkat, or Primary T cells, 2-5×10$^5$ cells were plated in culture medium and mixed with an equal volume of thawed virus in 12-well plates for three days. For NFAT-GFP-Jurkat cells, G-418 was added to the transduction mixture 48 hours later.

Figure 13A:
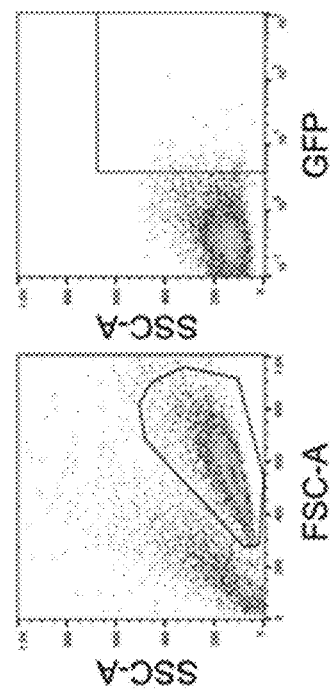
FIG. 13A illustrates a plot of a gating strategy used in co-culture assays to measure GFP expression.
Figure 13B:
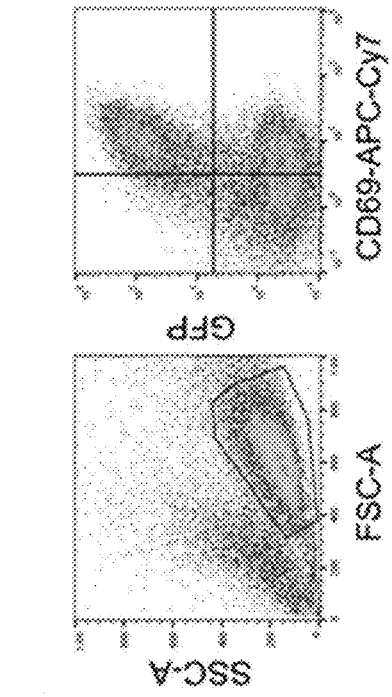
FIG. 13B illustrates a plot of a gating strategy used in co-culture assays to measure GFP and CD69 expression.
Figure 13C:
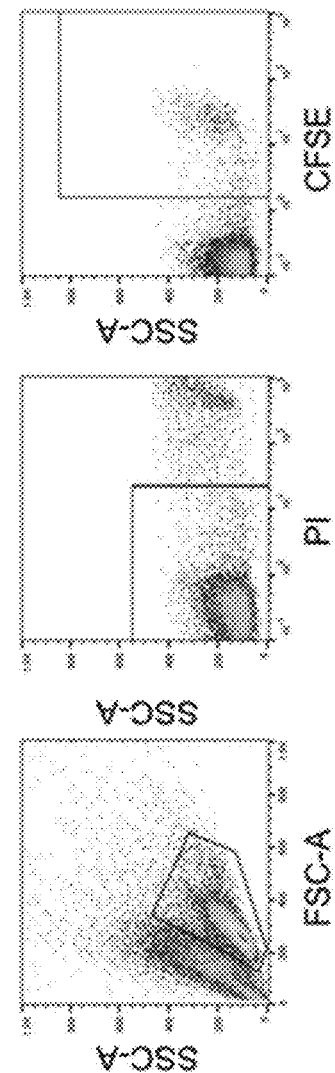
FIG. 13C illustrates a plot of a gating strategy used in cytotoxicity assays.

For the co-culture assays to test SABR signaling in Examples 1-5, 1-5×10$^4$ transduced NFAT-GFP-Jurkat cells were incubated with equal number of transduced Jurkat cells on 96 well flat or round bottom plates for 8-10 hours. The cells were then acquired on MACSQuant (Miltenyi) or stained with anti-CD69-APC-Cy7 (Biolegend Clone #) and then acquired on MACSQuant (Miltenyi). For the SABR library assays, 1.5×10$^6$ SABR library cells were incubated with 1.5×10$^6$ Jurkat cells in each well of a 6 well plate. At 8-10 hours after co-culture, cells were harvested, stained with anti-CD69-APC-Cy7 (Biolegend), and sorted on a BD FACS SORP (Becton-Dickinson). Cytotoxicity assays were performed using target cells labeled with CFSE (Biolegend) as described previously. For the empty SABR assays, transduced NFAT-GFP-Jurkat cells were incubated with 100 mg/ml of soluble peptide for 2 hours at 37° C. Equal numbers of transduced Jurkat cells were then added to the cells, followed by 8-10 hours of co-culture. Gating strategies for these assays is shown in FIGS. 13A-13C. FIG. 13A illustrates a plot of the gating strategy used in co-culture assays to measure GFP expression. FIG. 13B illustrates a plot of the Gating strategy used in co-culture assays to measure GFP and CD69 expression. FIG. 13C illustrates a plot of the gating strategy used in cytotoxicity assays.

For the high-throughput sequencing and analysis of Examples 1-5, genomic DNA was extracted from sorted cells immediately following sorting using PureLink genomic DNA extraction kit (Life Technologies). The SABR vectors were amplified using KOD polymerase (Milipore) and 10:1:10 mixture of primers TruSeq-Univ-SCTfixed-F, TruSeq-Read2-SCTfixed-R, and Truseq-Adapter-Index respectively. For each sample, 5-10 reactions using 1-30 ng of genomic DNA were performed for 30-35 cycles. The reactions were pooled and purified using Nucleospin Gel and PCR purification kit (Takara). The purified PCR product was analyzed on Bioanalyzer (Agilent) and subjected to sequencing on HiSeq 2500 (Illumina). Unaligned reads generated by the sequencer were stored in FASTQ files. The reads were first aligned to the SABR vector using Burrows-Wheeler Alignment with a mismatch penalty of $1^{22}$. For each aligned read, the epitope was translated and counted. All epitopes were ranked according to the number of reads, and an average rank was calculated for each read. The average rank was then used for further analysis.

Flow cytometry plots were analyzed on FlowJo (Treestar). Statistical analyses and graphical representations were generated by Microsoft Excel (Microsoft) and GraphPad Prism (Graphpad).

The list of epitopes in the SABR libraries can be found in Tables 6.3.

---

Lengthy table referenced here

US12221465-20250211-T00001

Please refer to the end of the specification for access instructions.

In some embodiments, any of the epitopes in Table 6.3 can be employed as the epitope in the SABR arrangement provided herein. In some embodiments, any of the epitopes in table 6.4 can be used as the epitope in the SABR arrangements provided herein.

TABLE 6.4

| Epitope | Nucleic Acid | Amino Acid | Parent Organism |
|---|---|---|---|
| CMV pp65 (495 - 503) | AATCTGGTTCCGATGGTTGCCACAGTA (SEQ ID NO: 12149) | NLVPMVATV (SEQ ID NO: 12150) | Cytomegalovirus (CMV) |
| EBV BMLF-1 (280 - 288) | GGCCTGTGTACGTTGGTGGCTATGCTG (SEQ ID NO: 12151) | GLCTLVAML (SEQ ID NO: 12152) | Epstein-Barr Virus (EBV) |
| GAD65 (114- 123) | GTTATGAACATTTTGCTGCAGTACGTGGTG (SEQ ID NO: 12153) | VMNILLQYVV (SEQ ID NO: 12154) | Homo sapiens |
| GAD65 (339 - 352) | ACAGTCTACGGGGCATTCGACCCTCTGCTGG CCGTAGCAGAT (SEQ ID NO: 12155) | TVYGAFDPLL AVAD (SEQ ID NO: 12156) | Homo sapiens |
| glia-a (228 - 240) | TCAGGGGAGGGCAGCTTCCAGCCGTCTCAAG AAAATCCG (SEQ ID NO: 12157) | SGEGSFQPSQ ENP (SEQ ID NO: 12158) | Common wheat (Triticum aestivum) |

TABLE 6.4-continued

| Epitope | Nucleic Acid | Amino Acid | Parent Organism |
|---|---|---|---|
| glia-a1a (60-68) | CCCTTCCCCCAGCCCGAGCTGCCCTAC (SEQ ID NO: 12159) | PFPQPELPY (SEQ ID NO: 12160) | Common wheat (*Triticum aestivum*) |
| IA-2 (797-805) | ATGGTATGGGAGAGCGGATGTACTGTG (SEQ ID NO: 12161) | MVWESGCTV (SEQ ID NO: 12162) | *Homo sapiens* |
| IGRP (265-273) | GTCCTCTTTGGTCTTGGGTTCGCAATC (SEQ ID NO: 12163) | VLFGLGFAI (SEQ ID NO: 12164) | *Homo sapiens* |
| Insulin B (10-18) | CACCTCGTCGAGGCATTGTACCTCGTG (SEQ ID NO: 12165) | HLVEALYLV (SEQ ID NO: 12166) | *Homo sapiens* |
| Insulin B (9-23) | AGCCACCTGGTGGAGGCCCTGTACCTGGTGT GCGGCGAGAGGGGC (SEQ ID NO: 12167) | SHLVEALYLV CGERG (SEQ ID NO: 12168) | *Homo sapiens* |
| KK10 | AAAAGATGGATAATCCTGGGATTAAATAAA (SEQ ID NO: 12169) | KRWIILGLNK (SEQ ID NO: 12170) | human immunodeficiency virus (HIV) |
| LLO (190-205) | AACGAGAAGTACGCCCAGGCCTACCCCAACG TGAGCGCCAAGATCGAC (SEQ ID NO: 12171) | NEKYAQAYP NVSAKID (SEQ ID NO: 12172) | Listeria monocytogenes |
| MART1 | GAGGCCGCCGGCATCGGCATCCTGACCGTG (SEQ ID NO: 12173) | EAAGIGILTV (SEQ ID NO: 12174) | *Homo sapiens* |
| MART1-A27L | GAGCTGGCCGGCATCGGCATCCTGACCGTG (SEQ ID NO: 12175) | ELAGIGILTV (SEQ ID NO: 12176) | Synthetic |
| NYESO | AGCCTGCTGATGTGGATCACCCAGTGC (SEQ ID NO: 12177) | SLLMWITQC (SEQ ID NO: 12178) | *Homo sapiens* |
| NYESO-1V | TCCCTGCTGATGTGGATCACCCAGGTG (SEQ ID NO: 12179) | SLLMWITQV (SEQ ID NO: 12180) | Synthetic |
| OVA (257-264) | AGCATCATCAACTTCGAGAAGCTG (SEQ ID NO: 12181) | SIINFEKL (SEQ ID NO: 12182) | chicken (*Gallus gallus domesticus*) |
| OVA (323-339) | ATAAGCCAGGCCGTTCATGCTGCACATGCAG AAATAAACGAGGCTGGCAGA (SEQ ID NO: 12183) | ISQAVHAAHA EINEAGR (SEQ ID NO: 12184) | chicken (*Gallus gallus domesticus*) |
| PPI (15-24) | GCACTCTGGGGTCCTGATCCGGCTGCGGCT (SEQ ID NO: 12185) | ALWGPDPAA A (SEQ ID NO: 12186) | *Homo sapiens* |
| ProIns C19-35 | GGCGCCGGCAGCCTGCAGCCCCTGGCCCTG AGGGCAGCCTGCAGAAGAGG (SEQ ID NO: 12187) | GAGSLQPLAL EGSLQKR (SEQ ID NO: 12188) | *Homo sapiens* |
| ProIns C19-A3 | GGAAGTTTGCAGCCATTGGCTCTGGAAGGGA GCCTGCAAAACGCGGCATTGTA (SEQ ID NO: 12189) | GSLQPLALEG SLQKRGIV (SEQ ID NO: 12190) | *Homo sapiens* |

TABLE 6.4-continued

| Epitope | Nucleic Acid | Amino Acid | Parent Organism |
|---------|--------------|------------|-----------------|
| ProIns C19-A3 L3W | GGAAGTTTGCAGCCATTGGCTTGGGAAGGGA GCCTGCAAAAACGCGGCATTGTA (SEQ ID NO: 12191) | GSLQPLAWEG SLQKRGIV (SEQ ID NO: 12192) | Synthetic |
| SL9 | TCATTATATAATACAGTAGCAACCCTC (SEQ ID NO: 12193) | SLYNTVATL (SEQ ID NO: 12194) | human immunodeficiency virus (HIV) |

Example 7

Antigen presenting Cells to Detect Islet Autoimmunity in Type 1 Diabetes

Type 1 Diabetes (T1D) is an autoimmune disorder caused by progressive destruction of insulin-producing pancreatic β cell islets. The role of T cells in pathology of T1D is well established by immunological studies and discovery of genetic risk factors. However, there is an unmet need for tools to link the immune manifestations of these genetic risk factors.

An immune-reactive cell, such as a pancreatic β cell in T1D, presents antigenic epitopes on human leukocyte antigen molecules (pHLA complexes) on its surface. T cells use their unique TCR to specifically recognize pHLA. In T1D, both CD4+ and CD8+ T cells recognize and respond to self-antigens on pancreatic β cells. CD8+ T cells recognize Class I pHLA and induce a cytotoxic response, whereas, CD4+ T cell recognize Class II pHLA and induce a helper response that modulates immune function. A bottleneck in studying T cells is at the identification of the antigens they target. Two major tools to detect the antigen-specific T cells are pHLA-multimers and functional assays. pHLA multimers are purified HLA molecules complexed with peptides and conjugated to fluorophores and are used to identify antigen-specific T cells by flow cytometry. Despite their extensive use, they have several limitations: Class II pHLA multimers are inherently unstable, in particular, those for alleles associated with increased risk for T1D (HLA-DQ2 and -DQ8) and are therefore difficult and non-robust to use, they do not represent the physiological immune synapse, and they fail to detect low-avidity T cells inherently associated with autoimmunity. Functional assays, such as ELISAs and ELISPOTs, efficiently detect T cell function by measuring cytokine production upon stimulation with Antigen Presenting Cells (APCs) presenting desired epitopes. However, these assays do not allow distinction between different pHLAs, as APCs have three to ten different HLA alleles. They are also reliant on the induction of a strong functional response such as IFNγ secretion and thus cannot detect functionally impaired autoimmune T cells. The detection of antigen-specific regulatory T cells (Tregs) is particularly challenging as their activity inhibits typically measured responses, and therefore is masked in functional assays as negative response. Indeed, there is an unmet need for detection of antigen-specific Tregs.

Figure 14B:
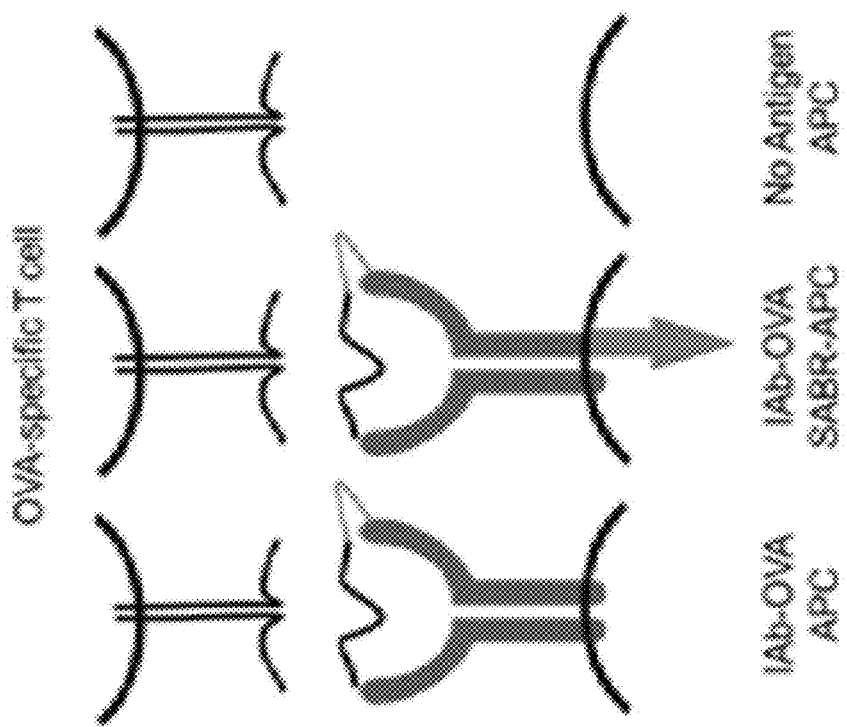
FIG. 14B illustrates a schematic of a SABR showing induction of a signal by a SABR presenting Ovalbumin peptide on a mouse class II pMHC (IAb-OVA) upon recognition by cognate T cells.
Figure 14A:
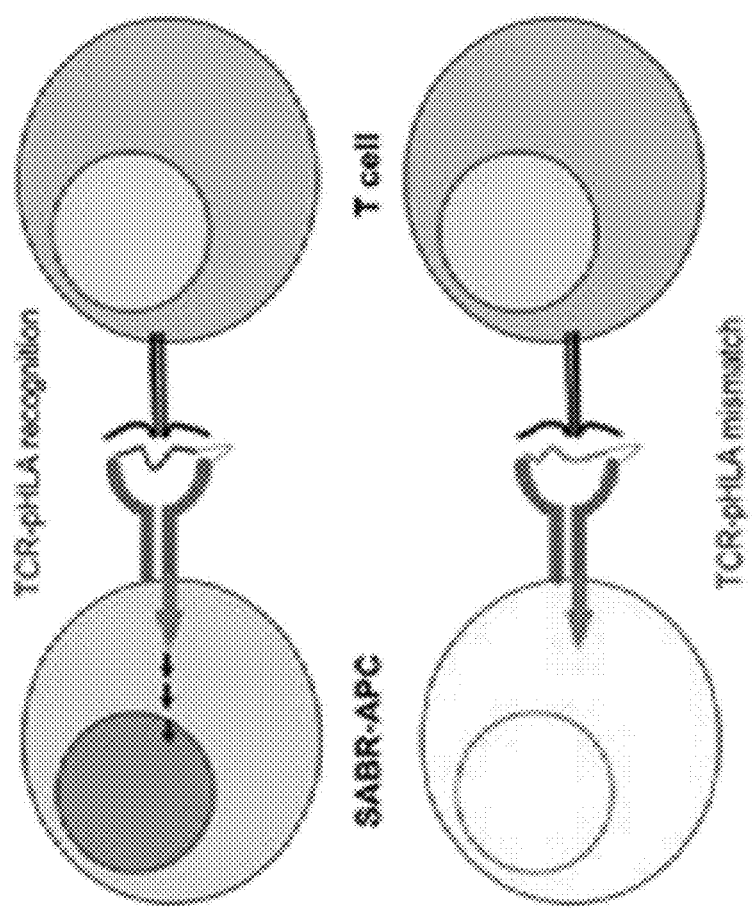
FIG. 14A illustrates a schematic showing the structure of a SABR and signal induction by SABRs upon TCR-pHLA recognition.
Figure 14C:
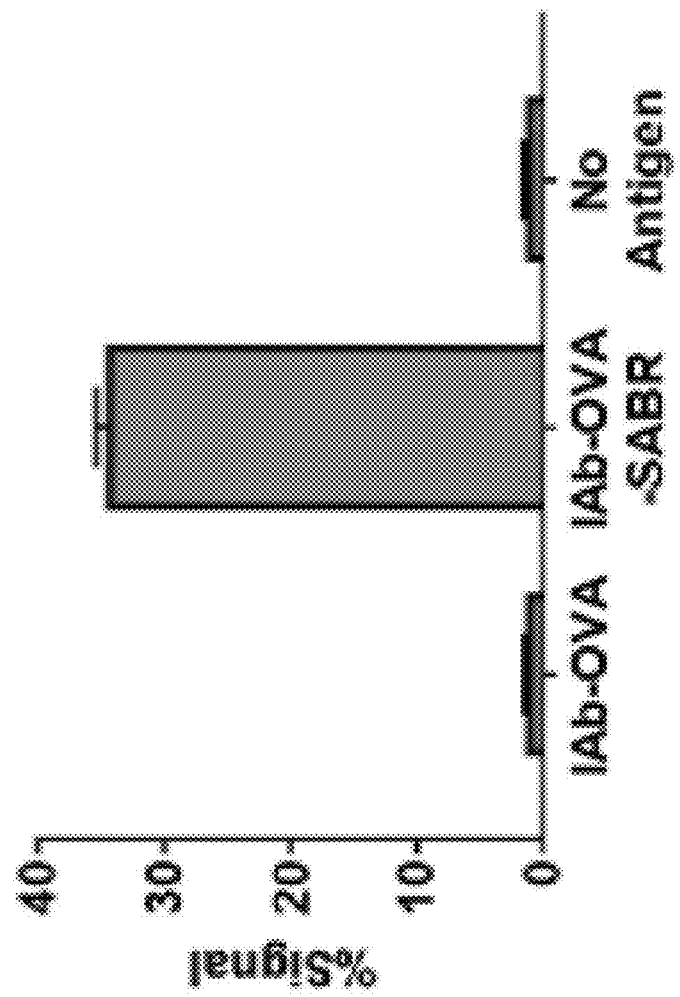
FIG. 14C illustrates a bar graph showing induction of a signal by SABRs presenting Ovalbumin peptide on a mouse class II pMHC (IAb-OVA) upon recognition by cognate T cells.

To that end, SABRs to detect pHLA-TCR interactions were constructed. FIG. 14A illustrates a schematic showing the structure of the SABR and signal induction by SABRs upon TCR-pHLA recognition. The extracellular domain of the SABR used in this example was a pHLA complex, which upon recognition by a T cell, causes the intracellular domain to induce a signal. APCs engineered to express SABRs present a given epitope and induce a measurable output when recognized by cognate T cells. The advantages of SABR-APCs over multimers or functional assays include: physiological pHLA display of single alleles on the surface of an APC, ability to define pHLA combinations genetically, multiplexed detection of epitope specificities, and detection of pHLA-TCR interaction independently from T cell function. FIG. 14B and FIG. 14C demonstrate this technique by showing induction of a signal by a SABR presenting Ovalbumin peptide on a mouse class II pMHC (IAb-OVA) upon recognition by cognate T cells. These SABR-APCs can be used to detect islet-specific immune responses in T1D patients, to study the immunological effects of genetic risk factors, and to interrogate natural and immunotherapy-induced T cells.

Figure 14E:
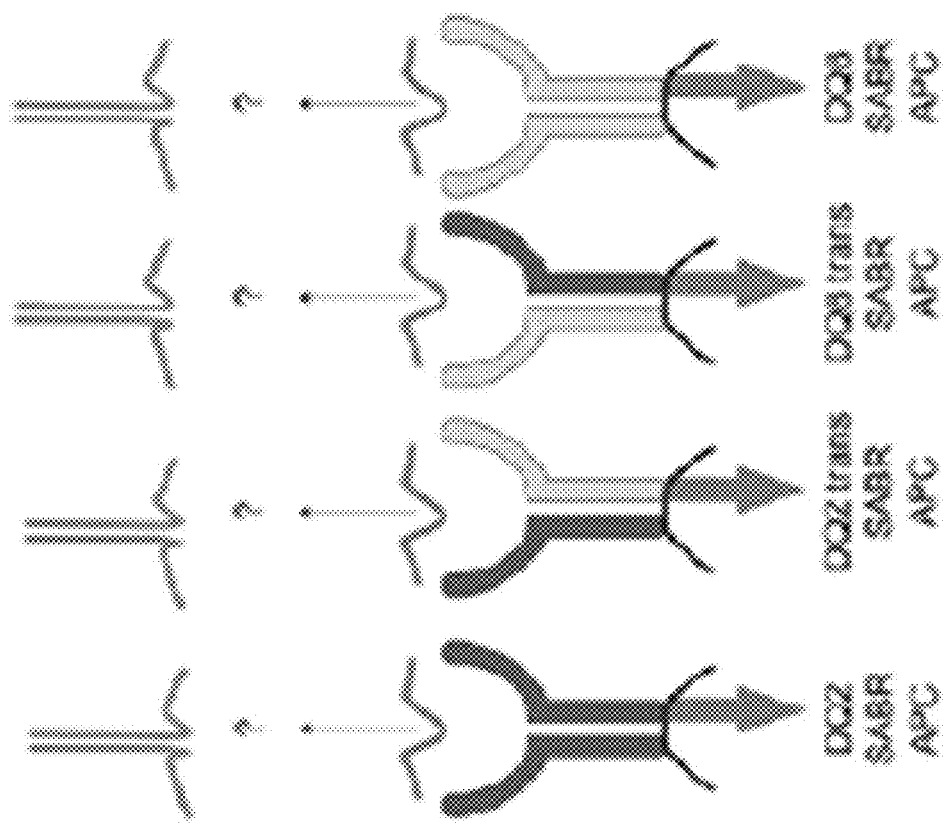
FIG. 14E illustrates SABRs encoding four DQ2/8 combinations on separate APCs allowing their distinction.
Figure 14D:
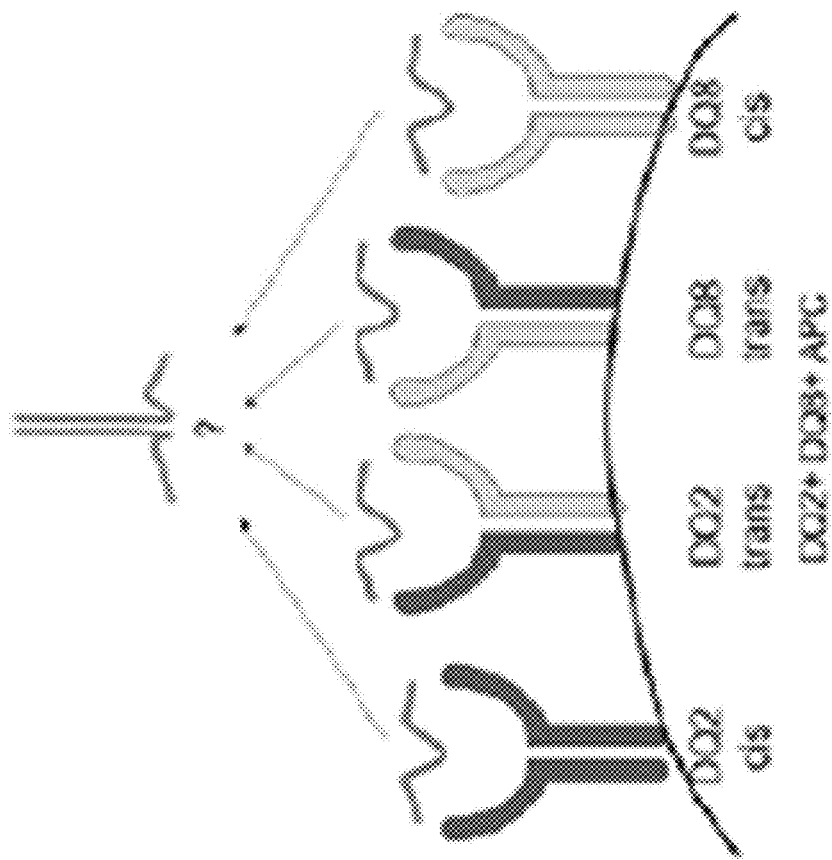
FIG. 14D illustrates four combinations of HLA-DQ alleles on APCs from DQ2-DQ8 heterozygous patients.

The SABR-APCs can be used to understand the immunological mechanism of protective and susceptible genetic risk factors. Several Class II HLA alleles are associated with either protection from or susceptibility to T1D. Both HLA-DQ2 and DQ8 are risk factors for T1D, and particularly, patients who carry both alleles are at significantly higher risk than those carrying either allele alone. This phenomenon is thought to be due to cross-pairing of DQ2 and DQ8 chains (known as DQ2trans or DQ8trans) that may present peptide epitopes and induce autoimmunity. APCs from these patients express correctly paired and cross-paired molecules simultaneously, which cannot be distinguished by current methods, as shown in FIG. 14D. FIG. 14D illustrates four combinations of HLA-DQ alleles on APCs from DQ2-DQ8 heterozygous patients. SABRs can be used to display genetically encoded peptide epitopes linked to specific pairs of such so-called HLA-DQ transdimers on separate APCs to study the differences between patients carrying different genetic risk factors using a rare B-cell line lacking the endogenous DR and DQ locus, as shown in FIG. 14E. FIG. 14E illustrates SABRs encoding four DQ2/8 combinations on separate APCs allowing their distinction. Furthermore, SABR-APCs can be used to distinguish between immunogenicity of protective and susceptible variants of Insulin Defective Ribosomal Products (INS-DRiPs). Thus, the differences between immune responses from individuals carrying different genetic risk alleles can be dissected.

The function of islet autoreactive effector and regulatory T cells using SABR-APCs can also be studied. Autoimmune T cells exhibit unusual modes of antigen recognition and subsequent functional output. For instance, regulatory T cells specific for HLA-DR4-Proinsulin (C19-A3) bind with reversed polarity compared to effector T cells specific for the same epitope. Because of the inherent limitations in pHLA multimers, studying these distinctions has been extremely challenging. Therefore, SABR-APCs presenting these epitopes as substrates can be used for measuring the functional differences between islet-specific T cell clones derived from T1D patients. These studies can be used understand the functional basis of distinct T cell subtypes from the perspective of the APC.

Natural and immunotherapy-induced islet-specific T cell responses can be detected using SABRs. In scenarios of suppressed immune function, current methods fail to detect antigen-specific T cells. This is particularly relevant in scenarios of islet transplantation or immune tolerance observed in healthy individuals or in patients successfully treated with tolerogenic immunotherapy, such as vaccination with Proinsulin C19-A3. Since the technology platform described herein only relies on TCR/epitope/HLA interaction, islet specific effector or regulatory T-cells can be detected and enumerated, even if their response is suppressed. SABR-APCs can be used to diagnose C19-A3-specific T cell responses from patients receiving immunotherapy with tolerogenic dendritic cells pulsed with this immunodominant proinsulin peptide. The use of SABRs can be extended for immunomonitoring by multiplexing detection of several epitopes from the same patient sample, allowing identification of 'immune signatures' in the islet-specific autoimmune responses that may correlate with response to this novel type of tissue specific immune intervention therapy.

Example 8

Class II MHC SABRs

Figure 15A:
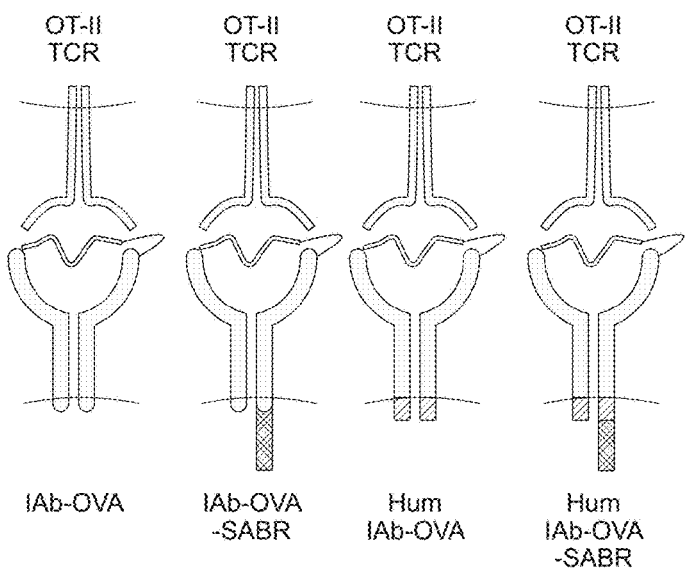
FIG. 15A illustrates a schematic of IAb-OVA and Hum IAb-OVA SABRs and signaling induction upon recognition of an OT-II TCR.
Figure 15B:
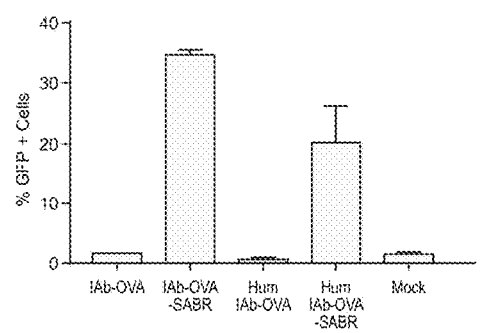
FIG. 15B illustrates a bar graph showing signaling induction upon recognition of OT-II TCR for IAb-OVA and Hum IAb-OVA SABRs.

SABRs comprising antigen presenting domains comprising class II MHC were also tested to determine signaling induction capability. The experimental methods described in Example 1 and 6 were used to test the capacity of class II MHC SABRs. FIG. 15A illustrates a schematic of IAb-OVA and Hum IAb-OVA SABRs and signaling induction upon recognition of an OT-II TCR. FIG. 15B illustrates a bar graph showing signaling induction of OT-II TCR for IAb-OVA and Hum IAb-OVA SABRs. As shown in FIG. 15B, the class II MHC SABRs were capable of inducing a signal while the other constructs did not induce signals. The results show that SABRs comprising class II MHC can induce signaling upon successful and specific TCR-pMHC interaction.

Figure 16A:
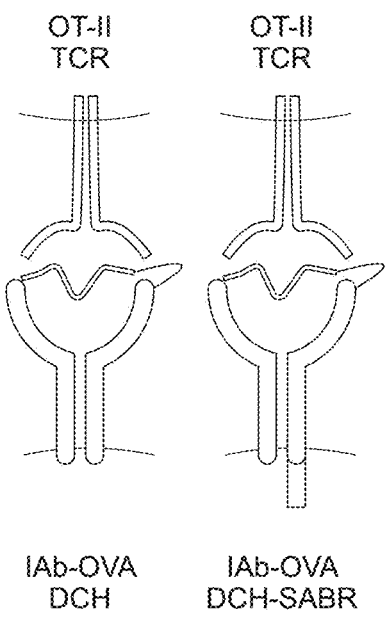
FIG. 16A illustrates a schematic of IAb-OVA DCH and an IAb-OVA DCH-SABR and signaling induction upon recognition of an OT-II TCR.
Figure 16B:
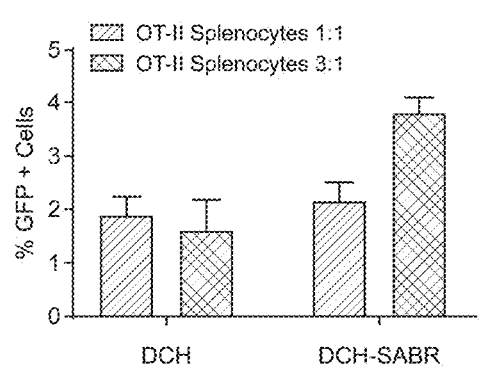
FIG. 16B illustrates a bar graph showing signaling induction upon recognition of mouse splenocytes expressing the OT-II TCR for IAb-OVA and Hum IAb-OVA SABRs.

Furthermore, FIG. 16A illustrates a schematic of IAb-OVA DCH and an IAb-OVA DCH-SABR and signaling induction upon recognition of an OT-II TCR. FIG. 16B illustrates a bar graph showing signaling induction of OT-II TCR for IAb-OVA and Hum IAb-OVA SABRs. These results also show that SABRs comprising class II MHC can induce signaling upon successful and specific TCR-pMHC interaction. Thus, the experiment using Class I MHC SABRs, which are known for being relatively easy to work with, also worked for Class II MHC SABRs, which are known for being difficult to work with traditional methods for antigen discovery described herein.

Example 9

SABRs Recognize Primary Cells

Figures 17A, 17B:
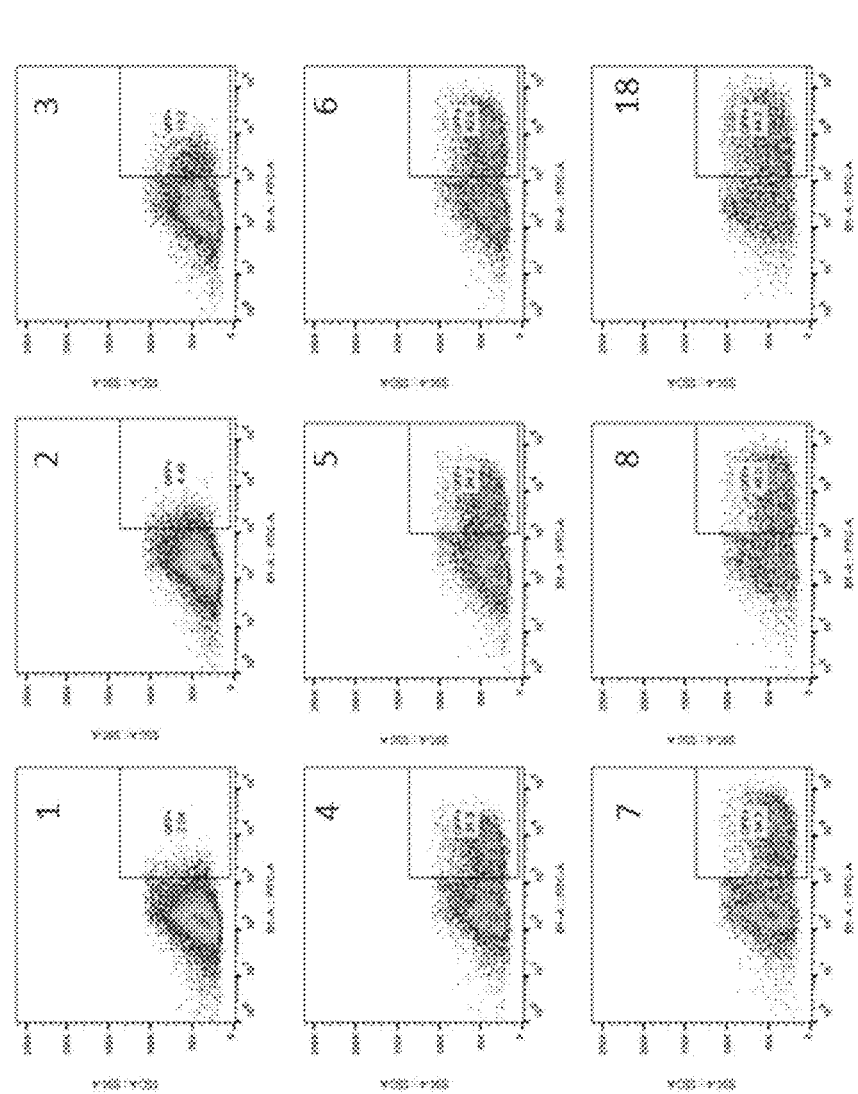
FIG. 17A illustrates a line graph depicting % GFP+ cells over time.
FIG. 17B illustrates representative flow cytometry plots from the experiment.

SCDR constructs were constructed to express, for example, either A2-NYESO (a cancer-specific MHCT antigen combination) or B27-KK10 (an HIV-specific MHC-antigen combination). In some embodiments, the SCDR constructs for A2 and B27 can be constructed and a peptide can be used to present, for example, either NYESO or KK10 antigen. NFAT-GFP-Jurkats, can be transduced with the SCTR constructs or with SCDR constructs and pulsed with peptide antigen as reporter cells. The reporter cells can be transduced with Jurkat cells expressing, for example, either A2-NYESO-specific TCR or B27-KK10-specific TCR, and the frequency of GFP+ cells can be measured with flow cytometry. FIG. 17A illustrates a line graph depicting % GFP+ cells over time. FIG. 17B illustrates representative flow cytometry plots from the experiment.

The results show that a signal was induced in about 30% of reporter cells within 4 hours of incubation and about 50% of reporter cells within 8 hours of incubation. Also, about 50% of the maximal signal was attained at 4 hours and about 100% of the maximal signal was attained by 8 hours.

Using the experimental results of Examples 3 and 6, TCR-transduced Jurkat cells were co-incubated with SCTR-transduced NFAT-GFP-Jurkat cells. FIG. 18A illustrates a bar graph depicting the frequency of % GFP+ for TCR-transduced Jurkat cells incubated with SCTR-transduced NFAT-GFP-Jurkat cells. FIG. 18B illustrates a bar graph depicting the frequency of % GFP+ for TCR-transduced PBMCs incubated with SCTR-transduced NFAT-GFP-Jurkat cells. FIG. 18C illustrates a line graph depicting the frequency over time of % GFP+ for TCR-transduced PBMCs incubated with SCTR-transduced NFAT-GFP-Jurkat cells.

As illustrated in FIGS. 18A-18C, SABRs are able to recognize antigen receptors on primary cells (e.g. directly from patient samples), the same way they recognize transgenic antigen receptors in cell lines.

Species, Variants, Deletions, or Modified Versions of Embodiments

Figure 20A:
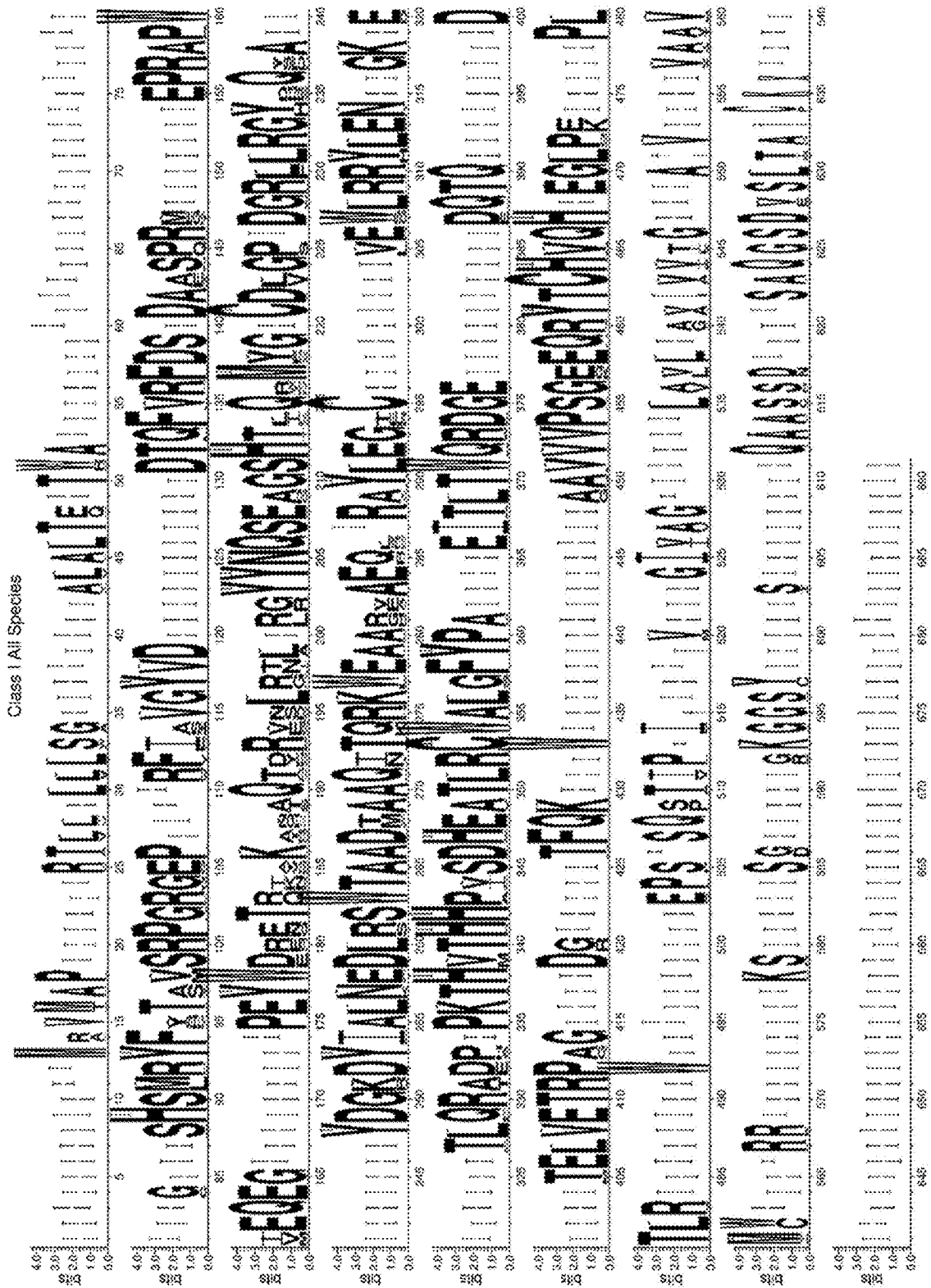
FIG. 20A displays a sequence alignment for class I MHC across a wide variety of species.
Figure 20B:
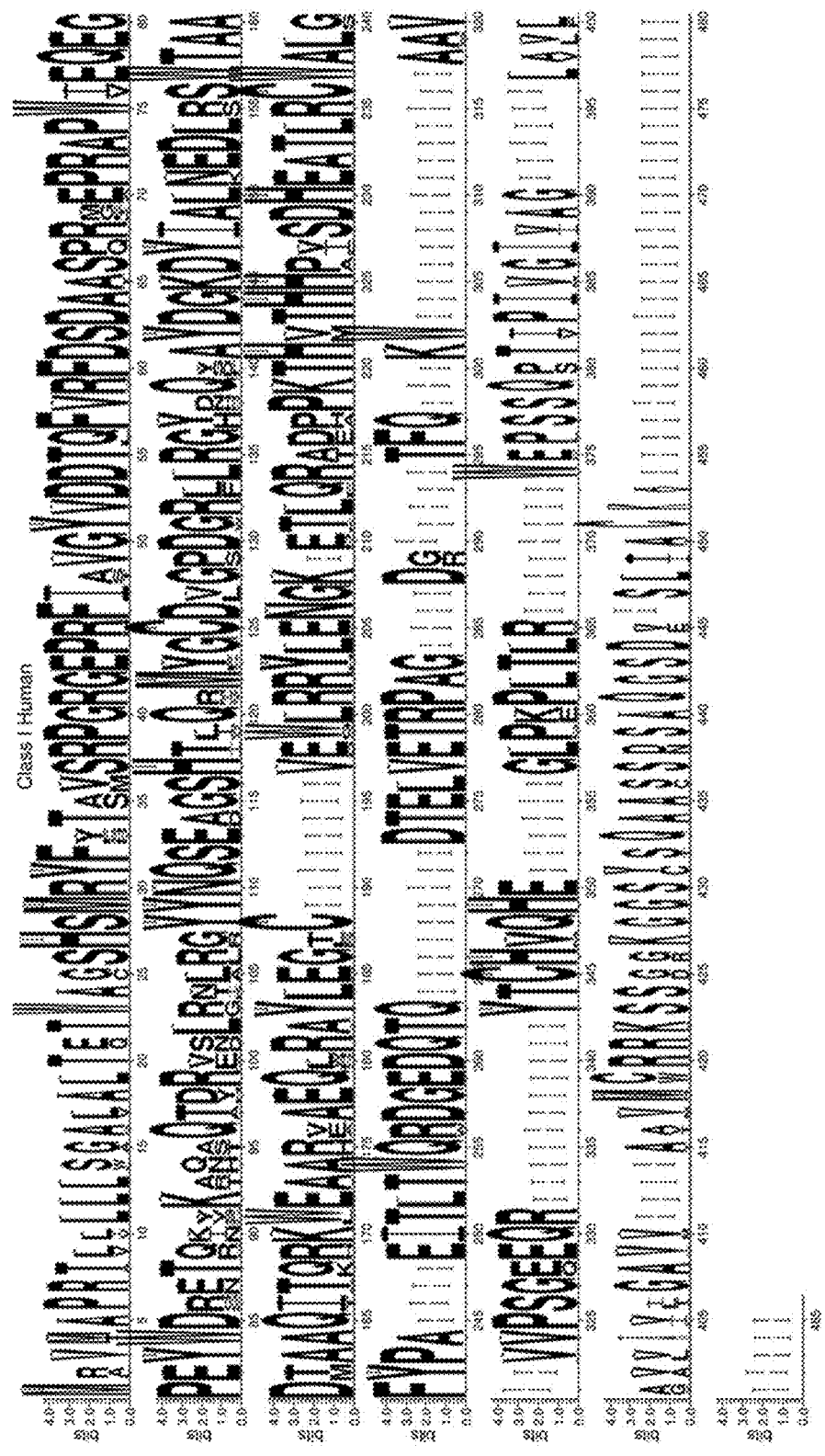
FIG. 20B displays a sequence alignment for class I MHC across humans.
Figure 20C:
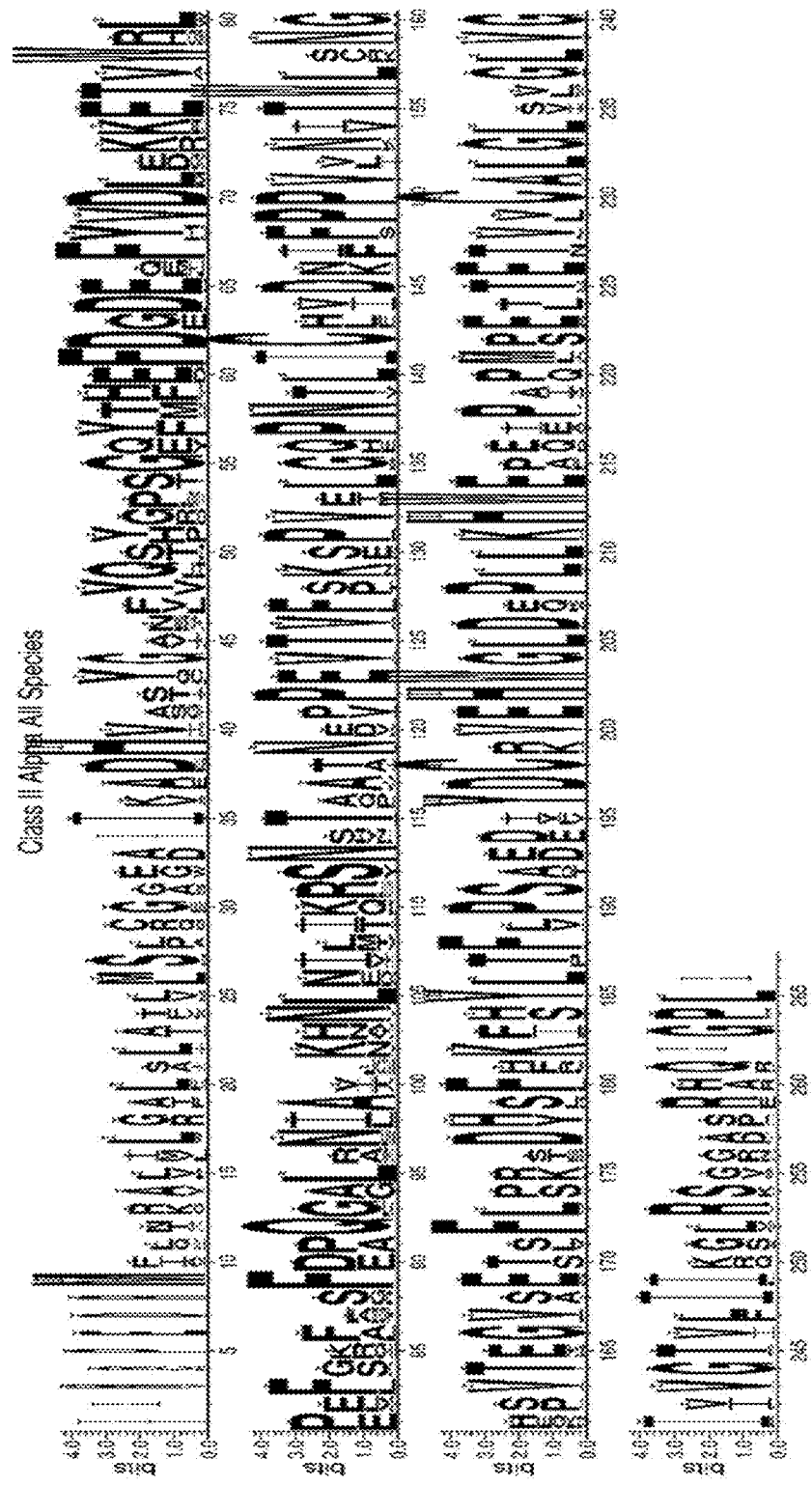
FIG. 20C displays a sequence alignment for class II alpha MHC across a wide variety of species.
Figure 20D:
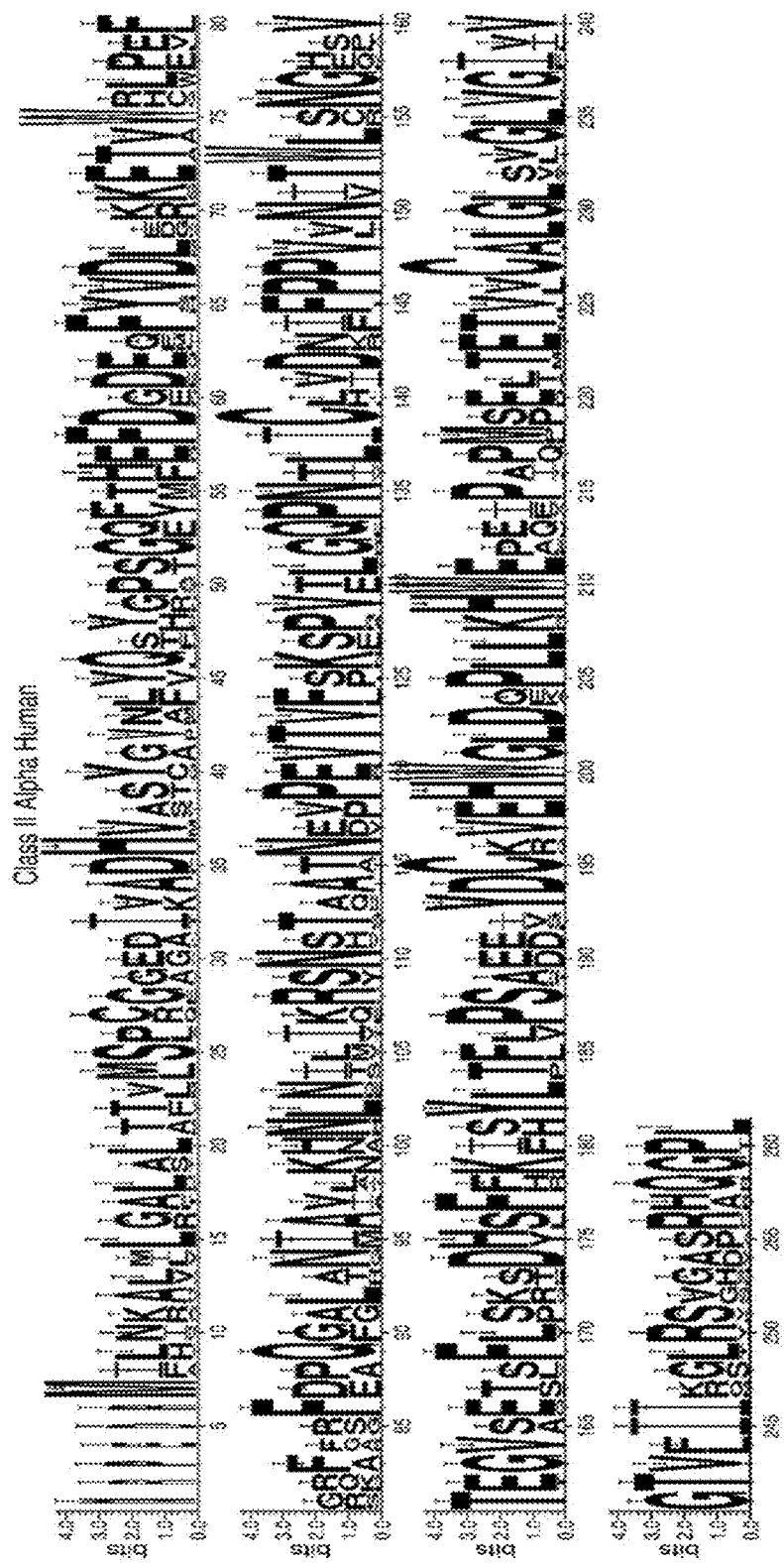
FIG. 20D displays a sequence alignment for class II alpha MHC across humans.
Figure 20E:
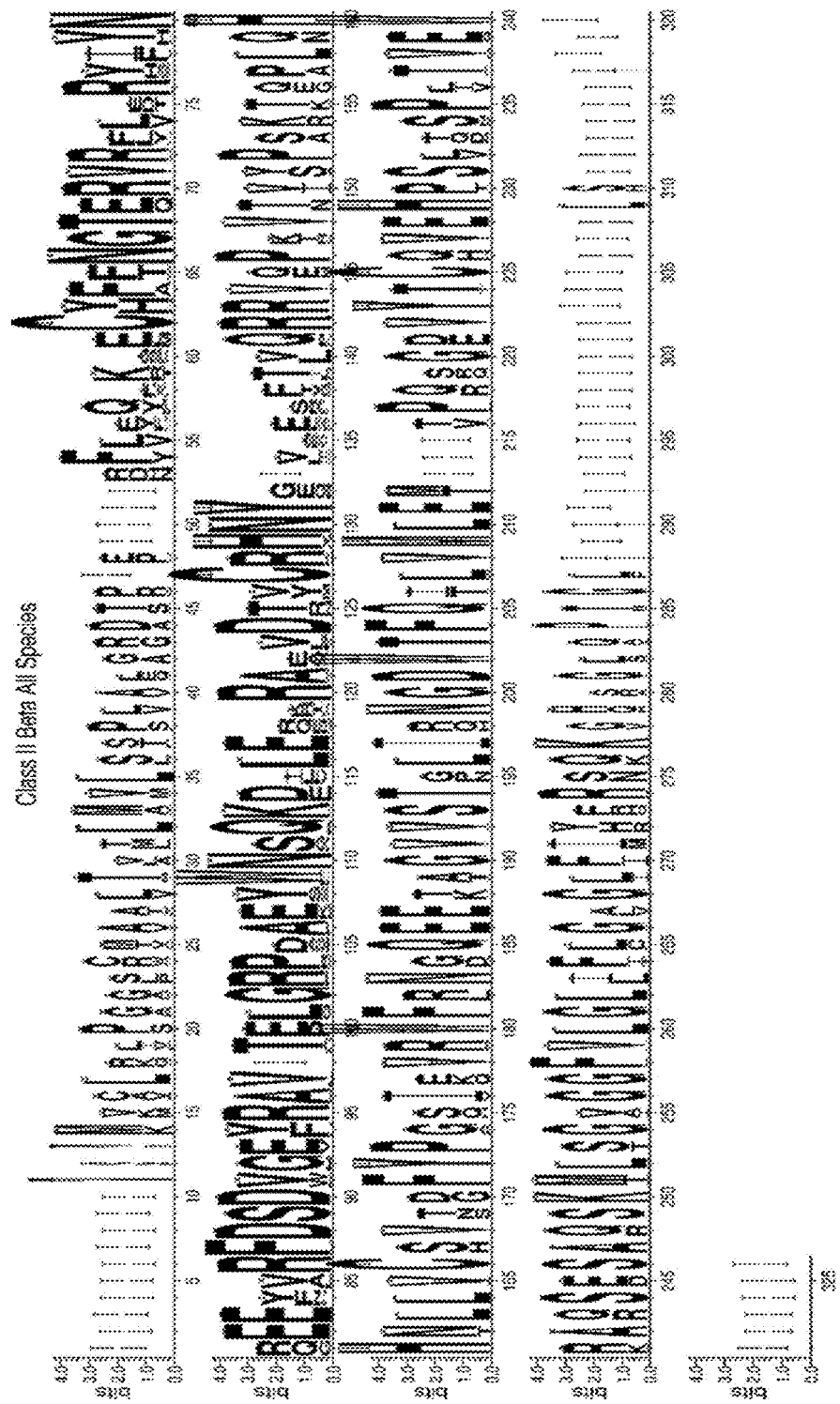
FIG. 20E displays a sequence alignment for class II beta MHC across a wide variety of species.
Figure 20F:
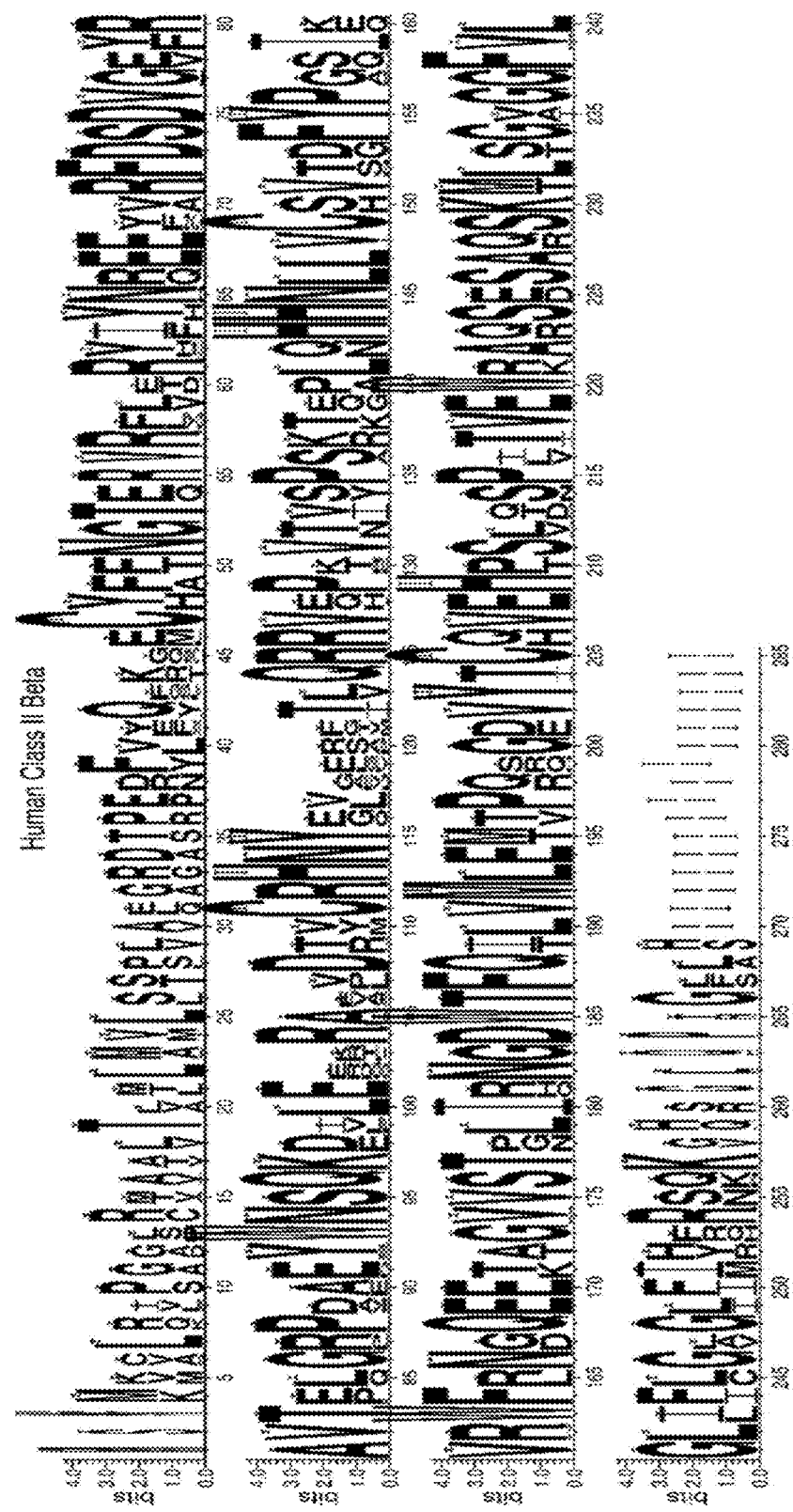
FIG. 20F displays a sequence alignment for class II beta MHC across humans.

In some embodiments, any species, variant, deletion, or modified version of each of the noted protein components (especially MHC fragment) can be employed, as long as they function as described herein. In some embodiments, this is achieved if the sequence employed is a human sequence for the component provided herein. In some embodiments, the sequence of the component can be mammalian. In some embodiments, the sequence of the component can be 80% or greater identity to a sequence provided herein or the human sequence of the component provided herein, for example, 80, 85, 90, 91, 92, 93, 94, 95, 96, 97, 98, 99, 99.9% or greater identity to the human sequence of the component (e.g., MHC, epitope, etc.). In some embodiments, the component can be a variant, as long as those sequences that are conserved between organisms are maintained. Examples of such permissible variants are described in the logo based sequence alignments provided in FIGS. 20A-20F. FIG. 20A displays a sequence alignment for class I MHC across a wide variety of species. FIG. 20B displays a sequence alignment for class I MHC across humans. FIG. 20C displays a sequence alignment for class II alpha MHC across a wide variety of species. FIG. 20D displays a sequence alignment for class II alpha MHC across humans. FIG. 20E displays a sequence alignment for class II beta MHC across a wide variety of species. FIG. 20F displays a sequence alignment for class II beta MHC across humans. With this information, one of skill in the art will appreciate those sections of the protein that are conserved and thus important for function, and those sections that are not conserved and thus can be varied.

The images in FIGS. 20A-20F are sequence logos, which are graphical representations of an amino acid or nucleic acid multiple sequence alignment. The logo is a sequence of stacks of letters, one stack for each position in the amino acid sequence alignment. The overall height of the stack indicates the sequence conservation at that position, while the height of symbols within the stack indicates the relative frequency of each amino or nucleic acid at that position. Similar to a stacked bar graph, where the one-letter code of the amino acid is used instead of a colored bar. The width of the stack is proportional to the fraction of missing sequences at that position. It is noted that many of the MHC molecules do not contain full sequences. Thinner letters mean that some sequences are missing information for that region. In these depictions, the width of the letters shouldn't matter overly. In some embodiments, the guidance is focused on those sections from parts that have deeper sequencing coverage.

REFERENCES

All references are incorporated by reference in their entireties.

Shankar an, V. et al. IFNgamma and lymphocytes prevent primary tumour development and shape tumour immunogenicity. Nature 410, 1107-1111, doi:10.1038/35074122 (2001).

Lollini, P. L., Cavallo, F., Nanni, P. & Forni, G. Vaccines for tumour prevention. Nature reviews. Cancer 6, 204-216, doi:10.1038/nrc1815 (2006).

Leach, D. R., Krummel, M. F. & Allison, J. P. Enhancement of antitumor immunity by CTLA-4 blockade. Science 271, 1734-1736 (1996).

Dong, H. et al. Tumor-associated B7-H1 promotes T-cell apoptosis: a potential mechanism of immune evasion. Nature medicine 8, 793-800, doi:10.1038/nm730 (2002).

Yee, C. et al. Adoptive T cell therapy using antigen-specific CD8+ T cell clones for the treatment of patients with metastatic melanoma: in vivo persistence, migration, and antitumor effect of transferred T cells. Proceedings of the National Academy of Sciences of the United States of America 99, 16168-16173, doi:10.1073/pnas.242600099 (2002).

Davis, M. M. & Bjorkman, P. J. T-cell antigen receptor genes and T-cell recognition. Nature 334, 395-402, doi:10.1038/334395a0 (1988).

Weiss, A. & Littman, D. R. Signal transduction by lymphocyte antigen receptors. Cell 76, 263-274 (1994).

Bethune, M. T. & Joglekar, A. V. Personalized T cell-mediated cancer immunotherapy: progress and challenges. Curr Opin Biotechnol 48, 142-152, doi:10.1016/j.copbio.2017.03.024 (2017).

Woodsworth, D. J., Castellarin, M. & Holt, R. A. Sequence analysis of T-cell repertoires in health and disease. Genome Med 5, 98, doi:10.1186/gm502 (2013).

Buchholz, V. R., Schumacher, T. N. & Busch, D. H. T Cell Fate at the Single-Cell Level. Annual review of immunology 34, 65-92, doi:10.1146/annurev-immunol-032414-112014 (2016).

Klenerman, P., Cerundolo, V. & Dunbar, P. R. Tracking T cells with tetramers: new tales from new tools. Nature reviews. Immunology 2, 263-272, doi:10.1038/nri777 (2002).

Castle, J. C. et al. Exploiting the mutanome for tumor vaccination. Cancer research 72, 1081-1091, doi:10.1158/0008-5472.CAN-11-3722 (2012).

Boon, T. & van der Bruggen, P. Human tumor antigens recognized by T lymphocytes. The Journal of experimental medicine 183, 725-729 (1996).

Matsushita, H. et al. Cancer exome analysis reveals a T-cell-dependent mechanism of cancer immunoediting. Nature 482, 400-404, doi:10.1038/nature10755 (2012).

Gee, M. H. et al. Antigen Identification for Orphan T Cell Receptors Expressed on Tumor-Infiltrating Lymphocytes. Cell 172, 549-563 e516, doi:10.1016/j.cell.2017.11.043 (2018).

Birnbaum, M. E. et al. Deconstructing the Peptide-MHC Specificity of T Cell Recognition. Cell 157, 1073-1087, doi:10.1016/j.cell.2014.03.047 (2014).

Yu, Y. Y., Netuschil, N., Lybarger, L., Connolly, J. M. & Hansen, T. H. Cutting edge: single-chain trimers of MHC class I molecules form stable structures that potently stimulate antigen-specific T cells and B cells. Journal of immunology 168, 3145-3149 (2002).

Morgan, R. A. et al. Cancer regression in patients after transfer of genetically engineered lymphocytes. Science 314, 126-129 (2006).

Joglekar, A. V. et al. T cell receptors for the HIV KK10 epitope from patients with differential immunologic control are functionally indistinguishable. Proceedings of the National Academy of Sciences of the United States of America 115, 1877-1882, doi:10.1073/pnas.1718659115 (2018).

Bennett, M. S., Joseph, A., Ng, H. L., Goldstein, H. & Yang, O. O. Fine-tuning of T-cell receptor avidity to increase HIV epitope variant recognition by cytotoxic T lymphocytes. Aids 24, 2619-2628, doi:10.1097/QAD.0b013e32833f7b22 (2010).

Sahin, U. et al. Personalized RNA mutanome vaccines mobilize poly-specific therapeutic immunity against cancer. Nature 547, 222-226, doi:10.1038/nature23003 (2017).

Li, H. & Durbin, R. Fast and accurate short read alignment with Burrows-Wheeler transform. Bioinformatics 25, 1754-1760, doi:10.1093/bioinformatics/btp324 (2009).

Vita, R. et al. The immune epitope database (IEDB) 3.0. Nucleic acids research 43, D405-412, doi:10.1093/nar/gku938 (2015).

Yokomaku, Y. et al. Impaired processing and presentation of cytotoxic-T-lymphocyte (CTL) epitopes are major escape mechanisms from CTL immune pressure in human immunodeficiency virus type 1 infection. Journal of virology 78, 1324-1332 (2004).

Dorrell, L. et al. Distinct recognition of non-clade B human immunodeficiency virus type 1 epitopes by cytotoxic T lymphocytes generated from donors infected in Africa. Journal of virology 73, 1708-1714 (1999).

Peakman, M. et al. T cell clones generated from patients with type 1 diabetes using interleukin-2 proliferate to human islet antigens. Autoimmunity 17, 31-39 (1994).

Tang, Q. & Bluestone, J. A. The Foxp3+ regulatory T cell: a jack of all trades, master of regulation. Nature immunology 9, 239-244, doi:10.1038/ni1572 (2008).

Garcia, K. C. et al. Structural basis of plasticity in T cell receptor recognition of a self peptide-MHC antigen. Science 279, 1166-1172 (1998).

Taguchi, T. et al. Detection of individual mouse splenic T cells producing IFN-gamma and IL-5 using the enzyme-linked immunospot (ELISPOT) assay. Journal of immunological methods 128, 65-73 (1990).

Suwandi, J. S., Nikolic, T. & Roep, B. O. Translating Mechanism of Regulatory Action of Tolerogenic Dendritic Cells to Monitoring Endpoints in Clinical Trials. Frontiers in immunology 8, 1598, doi:10.3389/fimmu.2017.01598 (2017).

Bentzen, A. K. & Hadrup, S. R. Evolution of MHC-based technologies used for detection of antigen-responsive T cells. Cancer immunology, immunotherapy: CII 66, 657-666, doi:10.1007/s00262-017-1971-5 (2017).

Tran, E. et al. Cancer immunotherapy based on mutation-specific CD4+ T cells in a patient with epithelial cancer. Science 344, 641-645, doi:10.1126/science.1251102 (2014).

Bassani-Sternberg, M. et al. Direct identification of clinically relevant neoepitopes presented on native human melanoma tissue by mass spectrometry. Nature communications 7, 13404, doi:10.1038/ncomms13404 (2016).

Roep B O (2003) The role of T-cells in the pathogenesis of Type 1 diabetes: from cause to cure. Diabetologia 46(3): 305-321.

Sharma G & Holt R A (2014) T-cell epitope discovery technologies. Human immunology 75(6):514-519.

Bentzen A K & Hadrup S R (2017) Evolution of MHC-based technologies used for detection of antigen-responsive T cells. Cancer immunology, immunotherapy: CII 66(5): 657-666.

Pike K A, Hui C, & Krawczyk C M (2016) Detecting Secreted Analytes from Immune Cells: An Overview of Technologies. Methods in molecular biology 1458:111-124.

Nepom G T, et al. (2002) HLA class II tetramers: tools for direct analysis of antigen-specific CD4+ T cells. Arthritis and rheumatism 46(1):5-12.

Arif S, et al. (2004) Autoreactive T cell responses show proinflammatory polarization in diabetes but a regulatory phenotype in health. The Journal of clinical investigation 113(3):451-463.

Van Lummel M, et al. (2012) Type 1 diabetes-associated HLA-DQ8 transdimer accommodates a unique peptide repertoire. The Journal of biological chemistry 287(12): 9514-9524.

Kracht M J, et al. (2017) Autoimmunity against a defective ribosomal insulin gene product in type 1 diabetes. Nature medicine 23(4):501-507.

Beringer D X, et al. (2015) T cell receptor reversed polarity recognition of a self-antigen major histocompatibility complex. Nature immunology 16(11):1153-1161.

Alhadj Ali M, et al. (2017) Metabolic and immune effects of immunotherapy with proinsulin peptide in human new-onset type 1 diabetes. Science translational medicine 9(402).

LENGTHY TABLES

The patent contains a lengthy table section. A copy of the table is available in electronic form from the USPTO web site (https://seqdata.uspto.gov/?pageRequest=docDetail&DocID=US12221465B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12221465B2). An electronic copy of the sequence listing will also be available from the USPTO upon request and payment of the fee set forth in 37 CFR 1.19(b)(3).

What is claimed is:

1. A signaling and antigen-presenting bifunctional receptor (SABR) comprising:

an antigen presenting domain comprising a binding domain of a major histocompatibility complex (MHC) molecule, a peptide epitope covalently linked to the binding domain of the MHC molecule for extracellular presentation of the peptide epitope to a first cell expressing at least one antigen receptor, and a transmembrane domain;

one or more linkers; and a signal transduction domain fused to the antigen presenting domain, wherein the SABR is made by a method comprising expressing, in a second cell that is an isolated cell, a nucleic acid sequence encoding the antigen presenting domain, the signal transduction domain, and the one or more linkers, and wherein the peptide epitope is synthesized and cloned, from pooled single stranded oligonucleotide libraries, into the nucleic acid sequence, wherein the transmembrane domain comprises a transmembrane domain from one or more of 4-1BB (CD137), CD28, CD27, DAP10, ICOS, OX40, PD1, CTLA4, TIM3, CD3zeta, Notch, synNotch, CD79A, CD79B, CD72, CD22, CD5, CD19, CD45, IL2, IL4, EPO, GM-CSF, JAK-STAT, CCL10, a G protein coupled receptor, a receptor of the TNF Receptor superfamily, a NK cell receptor, a Fc receptor, a toll-like receptor, a RIG-I-like receptor, a NOD-like receptor, or a MHC molecule, and wherein the signal transduction domain comprises an intracellular signaling domain of CD137, CD27, DAP10, ICOS, OX40, PD1, CTLA4, TIM3, an IL2, an IL4, an EPO, a GM-CSF, JAK-STAT, a CCL10, a G protein coupled receptor, or a receptor of the TNF Receptor superfamily, or a fragment thereof.

2. The SABR of claim 1, wherein the antigen presenting domain comprises the MHC.

3. The SABR of claim 1, wherein the MHC comprises a Class I MHC, and
wherein the MHC comprises HLA-A*0201 or HLA-B*2705.

4. The SABR of claim 1, wherein the MHC comprises a Class II MHC.

5. The SABR of claim 1, wherein the second cell is a reporter cell, and
wherein the reporter cell provides a detectable marker upon binding of the SABR to the antigen receptor.

6. The SABR of claim 5, wherein the reporter cell comprises NFAT-GFP-Jurkat cells.

7. The SABR of claim 5, wherein the first cell is a T cell comprising TCR.

8. The SABR of claim 5, wherein the first cell expresses an orphan TCR.

9. The SABR of claim 1, wherein the oligonucleotide libraries encode pathogen epitopes.

10. A signaling and antigen-presenting bifunctional receptor (SABR) comprising:
an antigen presenting domain comprising a major histocompatibility complex (MHC) molecule, a peptide epitope covalently linked to the MHC molecule for extracellular presentation of the peptide epitope to a first cell expressing at least one antigen receptor, and a transmembrane domain;
one or more linkers; and
a signal transduction domain fused to the antigen presenting domain,
wherein the SABR is made by a method comprising expressing, in a second cell that is an isolated cell, a nucleic acid sequence encoding the antigen presenting domain and the signal transduction domain, wherein the MHC molecule is class I or class II,
wherein the peptide epitope is synthesized and cloned, from pooled single stranded oligonucleotide libraries, into the nucleic acid sequence,
wherein the peptide epitope comprises a cancer peptide epitope,
wherein the transmembrane domain comprises a transmembrane domain from one or more of 4-1BB (CD137), CD28, CD27, DAP10, ICOS, OX40, PD1, CTLA4, TIM3, CD3zeta, Notch, synNotch, CD79A, CD79B, CD72, CD22, CD5, CD19, CD45, IL2, IL4, EPO, GM-CSF, JAK-STAT, CCL10, a G protein coupled receptor, a receptor of the TNF Receptor superfamily, a NK cell receptor, a Fc receptor, a toll-like receptor, a RIG-I-like receptor, a NOD-like receptor, or an MHC molecule, and
wherein the signal transduction domain comprises an intracellular signaling domain of CD137, CD27, DAP10, ICOS, OX40, PD1, CTLA4, TIM3, an IL2, an IL4, an EPO, a GM-CSF, JAK-STAT, a CCL10, a G protein coupled receptor, or a receptor of the TNF Receptor superfamily, or a fragment thereof.

* * * * *